(12) United States Patent
Inglis et al.

(10) Patent No.: US 7,374,768 B1
(45) Date of Patent: May 20, 2008

(54) VIRAL VACCINES

(75) Inventors: Stephen Charles Inglis, Linton (GB); Michael Edward Griffith Boursnell, Cambridge (GB); Anthony Charles Minson, Great Shelford (GB)

(73) Assignee: Xenova Research Limited, Cambridge (GB)

( * ) Notice: Subject to any disclaimer, the term of this patent is extended or adjusted under 35 U.S.C. 154(b) by 0 days.

(21) Appl. No.: 08/459,040

(22) Filed: Jun. 2, 1995

Related U.S. Application Data

(63) Continuation-in-part of application No. 08/384,963, filed on Feb. 7, 1995, now Pat. No. 5,665,362, which is a continuation-in-part of application No. 08/216,260, filed on Mar. 21, 1994, now Pat. No. 5,837,261, which is a continuation-in-part of application No. 08/168,643, filed on Dec. 16, 1993, now abandoned, which is a continuation of application No. 08/030,073, filed on May 20, 1993, now abandoned.

(30) Foreign Application Priority Data

| Sep. 25, 1990 | (GB) | 9020799.4 |
| Mar. 8, 1991 | (GB) | 9104903.1 |
| Sep. 23, 1991 | (WO) | PCT/GB91/01632 |
| Dec. 16, 1992 | (GB) | 9226172.6 |
| Mar. 19, 1993 | (GB) | 9305710.7 |
| Dec. 6, 1993 | (GB) | 9324964.7 |

(51) Int. Cl.
*A61K 39/275* (2006.01)
*A61K 39/285* (2006.01)

(52) U.S. Cl. .............. 424/232.1; 424/199.1; 435/235.1; 435/236

(58) Field of Classification Search .......... 424/199.1, 424/205.1, 229.1, 231.1; 435/172.3, 235.1, 435/240.2; 935/65
See application file for complete search history.

(56) References Cited

U.S. PATENT DOCUMENTS

| 4,722,848 | A |   | 2/1988 | Paoletti et al. |   |
| 4,996,152 | A | * | 2/1991 | Carter et al. | 435/172.3 |
| 5,110,587 | A |   | 5/1992 | Paoletti et al. |   |
| 5,155,020 | A |   | 10/1992 | Paoletti |   |
| 5,166,057 | A | * | 11/1992 | Palese et al. |   |
| 5,174,993 | A |   | 12/1992 | Paoletti |   |
| 5,204,243 | A |   | 4/1993 | Paoletti |   |
| 5,225,336 | A |   | 7/1993 | Paoletti |   |
| 5,338,683 | A | * | 8/1994 | Paoletti | 435/320.1 |
| 5,364,773 | A |   | 11/1994 | Paoletti et al. |   |
| 5,453,364 | A |   | 9/1995 | Paoletti |   |
| 5,494,807 | A | * | 2/1996 | Paoletti et al. | 435/69.3 |
| 5,505,941 | A |   | 4/1996 | Paoletti |   |
| 5,583,028 | A |   | 12/1996 | Paoletti et al. |   |
| 5,766,882 | A | * | 6/1998 | Falkner et al. | 435/69.1 |
| 5,770,212 | A | * | 6/1998 | Falkner et al. | 424/199.1 |

FOREIGN PATENT DOCUMENTS

| EP | 0213894 | 3/1987 |
| EP | 0386882 | 9/1990 |
| EP | 0453242 | 10/1991 |
| EP | 0 753 581 A1 | 1/1997 |
| WO | WO 8909271 | 10/1989 |
| WO | WO 9005538 | 5/1990 |
| WO | WO 9010693 | 9/1990 |
| WO | WO 9105055 | 4/1991 |
| WO | 9205263 | 4/1992 |
| WO | WO 94032074 | 2/1994 |
| WO | WO-95/27507 A1 | 10/1995 |
| WO | WO-96/21727 A1 | 7/1996 |
| WO | WO-96/39177 A1 | 12/1996 |
| WO | WO-96/39491 A1 | 12/1996 |
| WO | WO-96/40241 A1 | 12/1996 |

OTHER PUBLICATIONS

Ballay A. et al. In vitro and in vivo synthesis of the hepatitis B virus surface antigen and of the receptor for polymerized human sesion albamins From recombinant Human adenoviruses The EMBO Journal vol. 4: 3861-3865 (1985).*

Alkhatib G. et al. High level eukaryotic In vivo expression of biologically active Meades virushemoglutin by using an adenovirus Type 5 helper-free vector system. J. Virology 62:2718-2727 (1988).*

Hutchinson et al. "A Novel Herpes Simplex Virus Glycoprotein, gL, Forms a Complex with Glycoprotein H (gH) and Affects Normal Folding and Surface Expression of gH". Journal of Virology. vol. 66, No. 4, pp. 2240-2250, Apr. 1992.*

(Continued)

*Primary Examiner*—Mary E Mosher
(74) *Attorney, Agent, or Firm*—Connolly Bove Lodge & Hutz LLP

(57) ABSTRACT

A mutant virus for use as a vaccine for prophylaxis or therapy, wherein the genome of the virus is defective in respect of a gene essential for the production of infectious virus. In one aspect the mutant virus, e.g. a herpesvirus, e.g HSV-1 or HSV-2, is capable of protecting a susceptible species immunised therewith against infection by the corresponding wild-type virus. In another aspect, the mutant virus acts as a vector for an immunogenic protein derived from a pathogen, encoded by foreign DNA incorporated in the mutant virus. The mutant virus can be produced by a recombinant host cell which expresses a gene complementing the defect. The mutant virus can be infectious for the host to be protected, and the genetic defect can allow expression in the infected host of at least some of the viral genes, which can provoke a cell-mediated immune response. The defect can be in a glycoprotein gene such as gH.

3 Claims, 37 Drawing Sheets

OTHER PUBLICATIONS

Schranz et al. "A Viable HSV-1 Mutant Deleted in Two Nonessential Major Glycoproteins". Virology. vol. 170, pp. 273-276, 1989.*

Haj-Ahmad et al. "Development of a Helper-Independent Human Adenovirus Vector and Its Use in the Transfer of the Herpes Simplex Virus Thymidine Kinase Gene". Journal of Virology. vol. 57, No. 1, pp. 267-274, Jan. 1986.*

Weber et al. "Rapid Identification of Nonessential Genes of Herpes Simplex Virus Type 1 by Tn5 Mutagenesis". Science. vol. 236, pp. 576-579, May 1, 1987.*

Ligas et al. "A Herpes Simplex Virus Mutant in Which Glycoprotein D Sequences Are Replaced by Beta-Galactosidase Sequences Binds to but Is Unable to Penetrate into Cells". Journal of Virology. vol. 62, No. 5, pp. 1486-1494, May 1986.*

Moss, B. 1985. Virology, ed. B. N. Fields et al, Raven Press, NY, pp. 685-703, 1985.*

Miner, J/N et al. 1990. Virus Genes, vol. 3:4, pp. 355-359, 1990.*

Roizman et al. Herpesviruses and Their Replication. In Virology, ed. B. N. Fields et al, Raven Press, NY, p. 497-526, 1985.*

Farrell, H.E., et al., "Vaccine Potential of a Herpes Simplex Virus Type 1 Mutant with an Essential Glycoprotein Deleted" *Journal of Virology*, 68(2) :927-932 (1994).

Morrison, L.A., et al., "Immunization with Relication-Defective Mutants of Herpes Simplex Virus Type 1: Sites of Immune Intervention in Pathogenesis of Challenge Virus Infection." *Journal of Virology*, 68(2) :689-696 (1994).

Peeters, B., et al., "Non-Transmissible Pseudorabies Virus gp50 Mutants: A New Generation of Safe Live Vaccines." *Vaccine*, 12(4) :375-380 (1994).

Nguyen, L.H., et al., "Replication-Defective Mutants of Herpes Simplex Virus (HSV) Induce Cellular Immunity and Protect Against Lethal HSV Infection." *Journal of Virology*, 66(12) :7067-7072 (1992).

Graham, F.L., et al., "Characteristics of a Human Cell Line Transformed by DNA from Human Adenovirus Type 5." *J. Gen. Virol.*, 36:59-72 (1977).

Harrison, T., et al., "Host-Range Mutants of Adenovirus Type 5 Defective for Growth in HeLa Cells." *Virology*, 77:319-329 (1977).

Gluzman, Y., "SV40-Transformed Simian Cells Support the Replication of Early SV40 Mutants." *Cell*, 23:175-182 (1981).

Cai, W., et al., "Linker-Insertion Nonsense and Restriction-Site Deletion Mutations of the gB Glycoprotein Gene of Herpes Simplex Virus Type 1." *Journal of Virology*, 61(3) :714-721 (1987).

Racaniello, V.R., et al., "Cloned Poliovirus Complementary DNA is Infectious in Mammalian Cells." *Science*, 214:916-918 (1981).

Ligas, M.W., et al., "A Herpes Simplex Virus Mutant in which Glycoprotein D Sequences are Replaced by β-Galactosidase Sequences Binds to but is Unable to Penetrate into Cells." *Journal of Virology*, 62(5) :1486-1494 (1988).

Fuller, A.O., et al., "Neutralizing Antibodies Specific for Glycoprotein H of Herpes Simplex Virus Permit Viral Attachment to Cells but Prevent Penetration." *Journal of Virology*, 63(8) :3435-3443 (1989).

DeLuca, N.A., et al., "Isolation and Characterization of Deletion Mutants of Herpes Simplex Virus Type 1 in the Gene Encoding Immediate-Early Regulatory Protein ICP4." *Journal of Virology*, 56(2) :558-570 (1985).

Johnson, D.C., et al., "Herpes Simplex Viruses Lacking Glycoprotein D are Unable to Inhibit Virus Penetration: Quantitative Evidence for Virus-Specific Cell Surface Receptors." *Journal of Virology*, 62(12) :4605-4612 (1988).

Desai, P.J., et al., "Excretion of Non-Infectious Virus Particles Lacking Glycoprotein H by a Temperature-Sensitive Mutant of Herpes Simplex Virus Type 1: Evidence that gH is Essential for Virion Infectivity." *J. Gen. Virol.*, 69:1147-1156 (1988).

Luytjes, W., et al., "Amplification, Expression, and Packaging of a Foreign Gene by Influenza Virus." *Cell*, 59:1107-1113 (1989).

Buller, R.M.L., et al., Deletion of the Vaccinia Virus Growth Factor Gene Reduces Virus Virulence, *Journal of Virology*, 62(3) :866-874 (1988).

Eliot, M., et al., "Construction of a Defective Adenovirus Vector Expressing the Pseudorabies Virus Glycoprotein gp50 and its Use as a Live Vaccine." *Journal of Gen. Virol.*, 71, 2425-2431 (1990).

Forrester, A., et al., "Construction and Properties of a Mutant of Herpes Simplex Virus Type 1 with Glycoprotein H Coding Sequences Deleted." *Journal of Virology*, 66(1) :341-348 (1992).

Ragot, T., et al., "Replication-Defective Recombinant Adenovirus Expressing the Epstein-Barr Virus (EBV) Envelope Glycoprotein gp340/220 Induces Protective Immunity Against EBV-Induced Lymphomas in the Cottontop Tamarin." *Journal of General Virology*, 74 :501-507 (1993).

Emi, N., et al., "Pseudotype Formation of Murine Leukemia Virus with the G Protein of Vesicular Stomatitis Virus." *Journal of Virology*, 65(3) :1202-1207 (1991).

Dion, M., et al., "Isolation and Preliminary Characterization of Temperature-Sensitive Mutants of Human Cytomegalovirus." *Virology*, 158:228-230 (1987).

McGeoch, D.J., "The Genomes of the Human Herpes Viruses: Contants, Relationships, and Evolution." *Ann. Rev. Microbiol.*, 43:235-265 (1989).

Ensinger, M.J., et al., "Fine Structure Marker Rescue of Temperature-Sensitive Mutations of Vaccinia Virus Within a Central Conserved Region of the Genome." *Journal of Virology*, 56(3):1027-1029 (1985).

Frost, E., et al., "Mapping Temperature-Sensitive and Host-Range Mutations of Adenovirus Type 5 by Marker Rescue." *Virology*, 91:39-50 (1978).

Goebel, S.J., et al., "The Complete DNA Sequence of Vaccinia Virus." *Virology*, 179:247-266 (1990).

Almond, J.W., et al., "Temperature-Sensitive Mutants of Fowl Plague Virus: Isolation and Genetic Characterization." *Virology*, 92:416-427 (1979).

Straus, S.E., et al., "Placebo-Controlled Trial of Vaccination with Recombinant Glycoprotein D of Herpes Simplex Virus Type 2 for Immunotherapy of Genital Herpes." *The Lancet*, 343:1460-1463 (1994).

McGeoch, D.J., et al., "DNA Sequence of the Herpes Simplex Virus Type I Gene Encoding Glycoprotein gH, and Identification of Homologues in the Genomes of Varicella-Zoster Virus and Epstein-Barr Virus." *Nucleic Acids Research*, 14(10) :4281-4292 (1986).

Gao, M., et al., "Genetic Evidence for Multiple Nuclear Functions of the Herpes Simplex Virus ICP8 DNA-Binding Protein." *Journal of Virology*, 63(12) :5258-5267 (1989).

McCarthy, A.M., et al., "Herpes Siimplex Virus Type 1 ICP27 Deletion Mutants Exhibit Altered Patterns of Transcription and are DNA Deficient." *Journal of Virology*, 63(1) :18-27 (1989).

Ross, L.J.N., et al., "Nucleotide Sequence and Characterization of the Marek's Disease Virus Homologue of Glycoprotein B of Herpes Simplex Virus." *J. Gen. Virol.*, 80:1789-1804 (1989).

Whitbeck, J.C., et al., "Comparison of the Bovine Herpesvirus 1 gI Gene and the Herpes Simplex Virus Type 1 gB Gene." *Journal of Virology*, 62(9) :3319-3327 (1988).

Hammerschmidt, W., et al., "Conservation of a Gene Cluster Including Glycoprotein B in Bovine Herpesvirus Type 2 (BHV-2) and Herpes Simplex Virus Type 1 (HSV-2)." *Virology*, 165:388-405 (1988).

Chen, K.C., et al., "Complete Nucleotide Sequence and Genome Organization of Bovine Parvovirus." *Journal of Virology*, 60(3) :1085-1097 (1986).

Cotmore, S.F., "Identification of the Major Structural and Nonstructural Proteins Encoded by Human Parvovirus B19 and Mapping of Their Genes by Procaryotic Expression of Isolated Genomic Fragments." *Journal of Virology*, 60(2) :548-557 (1986).

Long, D., et al., "Glycoprotein D Protects Mice Against Lethal Challenge with Herpes Simplex Virus Types 1 and 2." *Infection and Immunity*, 43:761-764 (1984).

Straus, S.E., et al., "Induction and Enhancement of Immune Responses to Herpes Simplex Virus Type 2 in Humans by Use of a Recombinant Glycoprotein D Vaccine." *The Journal of Infectious Diseases*, 167:1045-1052 (1993).

Pachl, C., et al., "Expression of Cell-Associated and Secreted Forms of Herpes Simplex Virus Type 1 Glycoprotein gB in Mammalian Cells." *Journal of Virology*, 61(2) :315-325 (1987).

Ghiasi, H., et al., "Expression of Seven Herpes Simplex Virus Type 1 Glycoproteins (gB, gC, gD, gE, gH, and gI): Comparative Protection Against Lethal Challenge in Mice." *Journal of Virology*, 68(4) :2118-2126 (1994).

Garcia, N., "Vaccine Reduces Herpes Outbreaks." *BioWorld Today*, 4(86) :1-4 (1993).

Stanberry, L.R., et al., "Genital Herpes in Guinea Pigs: Pathogenesis of the Primary Infection and Description of Recurrent Disease." *The Journal of Infectious Diseases*, 146(3) :397-404 (1982).

Cranage, M.P., et al., "Identification and Expression of a Human Cytomegalovirus Glycoprotein with Homology to the Epstein-Barr Virus BXLF2 Product, Varicella-Zoster Virus gpIII, and Herpes Simplex Virus Type 1 Glycoprotein H." *Journal of Virology*, 62(4) :1416-1422 (1988).

Mester, J.C., et al., "The Mouse Model and Understanding Immunity to Herpes Simplex Virus." *Reviews of Infectious Diseases*, 13:S935-S945 (1991).

Thomas, G.P., M.B. Mathews, "DNA Replication and the Early to Late Transition in Adenovirus Infection." *Cell*, 22:523-533 (1980).

Fiers, W., et al., "Complete Nucleotide Sequence of SV40 DNA." *Nature*, 273:113-120 (1978).

Somogyi, P., et al., "Fowlpox Virus Host Range Restriction: Gene Expression, DNA Replication, and Morphogenesis in Nonpermissive Mammalian Cells." *Virology*, 197:439-444 (1993).

Perkus, M.E., et al., "Vaccinia Virus Host Range Genes." *Virology*, 179:276-286 (1990).

Tashiro, M., et al., "Cell-Mediated Immunity Induced in Mice after Vaccination with a Protease Activation Mutant, TR-2, of Sendai Virus." *Journal of Virology*, 62:2490-2497 (1988).

Beatrice, S.T., and R.R. Wagner, "Immunogenicity in Mice of Temperature-Sensitive Mutants of Vesicular Stomatitis Virus: Early Appearance in Bronchial Secretions of an Interferon-Like Inhibitor." *J. Gen. Virol.*, 47:529-533 (1980).

McLaren, L.C. and J.J. Holland, "Defective Interfering Particles from Poliovirus Vaccine and Vaccine Reference Strains." *Virology*, 60:579-583 (1974).

Konishi, E., et al., "A Highly Attenuated Host Range-Restricted Vaccinia Virus Strain, NYVAC, ENcoding the prM, E and NS1 Genes of Japanese Encephalitis Virus Prevents JEV Viremia in Swine." *Virology*, 190:454-458 (1992).

Tartaglia, J., et al., "NYVAC: A Highly Attenuated Strain of Vaccinia Virus." *Virology*, 188:217-232 (1992).

Goodman Gilman, "The Pharmacologic Basis of Therapeutic" 8th Ed., (1990) pp. 1184-1186.

Akrigg, A., et al., "The Structure of the Major Immediate Early Gene of Human Cytomegalovirus Strain AD169." *Virus Research*, 2:107-121 (1985).

Brierley, I., et al., "Characterization of an Efficient Coronavirus Ribosomal Frameshifting Signal: Requirement for an RNA Pseudoknot." *Cell*, 57:537-547 (1989).

Chakrabarti, L., et al., "Sequence of Simian Immunodeficiency Virus From Macaque and its Relationship to Other Human and Simian Retroviruses." *Nature*, 328(6) :543-547 (1987).

Graham, F.L., et al., "A New Technique for the Assay of Infectivity of Human Adenovirus 5 DNA." *Virology*, 52:456-467 (1973).

Chakrabarti, S., et al., "Vaccinia Virus Expression Vector: Coexpression of β-Galactosidase Provides Visual Screening of Recombinant Virus Plaques." *Molecular and Cellular Biology*, 5(12) :3403-3409 (1985).

Everett, R.D., et al., "DNA Sequence Elements Required for Regulated Expression of the HSV-1 Glycoprotein D Gene Lie Within 83 bp of the RNA Capsites." *Nucleic Acids REsearch*, 11(19) :6647-6666 (1983).

Gompels, U.A., et al., "Antigenic Properties and Cellular Localization of Herpes Simplex Virus Glycoprotein H Synthesized in a Mammalian Cell Expression System." *Journal of Virology*, 63(11) :4744-4755 (1989).

Krieg, P.A., et al., "Functional Messenger RNAs are Produced by SP6 in vitro Transcription of Cloned cDNAs." *Nucleic Acids Research*, 12 (18):7057-7070 (1984).

McGeoch, G.J., et al., "The Complete DNA Sequence of the Long Unique Region in the Genome of Herpes Simplex Virus Type 1." *J. Gen. Virol.*, 69:1531-1574 (1988).

Twigg, A.J., et al., "Trans-Complementable Copy-Number Mutants of Plasmid ColE1." *Nature*, 283:216-218 (1980).

Vieira, J., et al., "[1] Production of Single-Stranded Plasmid DNA." *Methods in Enzymology*, 143:3-11 (1987).

Hill, T.J., et al., "Acute and Recurrent Infection with Herpes Simplex Virus in the Mouse: a Model for Studying Latency and Recurrent Disease." *J. Gen. Virol.*, 28:341-343 (1975).

Gallichan, W.S., et al., "Mucosal Immunity and Protection after Intranasal Immunization with Recombinant Adenovirus Expressing Herpes Simplex Virus Glycoprotein B." *The Journal of Infectious Diseases*, 168:622-629 (1993).

Stanberry, L.R., et al., "Herpes Simplex Virus Glycoprotein Treatment of Recurrent Genital Herpes," *The Journal of Infectious Diseases*, 157(1):156-163 (1988).

Stanberry, L.R., et al., "Preinfection Prophylaxxis with Herpes Simplex Virus Glycoprotein Immunogens: Factor Influencing Efficacy." *J. Gen. Virol.*, 70:3177-3185 (1989).

Baer, R., et al., "DNA Sequence and Expression of the B95-8 Epstein-Barr Virus Genome." *Nature*, 310:207-211 (1984).

Killington, R.A., et al., "Growth, Assay and Purification of Herpesviruses." *Techniques in Virology*, 207-236 (1994).

Rauh et al., "Pseudorabies Virus Glycoproteins gII and gp50 Are Essential for Virus Penetration," *Journal of Virology*, 65(10):5348-5356 (1991).

Miner et al., Anchoring a Vaccinia Virus Promoter in the Nucleus Prevents its Trans-Activation by Viral Infection, *Virus Genes*, 3(4):335-359 (1990).

Moss, B., "Replication of Poxviruses," *Virology*, Ed. B.N. Fields et al., Raven Press:N.Y., p. 685-703 (1985).

Peeters et al., "Pseudorabies Virus Envelope Glycoproteins gp50 and gII are Essential for Virus Penetration, but only gII is Involved in Membrane Fusion," *Journal of Virology*, 66(2):894-905 (1992).

Blanchard et al., Modified vaccinia virus Ankara undergoes limited replication in human cells and lacks several immunomodulatory proteins: implications for use as a human vaccine. *J. of Gen. Virol.* 79: 1159-1167 (1998).

Blasco et al., Extracellular Vaccinia Virus Formation and Cell-to-Cell Virus Transmission are Prevented by Deletion of the Gene Encoding the 37,000-Dalton Outer Envelope Protein. *J. of Virol.* 65: 5910-5920 (1991).

Borrego et al., Complementation of P37 (F13L gene) knock-out in vaccinia virus by a cell line expressing the gene constitutively. *J. of Gen. Virol.* 80: 425-432 (1999).

Boyle et al., Identification and Cloning of the Fowlpox Virus Thymidine Kinase Gene Using Vaccinia Virus. *J. of Gen. Virol.* 67: 1591-1600 (1986).

Broyles et al., DNA-dependent ATPase Activity Associated with Vaccinia Virus Early Transcription Factor: *J. Biol. Chem.* 263: 10761-10765 (1988).

Broyles et al., Purification of a Factor Required for Transcription of Vaccinia Virus Early Genes. *J. Biol. Chem.* 263: 10754-10760 (1988).

Broyles et al., The Small Subunit of the Vaccinia Virus Early Transcription Factor Contacts the Transcription Promoter DNA. *J. of Virol.* 67:5677-5680 (1993).

Chakrabarti et al., Vaccinia Virus Expression Vector: Coexpression of β-Galactosidase Provides Visual Screening of Recombinant Virus Plaques. *Mol. Cell. Biol.* 5: 3403-3409 (1985).

Chambers et al., Conditional expression of foreign genes by temperature-sensitive mutants of vaccinia virus. *Gene* 95: 275-278 (1990).

Child et al., Insertional inactivation of the large subunit of ribonucleotide reductase encoded by vaccinia virus is associated with reduced virulence in vivo. *Virology* 174: 625-629 (1990). Abstract Only.

Chiu et al., Vaccinia Virus J1R Protein: a Viral Membrane Protein that is Essential for Virion Morphogenesis, *J. of Virol.* 76: 9575-9587 (2002).

Cochran et al., In Vitro Mutagenesis of the Promoter Region for a Vaccinia Virus Gene: Evidence for Tandem Early and Late Regulatory Signals. *J. of Virol.* 54: 30-37 (1985).

Condit et al., Isolation, Characterization, and Physical Mapping of Temperature-Sensitive Mutants of Vaccinia Virus. *Virology* 128: 429-443 (1983).

Condit et al., Orthopoxvirus Genetics. *Current Topics in Microbiology and Immunology* 163:2-39 (1990).

Duncan et al., Identification and Characterization of an Extracellular Envelope Glycoprotein Affecting Vaccinia Virus Egress. *J. of Virol.* 66: 1610-1621 (1992).

Falkner et al., *Escherichia coli* gpt Gene Provides Dominant Selection for Vaccinia Virus Open Reading Frame Expression Vectors. *J. of Virol.* 62: 1849-1854 (1988).

Falkner et al., Transient Dominant Selection of Recombinant Vaccinia Viruses. *J. of Virol.* 64: 3108-3111 (1990).

Fuerst et al., Transfer of the inducible *lac* repressor/operator system from *Escherichia coli* to a vaccinia virus expression vector. *Proc. Natl. Acad. Sci. USA* 86: 2549-2553, 1989.

Gershon et al., Early transcription factor subunits are encoded by vaccinia virus late genes, *Proc. Natl. Acad. Sci. USA* 87: 4401-4405 (1990).

Goebel et al., The Complete DNA Sequence of Vaccinia Virus. *Virology* 179: 247-266 (1990).

Holzer et al., Construction of a Vaccinia Virus Deficient in the Essential DNA Repair Enzyme Uracil DNA Glycosylase by a Complementing Cell Line. *J. of Virol.* 71: 4997-5002 (1997).

Holzer et al., Highly Efficient Induction of Protective Immunity by a Vaccinia Virus Vector Defective in Late Gene Expression. *J. of Virol.* 73: 4536-4542 (1999).

Hruby, Vaccinia Virus Vectors: New Strategies for Producing Recombinant Vaccines. *Clin. Microbiol. Rev.* 3: 153-170 (1990).

Hubbs et al., The A2L Intermediate Gene Product is Required for in Vitro Transcription from a Vaccinia Virus Late Promoter. *J. of Virol.* 70: 327-331 (1996).

Hughes et al., Vaccinia Virus Encodes an Active Thymidylate Kinase that Complements a *cdc8* Mutant of *Saccharomyces cerevisiae*. *J. Biol. Chem.* 266: 20103-20109 (1991).

Isaacs et al., Reverse Guanine Phosphoribosyltransferase Selection of Recombinant Vaccinia Viruses. *Virology* 178: 626-630 (1990).

Iyer et al., Common Origin of Four Diverse Families of Large Eukaryotic DNA Viruses. *J. of Virol.* 75: 11720-11734 (2001).

Jindal et al., Vaccinia Virus Infection Induces a Stress Response that Leads to Association of Hsp70 with Viral Proteins. *J. of Virol.* 68: 5357-5362 (1992).

Kane et al., Vaccinia Virus Morphogenesis is Blocked by a Temperature-Sensitive Mutation in the I7 Gene that Encodes a Virion Component. *J. of Virol.* 67: 2689-2698 (1993).

Kane et al., Temperature-Sensitive Mutations in the Vaccinia Virus H4 Gene Encoding a Component of the Virion RNA Polymerase. *J. of Virol.* 66: 5752-5762 (1992).

Keck et al., Overexpression, Purification, and Late Transcription Factor Activity of the 17-Kilodalton Protein Encoded by the Vaccinia Virus A1L Gene. *J. of Virol.* 67: 5740-5748 (1993).

Lai et al., Structural and Functional Properties of the 14-kDa Envelope Protein of Vaccinia Virus Synthesized in *Escherichia coli*. *J. Biol. Chem.* 265: 22174-22180 (1990).

Lee et al., Molecular Attenuation of Vaccinia Virus: Mutant Generation and Animal Characterization. *J. of Virol.* 66: 2617-2630 (1992).

Li et al., The DNA-dependent ATPase Activity of Vaccinia Virus Early Gene Transcription Factor is Essential for its Transcription Activation Function. *J. Biol. Chem.* 268: 20016-20021 (1993).

Li et al., Temperature-Sensitive Mutations in the Gene Encoding the Small Subunit of the Vaccinia Virus Early Transcription Factor Impair Promoter Binding, Transcription Activation, and Packaging of Multiple Virion Components. *J. of Virol.* 68: 2605-2614 (1994).

Li et al., Expression of the M Gene of Vesicular Stomatitis Virus Cloned in Various Vaccinia Virus Vectors. *J. of Virol.* 62: 776-782 (1988).

Mackett et al., Vaccinia Virus Expression Vectors. *J. Gen. Virol.* 67: 2067-2082 (1986).

Mackett et al., Vaccinia virus: A selectable eukaryotic cloning and expression vector. *Proc. Natl. Acad. Sci. USA* 79: 7415-7419 (1982).

McMillen et al., The Safe and Effective Use of Fowlpox Virus as a Vector for Poultry Vaccines. Brown F. (Ed): *Recombinant Vectors in Vaccine Development. Dev. Biol. Stand. Basel, Karger* 82: 137-145 (1994).

Merchlinsky et al., Introduction of Forein DNA into the Vaccinia Virus Genome by in Vitro Ligation: Recombination-Independent Selectable Cloning Vectors. *Virology* 190: 522-526 (1992).

Miner et al., DNA Sequences that Regulate Expression of a Vaccinia Virus Late Gene (L65) and Interact with a DNA-Binding Protein from Infected Cells. *J. of Virol.* 63: 2726-2736 (1989).

Miner et al., Vaccinia virus: a versatile tool for molecular biologists. *TIBTECH* 8: 20-25 (1990).

Moss, Replicating and Host-Restricted Non-Replicating Vaccinia Virus Vectors for Vaccine Development. Brown F. (Ed): *Recombinant Vectors in Vaccine Development. Dev. Biol. Stand. Basel, Karger* 82: 55-63 (1994).

Moss, Poxvirus Expression Vectors. *Curr. Topics in Microbiol. and Immunol.* 158: 25-38 (1992).

Ober et al., Immunogenicity and Safety of Defective Vaccinia Virus Lister: Comparison with Modified Vaccinia Virus Ankara. *J. of Virol.* 76: 7713-7723 (2002).

Panicali et al., Construction of poxviruses as cloning vectors: Insertion of the thymidine kinase gene from herpes simplex virus into the DNA of infectious vaccinia virus. *Proc. Natl. Acad. Sci. USA* 79: 4927-4931 (1982).

Perkus et al., Cloning and Expression of Foreign Genes in Vaccinia Virus, Using a Host Range Selection System. *J. of Virol.* 63: 3829-3836 (1989).

Ravanello et al., Conditional Lethal Expression of the Vaccinia Virus L1R Myristylated Protein Reveals a Role in Virion Assembly. *J. of Virol.* 68: 6401-6410 (1994).

Rodriguez et al., Regulated Expression of Nuclear Genes by T3 RNA Polymerase and *lac* Repressor, Using Recombinant Vaccinia Virus Vectors. *J. of Virol.* 64: 4851-4857 (1990).

Rodriguez et al., Plaque Size Phenotype as a Selectable Marker to Generate Vaccinia Virus Recombinants. *J. of Virol.* 63: 997-1001 (1989).

Rodriguez et al., Inducible Gene Expression from Vaccinia Virus Vectors. *Virology* 177: 239-250 (1990).

Rodriguez et al., IPTG-dependent vaccinia virus: identification of a virus protein enabling virion envelopment by Golgi membrane and egress. *Nucl. Acids Res.* 18: 5347-5351 (1990).

Rosales et al., A cellular factor is required for transcription of vaccinia viral intermediate-stage genes. *Proc. Natl. Acad. Sci. USA* 91: 3794-3798 (1994).

Sam et al., Expression of Poxvirus DNA in Coinfected Cells and Marker Rescue of Thermosensitive Mutants by Subgenomic Fragments of DNA. *Ann Virol.* (*Inst. Pasteur*) 132E: 135-150 (1981).

Shuman et al., Insertional mutagenesis of the vaccinia virus gene encoding a type I DNA topoisomerase: evidence that the gene is essential for virus growth. *Virology* 170: 302-306 (1989). Abstract Only.

Shuman et al., Insertional mutagenesis of the vaccinia virus gene encoding a type I DNA topoIsomerase: evidence that the gene is essential for virus growth. *Virology* 170: 302-306 (1989). Abstract Only.

Spehner et al., A Cowpox Virus Gene Required for Multiplication in Chinese Hamster Ovary Cells. *J. of Virol.* 62: 1297-1304 (1988).

Stuart et al., A Poxvirus-Encoded Uracil DNA Glycosylase is Essential for Virus Viability. *J. of Virol.* 67: 2503-2512 (1993).

Sugimoto et al., Characteristics of an attenuated vaccinia virus strain, LC16m0, and its recombinant virus vaccines. *Vaccine* 12: 675-681 (1994).

Sutter et al., Nonreplicating vaccinia vector efficiently expresses recombinant genes. *Proc. Natl. Acad. Sci. USA* 89: 10847-10851 (1992).

Sutter et al., Stable Expression of the Vaccinia Virus K1L Gene in Rabbit Cells Complements the Host Range Defect of a Vaccinia Virus Mutant. *J. of Virol.* 68: 4109-4116 (1994).

Tartaglia et al., Safety and Immunogenicity of Recombinants Based on the Genetically-Engineered Vaccinia Strain, NYVAC. Brown F. (Ed): *Recombinant Vectors in Vaccine Development. Dev. Biol. Stand. Basel. Karger* 82: 125-129 (1994).

Tartaglia et al., Protection of Cats against Feline Leukemia Virus by Vaccination with a Canarypox Virus Recombinant, ALVAC-FL. *J. of Virol.* 67: 2370-2375 (1993).

Taylor et al., Nonreplicating Viral Vectors as Potential Vaccines: Recombinant Canarypox Virus Expressing Measles Virus Fusion (F) and Hemagglutinin (HA) Glycoproteins. *Virology* 187: 321-328 (1992).

Taylor et al., Fowlpox virus as a vector in non-avian species. *Vaccine* 6: 466-468 (1988).

Traktman et al., Vaccinia Virus Encodes an Essential Gene with Strong Homology to Protein Kinases. *J. Biol. Chem.* 264: 24158-24161 (1989).

Vazquez et al., Identification of Functional Domains in the 14-Kilodalton Envelope Protein (A27L) of Vaccinia Virus. *J. of Virol.* 73: 9098-9109 (1999).

Weir et al., Use of a Bacterial Expression Vector to Identify the Gene Encoding a Major Core Protein of Vaccinia Virus. *J. of Virol.* 56: 534-540 (1985).

Weir et al., Determination of the Transcriptional Regulatory Region of a Vaccinia Virus Late Gene. *J. of Virol.* 61: 75-80 (1987).

Wittek et al., Mapping of a Gene Coding for a Major Late Structural Polypeptide on the Vaccinia Virus Genome. *J. of Virol.* 49: 371-378 (1984).

Zajac et al., The vaccinia virus J5L open reading frame encodes a polypeptide expressed late during infection and required for viral multiplication. *Virus Res.* 37: 163-173 (1995). Abstract Only.

Zhang et al., Immature Viral Envelope Formation is Interrupted at the Same Stage by *lac* Operator-Mediated Repression of the Vaccinia Virus D13L Gene and by the Drug Rifampicin. *Virology* 187: 643-653 (1992).

Zhang et al., Inducer-dependent conditional-lethal mutant animal viruses. *Proc. Natl. Acad. Sci. USA* 88: 1511-1515 (1991).

Zhang et al., Transcription of Viral Late Genes is Dependent on Expression of the Viral Intermediate Gene G8R in Cells Infected with an Inducible Conditional-Lethal Mutant Vaccinia Virus. *J. of Virol.* 66: 6470-6479 (1992).

Zhang et al., Vaccinia Virus Morphogenenis is Interrupted when Expression of the Gene Encoding an 11-Kilodalton Phosphorylated Protein is Prevented by the *Escherichia coli lac* Repressor. *J. of Virol.* 65: 6101-6110 (1991).

Zhang et al., Targeting of a Multicomponent Transcription Apparatus into Assembling Vaccinia Virus Particles Requires RAP94, an RNA Polymerase-Associated Protein. *J. of Virol.* 68: 1360-1370 (1994).

\* cited by examiner

Fig.3a.
5' GATCCACCATGACCATGATTA
    GTGGTACTGGTACTAATCTAG 5'
Fig.3b.
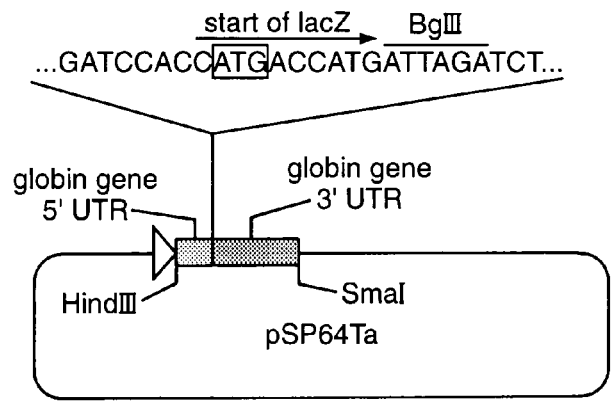
Fig.4a.
Upstream Primer
| HindIII | SmaI | CMV sequence |
5' ATCAAGCTTCCCGGGCCTGGCATTATGCCCAGTACATG
Downstream primer
| HindIII | CMV sequence |
5' TCAAAGCTTGAGCTCTGATTATATAGACCTCCC
Fig.4b.
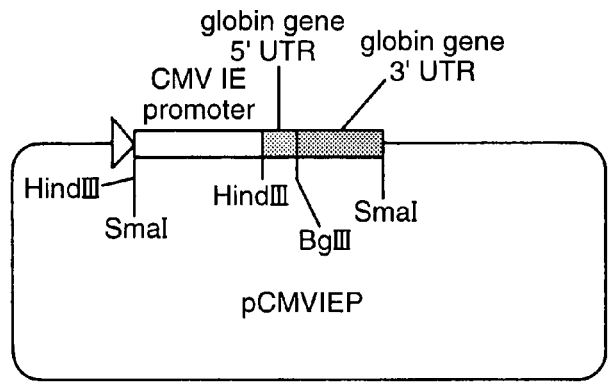

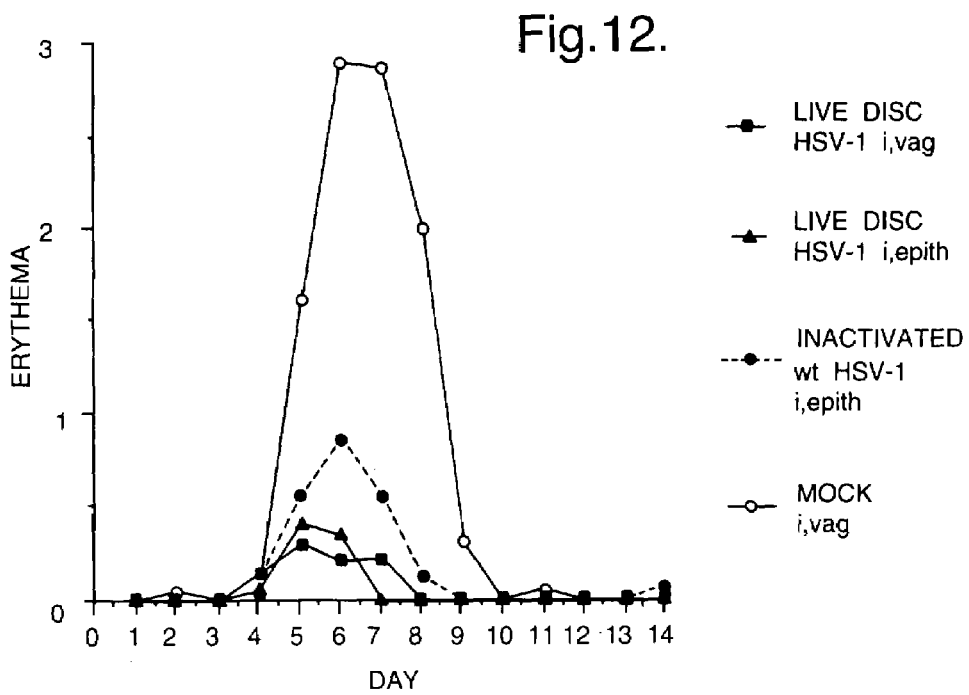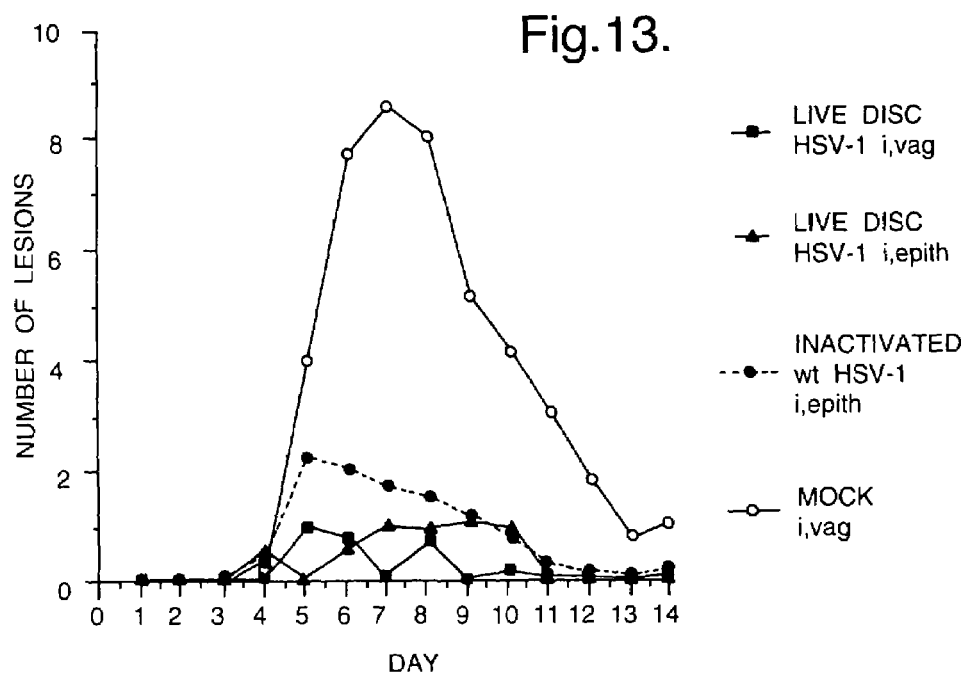

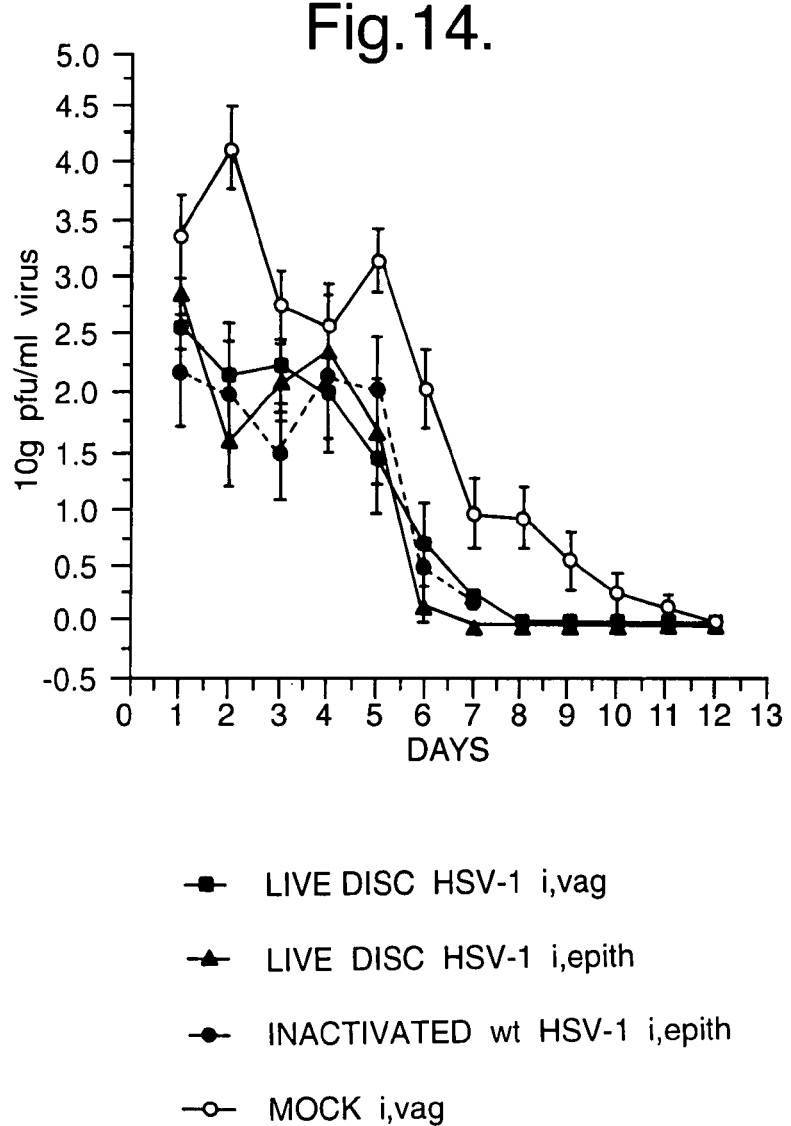

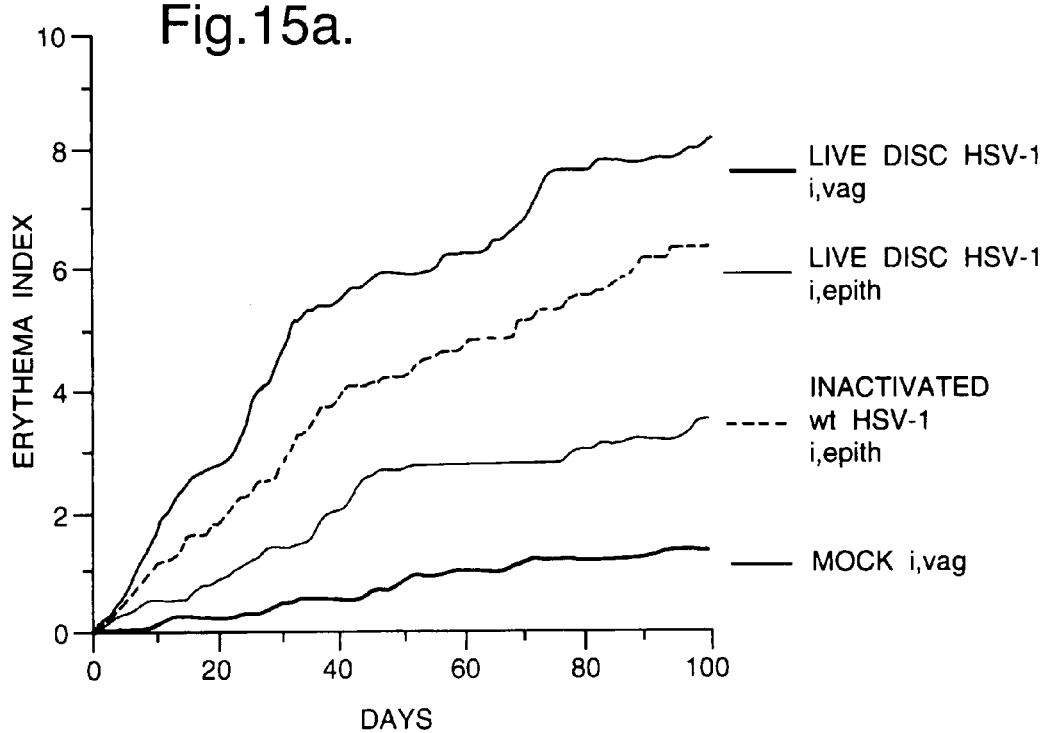
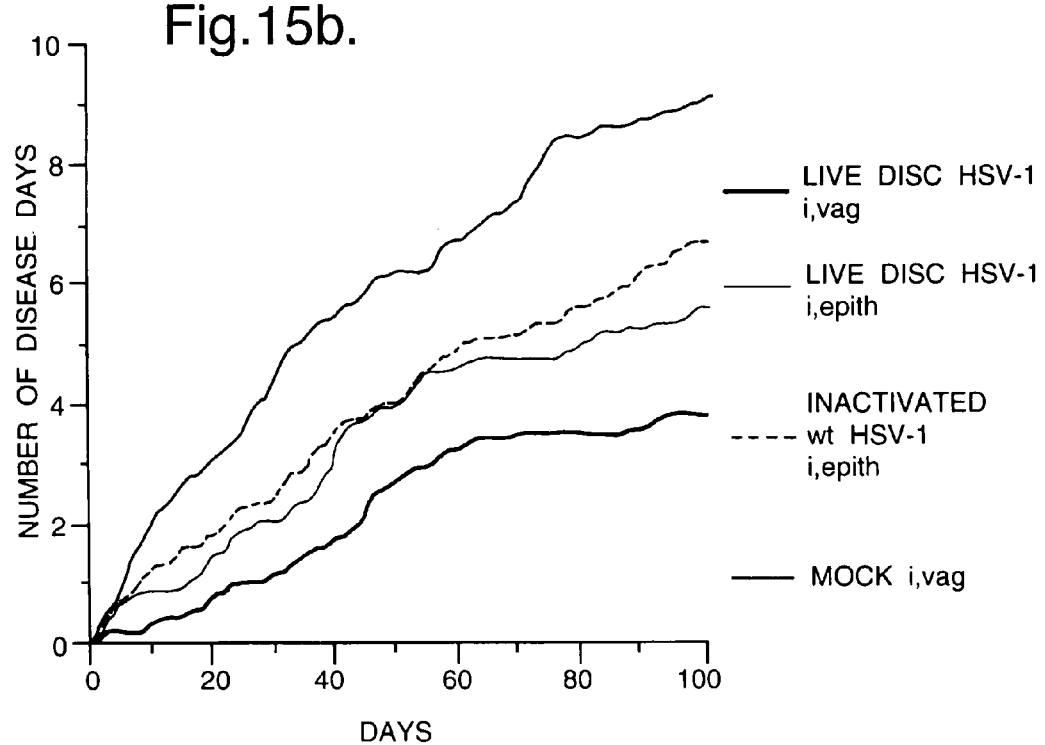

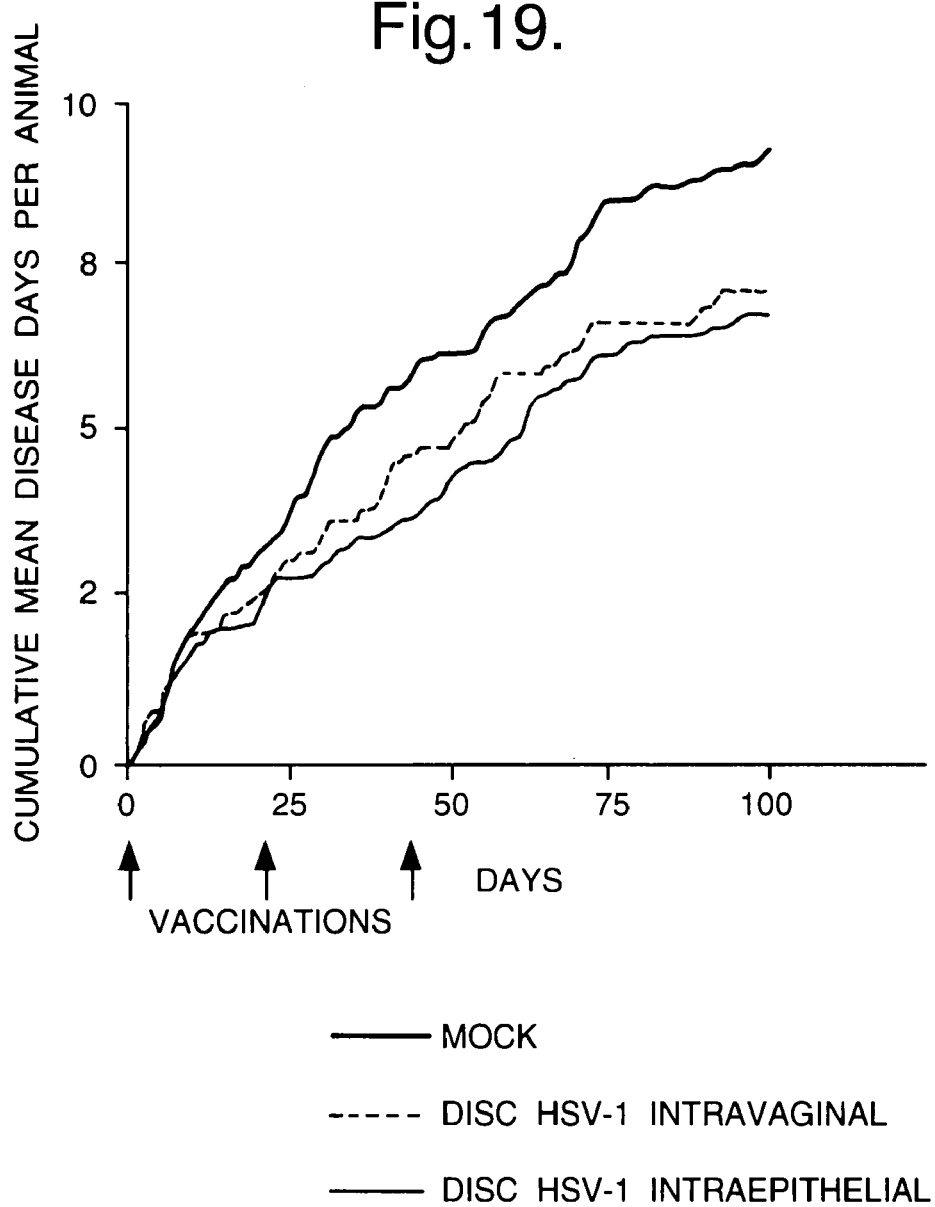

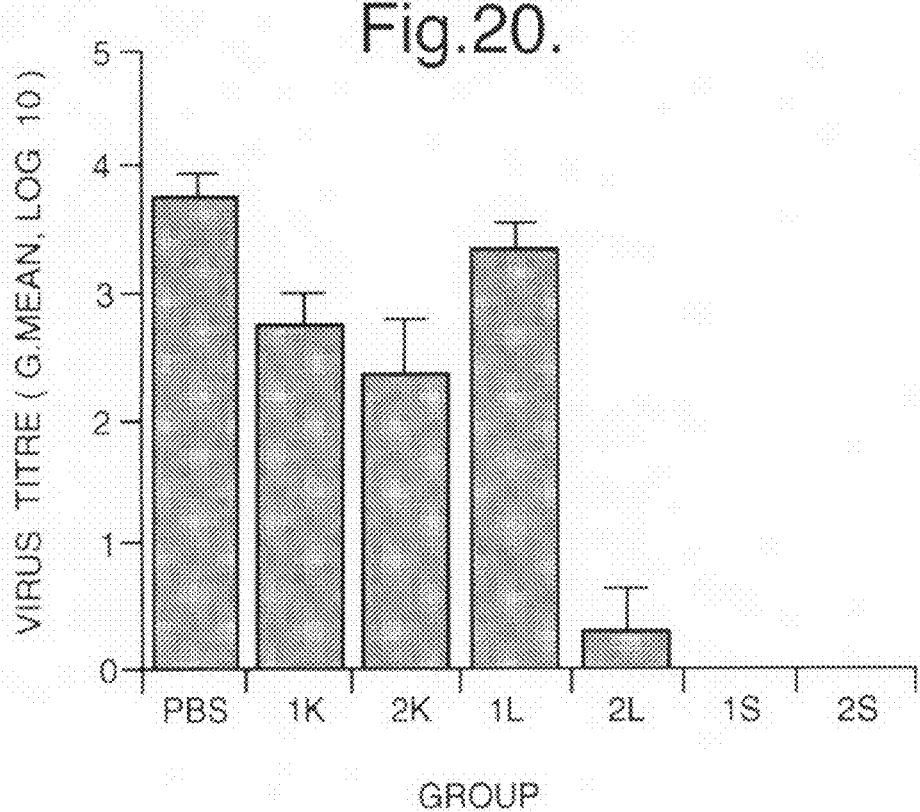

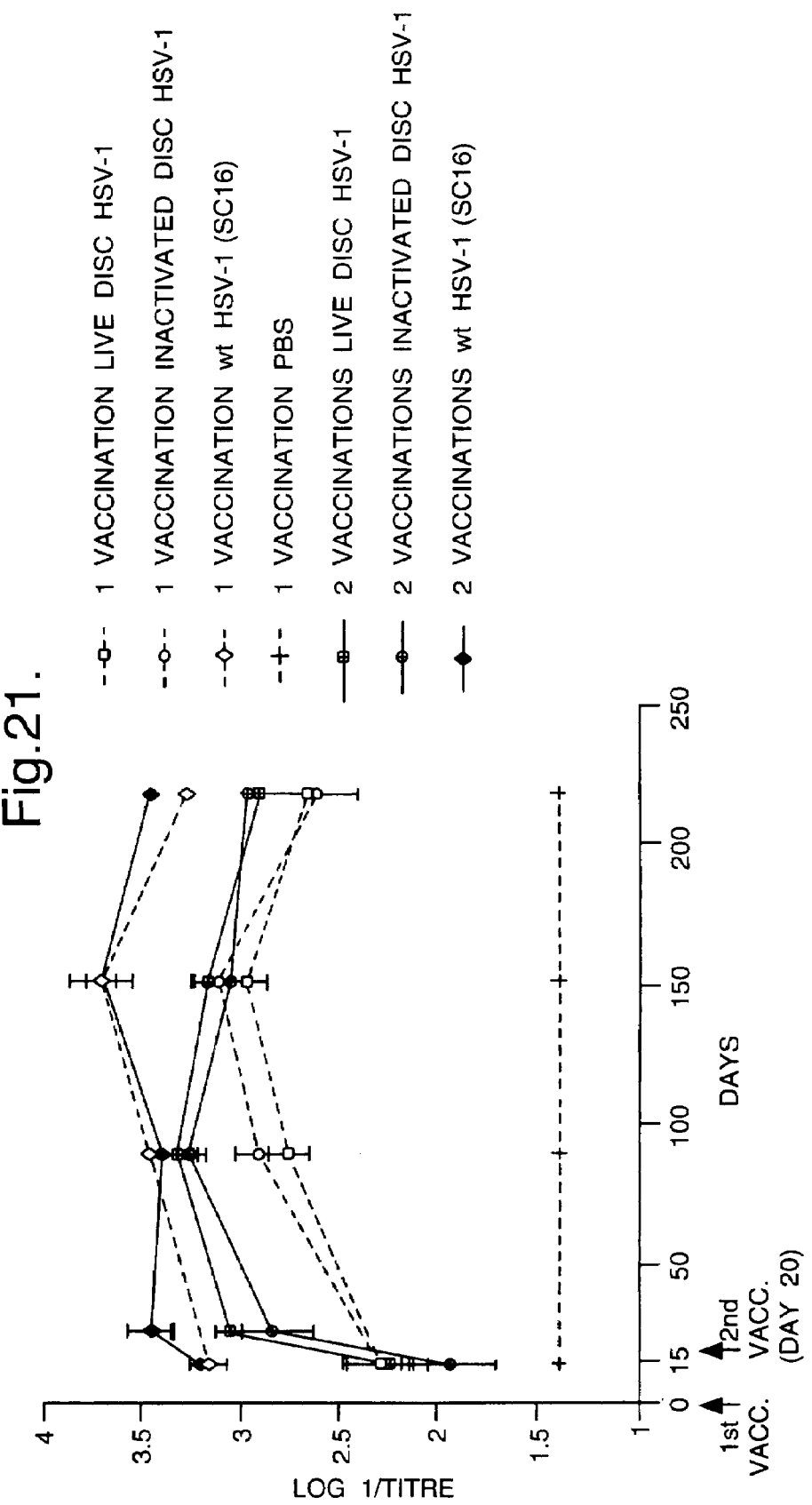

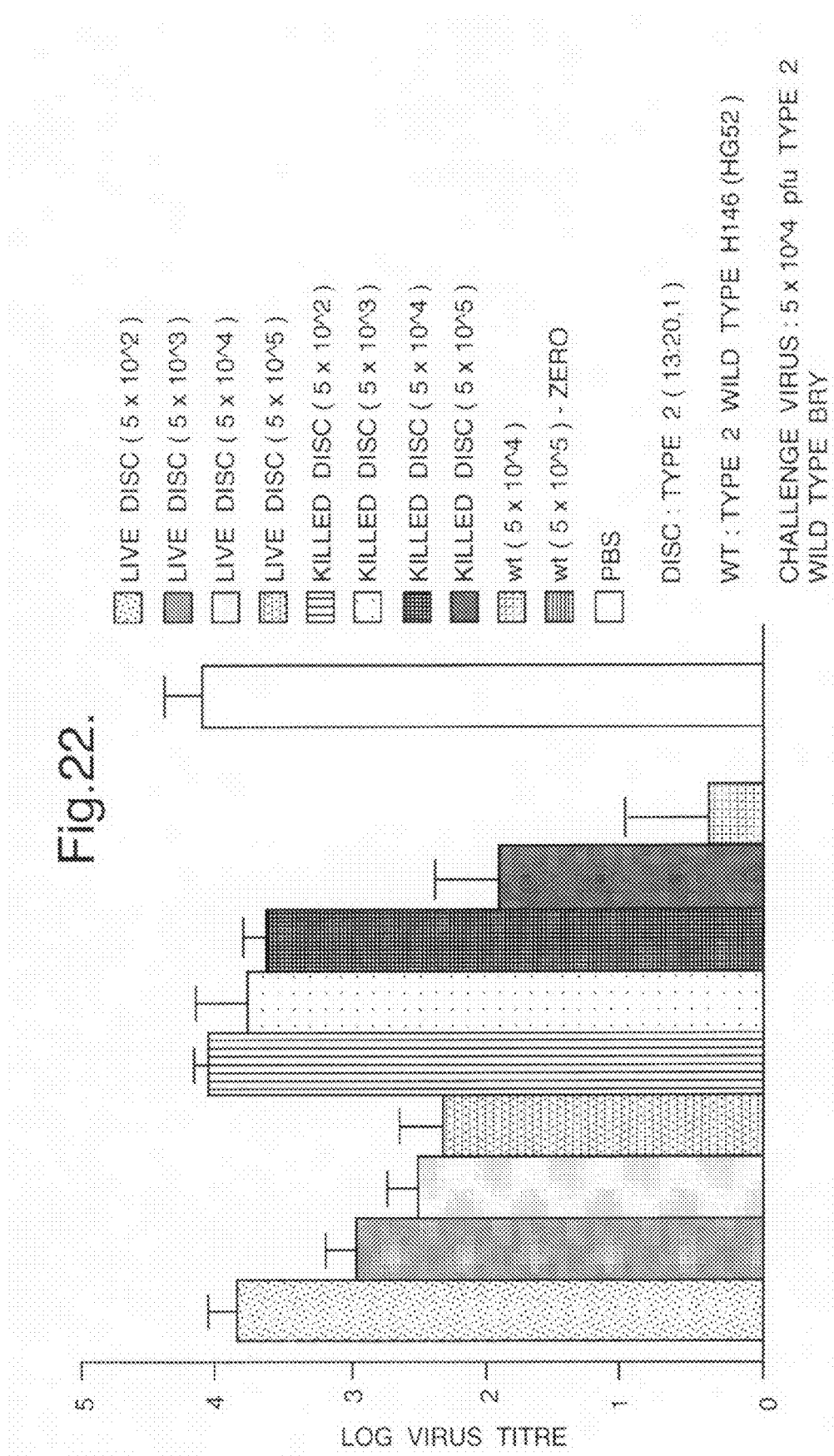

Fig. 24.

```
CTGCAGCGCGGCGGGAGGTGGCGGGAGGACTGGGGCCGGCTGACGGGGGTCGCCGCGGCG          60

ACCCCGCGCCCCGACCCCGAGGACGGCGCGGGGTCTCTGCCCCGCATCGAGGACACGCTG         120

TTTGCCCTGTTCCGCGTTCCCGAGCTGCTGGCCCCCAACGGGGACTTGTACCACATTTTT         180

GCCTGGGTCTTGGACGTCTTGGCCGACCGCCTCCTTCCGATGCATCTATTTGTCCTGGAT         240

TACGATCAGTCGCCCGTCGGGTGTCGAGACGCCCTGTTGCGCCTCACCGCCGGGATGATC         300

CCAACCCGCGTCACAACCGCCGGGTCCATCGCCGAGATACGCGACCTGGCGCGCACGTTT         360

GCCCGCGAGGTGGGGGGAGTTTAGTTCAAACACGGAAGCCCGAACGGAAGGCCTCCCGGC         420

GATGACGGCAATAAAAGAACAGAATAAAAGGCATTGTTGTCGTGTGGTGTGTCCATAAGC         480

GCGGGGGTTCGGGGCCAGGGCTGGCACCGTATCAGCACCCCACCGAAAAACGGAGCGGGC         540

CGATCCGTCCTTGTTTTCGGTCTGGTACTCCCTTTGTGCTTTTACCCTCACCCCACCCCA         600

TCCTTTGGCCCGCGCTTACGGCAACAAAGGGCCTCCGATAGCCTCCGAGGTGCGGACGCT         660

CTTTGGGCCGTGGGTACGGACACCCCCCCATCTGCGGACTGGCAGCCGGGACGACGACCA         720
                                                            M
TGGGCCCCGGTCTGTGGGTGGTGATGGGGGTCCTGGTGGNCGTTGCCGGGGGCCATGACA         780
 G  P  G  L  W  V  V  M  G  V  L  V  V  A  G  G  H  D  T
CGTACTGGACGGAGCAAATCGACCCGTGGTTTTTGCACGGTCTGGGGTTGGCCCGCACGT         840
  Y  W  T  E  Q  I  D  P  W  F  L  H  G  L  G  L  A  R  T
ACTGGCGCGACACAAACACCGGGCGTCTGTGGTTGCCCAACACCCCCGACGACCAGCGAC         900
 Y  W  R  D  T  N  T  G  R  L  W  L  P  N  T  P  D  D  Q  R  P
CCCCAGCGCGGACGCTTGGCGCCCCCGGGCAACTCAACCTGACTACGGCATCCGTGCCCA         960
   P  A  R  T  L  G  A  P  G  Q  L  N  L  T  T  A  S  V  P  M
TGCTTCGGTGGTACGCCGAGCGCTTTTGTTTCGTGTTGGTCACCACGGCCGAGTTTCCTC        1020
  L  R  W  Y  A  E  R  F  C  F  V  L  V  T  T  A  E  F  P  R
GGGACCCCGGGCAGCTGCTTTACATCCCAAAGACCTATCTGCTCGGCCGGCCTCGGAACG        1080
 D  P  G  Q  L  L  Y  I  P  K  T  Y  L  L  G  R  P  R  N  A
CGAGCCTGCCCGAGCTCCCCGAGGCGGGGCCCACGTCCCGTCCCCCCGCCGAGGTGACCC        1140
  S  L  P  E  L  P  E  A  G  P  T  S  R  P  P  A  E  V  T  Q
```

Fig.24 (Cont 1).

```
AGCTCAAGGGACTGCTGCACAACCCCGGCGCCTCCGCGATGTTGCGGTCCCGGGCCTGGG        1200
  L  K  G  L  L  H  N  P  G  A  S  A  M  L  R  S  R  A  W  V

TAACATTCGCGGCCGCGCCGGACCGCGAGGGGCTTACGTTNCCGCGGGGAGACGACGGGG        1260
  T  F  A  A  A  P  D  R  E  G  L  T  T  P  R  G  D  D  G  A

CGACCGAGAGGCACCCGGACGGCCGACGCAACGCGNCCCCGGGGCCGCCCGCGGGGGCGC       1320
  T  E  R  H  P  D  G  R  R  N  A  A  P  G  P  P  A  G  A  P

CGAGGCATCCGACGACGAACCTGAGCATCGCGCATCTGCACAACGCGTCCGTGANCCTGC       1380
  R  H  P  T  T  N  L  S  I  A  H  L  H  N  A  S  V  V  L  L

TGGCCGCCAGGGGCCTGCTACGGACTCCGGGTCGGTACGTGTACCTCTCCCCGTCGGCCT       1440
  A  A  R  G  L  L  R  T  P  G  R  Y  V  Y  L  S  P  S  A  S

CGACGTGGCCCGTGGGCGTCTGGACGACGGGCGGGCTGGCGTTCGGGTGCGACGCCGCGC       1500
  T  W  P  V  G  V  W  T  T  G  G  L  A  F  G  C  D  A  A  L

TCGTGCGCGCGCGATACGGGAAGGGCTTCATGGGGCTCGTGATATCGATGCGGGACAGCC       1560
  V  R  A  R  Y  G  K  G  F  M  G  L  V  I  S  M  R  D  S  P

CTCCGGCCGAGATCATAGTGGTGCCTGCGGACAAGACCCTCGCTCGGGTCGGAAATCCGA       1620
  P  A  E  I  I  V  V  P  A  D  K  T  L  A  R  V  G  N  P  T

CCGACGAAAACGCCCCGCGTGCTCCCCGCGCTCCGGCCGGCCCCAGGTATCGCGTCTTTG       1680
  D  E  N  A  P  R  A  P  R  A  P  A  G  P  R  Y  R  V  F  V

TCCTGGGGGCCCCGACGCCCGCCGACAACGGCNTCGGCGCTGGACCCCCTCGGCGGGTGG       1740
  L  G  A  P  T  P  A  D  N  G  G  A  G  P  P  R  R  V  A

CCGGCTACCCCGAGGAGAGCACGAACTACGCCCAGTATATGTCGCGGGCCTATGCGGAGT       1800
  G  Y  P  E  E  S  T  N  Y  A  Q  Y  M  S  R  A  Y  A  E  F

TTTTGGGGGAGGACCCGGGCTCCGGCACGGACGACGCGCGTCCGTCCCTGTTCTGGCGCC       1860
  L  G  E  D  P  G  S  G  T  D  D  A  R  P  S  L  F  W  R  L

TCGCGGGGCTGCTCGCCTCGTCGGGGTTTGCGTTCGTCAACGCGGCCCACGCCCACGACG       1920
  A  G  L  L  A  S  S  G  F  A  F  V  N  A  A  H  A  H  D  A

CGATTCGCCTCTCCGACCTGCTGGGTTTTTTGGCCCACTCGCGCGTGCTGGCCGGCCTGG       1980
  I  R  L  S  D  L  L  G  F  L  A  H  S  R  V  L  A  G  L  A

CCGCCCGGGGAGCAGCGGGCTGCGCGGCCGACTCGGTGTTCCTGAACGTGTCCGTGTTGG       2040
  A  R  G  A  A  G  C  A  A  D  S  V  F  L  N  V  S  V  L  D

ACCCGGCGGCCCGTCTGCGGCTGGAGGCGCGCCTCGGGCATCTGGTGGCCGCGATCCTCG       2100
  P  A  A  R  L  R  L  E  A  R  L  G  H  L  V  A  A  I  L  E

AGCGAGAGCAGAGCCTGGCGGCGCACGCGCTGGGCTATCAGCTGGCGTTCGTGTTGGACA       2160
  R  E  Q  S  L  A  A  H  A  L  G  Y  Q  L  A  F  V  L  D  S

GCCCCGCGGCCTATGGCGGGTTGGCCCCGAGCGCGGCCCGCCTGATCGACGCCCTTGTTA       2220
  P  A  A  Y  G  G  L  A  P  S  A  A  R  L  I  D  A  L  V  T

CCGCGCAGTTTCTCGGCGGCCGCGTAACCGCCCCGATGGTCCGCCGAGCGCTGTTTTACG       2280
  A  Q  F  L  G  G  R  V  T  A  P  M  V  R  R  A  L  F  Y  A

CCACGGCCGTCCTCCGGGCGCCGTTCCTGGCGGGCGTGCCCTCGGCCGGGCAGCGGGAAC       2340
  T  A  V  L  R  A  P  F  L  A  G  V  P  S  A  G  Q  R  E  R
```

Fig.24 (Cont 2).

```
GCCCGCGGGGCCTCCTCATAACCACGGCCCTGTGTACGTCCGACGTCGCCGCGGCGACCC          2400
  P  R  G  L  L  I  T  T  A  L  C  T  S  D  V  A  A  A  T  H

ACGCCGATCTCCGGGCCGCGCTACGCAGGACCGACCACCAGAAAAACCTCTTCTGGCTCC          2460
  A  D  L  R  A  A  L  R  R  T  D  H  Q  K  N  L  F  W  L  P

CGGACCACTTTTCCCCATGCGCACGTTCCCTGCCGTTCGATCTCGCCGAGGGCGGGTTCA          2520
  D  H  F  S  P  C  A  R  S  L  P  F  D  L  A  E  G  G  F  I

TCCTGGACGCGCTGGCCATGGCCACCCGATCCGACATCCCGGCGGACGTCATGGCACAAC          2580
  L  D  A  L  A  M  A  T  R  S  D  I  P  A  D  V  M  A  Q  Q

AGACCCGCGGCGTGGCCTCCGCTCTCACGCNCTGGGCGACTCACAACGCCCTGATCCGCG          2640
  T  R  G  V  A  S  A  L  T  T  W  A  T  H  N  A  L  I  R  A

CCTTCGTCCCGGAGGCCACCCACCAGTGTAGCGGCCCGTCGCACAACGNGGAGCCCCGGA          2700
  F  V  P  E  A  T  H  Q  C  S  G  P  S  H  N  N  E  P  R  I

TCCTCGTGCCCATCACCCACAACGCCAGCTACGTCGTCACCCACTACCCCCCTTGCCCCC          2760
  L  V  P  I  T  H  N  A  S  Y  V  V  T  H  Y  P  P  C  P  R

GCGGGATCGGATACAAGCTTACGGGCGTTGACGTCCGCCGCCCGCTGTTTATCACCTATC          2820
  G  I  G  Y  K  L  T  G  V  D  V  R  R  P  L  F  I  T  Y  L

TCACCGCCACCTGCGAAGGGCACGCGCGGGAGATTGAGCCGCCGCGGCTGGTGCGCACCG          2880
  T  A  T  C  E  G  H  A  R  E  I  E  P  P  R  L  V  R  T  E

AAAACCGGCGCGACCTCGGCCTCGTGGGGGCCGTGTTTCTGCGCTACACCCCGGCCGGGG          2940
  N  R  R  D  L  G  L  V  G  A  V  F  L  R  Y  T  P  A  G  E

AGGTCATGTCGGTGCTGCTGGTGGACACGGATGCCACCCAACAGCAGCTGGCCCAGGGGC          3000
  V  M  S  V  L  L  V  D  T  D  A  T  Q  Q  Q  L  A  Q  G  P

CGGTGGCGGGCACCCCGAACGTGTTTTCCAGCGACGTGCCGTCCGTGGCCCTGTTGTTGT          3060
  V  A  G  T  P  N  V  F  S  S  D  V  P  S  V  A  L  L  L  F

TCCCCAACGGAACTGTGATTCATCTGCTGGCCTTTGACACGCTGCCCATCGCCACCATCG          3120
  P  N  G  T  V  I  H  L  L  A  F  D  T  L  P  I  A  T  I  A

CCCCCGGGTTTCTGGCCGCGTCCGCGCTGGGGGTCGTTATGATTACCGCGGCCCTGGCGG          3180
  P  G  F  L  A  A  S  A  L  G  V  V  M  I  T  A  A  L  A  G

GCATCCTCAGGGTGGTCCGAACGTGCGTCCCATTTTTGTGGAGACGCGAATAAACGGGTG          3240
  I  L  R  V  V  R  T  C  V  P  F  L  W  R  R  E  *

TGTGGACGCAGCGGCGTCCAGCCCAACCCAACCGACTCCCTCCGTGTCCGCGGTCTGTTT          3300

GTTATTGTGTCCGCCGTGGCTCCGCTACCGCCTCTGTTCCTTTCCCTTCTCCATTCCTGT          3360

TTCCTTTCCTTCCCCCCCCCCCATAGTCCCCCGTATAGGCATACAACGGCATCCGTGGGT          3420
                            End of HSV2 UL21
TAGAAAACGACTGCACTTTATTGGGATATCTCACACAGACTGGCCGTGCTGGGCGCGAGC          3480
                          *  V  S  Q  G  H

CAGGCAAACGGTAAGCAGCGCGTCCAGGTACCCGGCGGTTCGCGTGCGGCCAGCCGCCCC          3540
```

Fig.24 (Cont 3).

```
CGCCGGCCCGCGGTCAAACGCGGACATCCGGTCGACGTCCCCCACGGTCAGGACCAGGGA        3600

CGTCACGCCCGTCAGGCGCNCGGTATGCGTGGCCGCGGCCAGGCGTCCGTGGCCGGCGTA        3660

CAACACGCCCAGGAACGCGCCGAGGTACATGACGTGCTCGGGCGAGACGGACCCCCCCGG        3720

GGTCAGGCGTTGCGAGTCCACAAAGCGCAGCAGGGCGGCGCTGTCGGCCCGCGACGTCGC        3780

TCCCCACCGGCACGTCCTTGGGCGGGAGGAGGTCGAACATGAGGAGCTGCTCGCGA            3840
```

Fig. 25.

```
  1 CTGCAGGGCGGCGGGTCGTGGCGGGAGGATTGGGGACAGCTTTCGGGGGCGGCCGTGCCGCCCCAGGTGCCGAGCCCCAGAGCAACGCGGGCCCACGAC  100
    |||||  |||||||    ||||||||     ||||||  |||   ||||   | ||| ||  ||||||||      | ||  ||||  |||||| |||
  1 CTGCAGCCGCCGCGGAGGTGCGGGAAGCTGGGGACTGGGGCTGCCGCCCCTGACGGCCGGCGCGCCCCGACCCCGAGGACGGCGCGGGGTCTCTGC  100
    Oligo MB59

101 CCCATATCGGGACACGTTATTACCCTGTTCGGGCCCCCCAAGCGGCGACCTGTATAACGTGTTTGCCTGGGCTTTGGACGTCTT  200
    ||| ||||| |||||  |||  |||  ||||||| |||||||| || ||||| ||| || ||  ||||||||||||||||||||
101 CCCGCATCGAGGACACGCTGTTTGCCCTGTTCCGCGTTCCGGAGCTGCTGGCCCCGCTGCCGGGGACTTGTACCACATTTTTGCCTGGGTCTTTGGACGTCTT  200

201 GGCCAAACGCCTCCGTCCCATGCATGCTCTTTATCCTGGATTACGACCAATCGCCCGGCCTGCCGGGACGCCCTGCTGCAACTTACCTCCGGATGGTC  300
    |||| |||| |||  |||   || ||  ||   |  |||  ||||||| |||| |  ||||||| | |||| || || |||  |   |||||| ||
201 GGCCGACCGCTCCTTCCGATGCATGATCTATTGTCCTGGATTACGACGACAGTCGCCTGTTGCGGGCTGTCGAGAACGCGCCTGTTGCGCCTCACCGCCGGGATGATC  300

.End of HSV1 TK
301 CAGACCCACGTCACCACCCAGGCTCCATACCGACGATCTGCGACCTGGCGCACGTTTGCCCGGGAGAT.GGGGGAGGCTAACTGAAACACGAAGGA  399
    |  |||| |||     |||||   || |||   |||   |   |  |||||||| ||||| |     |||||||||||||| ||||||||||||
301 CCAACCCGCGTCACAACCGCGGGTCCATCGCAGATACGCGAGATACGGCCGGTCCGCACGTTTGCCCGAGGTGGGGGAGTTTAGTTCAAACACGAAG..  398
                                                                              End of HSV2 TK

400 GACAATACCGGAAGGAACCCGCGCTATGACGGCAATAAAAAGACAGAATAAAAACGACACGGGTGTTGGGTCGTTTGTTCATAAACGC..GGGGTTCGGTTCCC  498
    ||||||||| ||    ||| | || | |  ||||||||||||   |||   ||||   |||  ||   |||||| |||| ||||||    |||||||| ||
399 .CCGAACGGAAGGCCTCCCGGATGACGACGAGCAATAAACAGAACAGAATAAAAGGCATTGTGTCGTGTGGTGTCCATAAGCGCCGGGGGTTCGGGGCC  496

499 AGGGCTGGCACTCTGTCGATATCCAGCAGACCACCCGAAAAACGGAGCGGGCCGATCCGTCCTTGTTTTCGGTCTGGTACTCCCTTTGTGCTTTTACCCCTCACCCCAC  573
    |||  ||||||||||  ||||  ||||||||| || |||| ||||||| |||  ||| |  |||   |  || | | ||||  ||||| ||||  |  |||| ||  
497 AGGGCTGGCACCGGTATCAGCAGCACCCCGAAAAAACGGAGCGGGCCGATCCGTCCTTGTTTTCGGTCTGGTACTCCCTTTGTGCTTTTACCCTCACCCCAC  596

574 CCCAACC......................CCCAAGTTCGGTGGTGAAGGCCAACGTCGGGGGCGGCCAACGTCGGGGGGCGGCCAACGCGCCACGGGCCCC  653
    |||||  |                       | |||  |  | |                 ||||  ||| |   ||| | |   |   ||       ||
597 CCCATCCTTGGCCCGCGCTTACGGCAACAAAGGGCCCTCCGATAGCCTCCGAGGTGCGACGCTCTTTGGGCCGTGGGTACGACACCCCCATCTGCG  696

Start of HSV1 gH
654 GTGGGTTAGGGACGGGTCCCCCATGGGAATGGTTTATGGTTCGTGTGGGGTTATTATTTTGGGCGTTGCGTGGGTCAGGTCCACGACTGGACTGAGCA  753
    |||  ||| |   ||   ||||||| | ||| ||||  | || || |||    |||||||   || |||||  | ||| ||  |||   |||||||
697 GACTGCAGCCGGACGACGAGCAGACTGGGCCCGGTTCTGTGGGTGGTGATGGGGGTCGTGTGGGCCATGACGTTGCCGGGGCCATGACGTACTGGACGGAGCA  796
    Oligo MB75  Start of HSV2 gH 754 GACAGACCCATGTTTTTGGATGGCCTGGGCATGACGGCCATGTACTGCGCGACGAACACCGGCGTCTGTGCTGCCAAACACCCCGACCCCCAA  853
    | ||||||||| ||||||||| |||||| |||  ||||| ||| |||  |||| |||| |||   ||||| |||| |||||||||| ||   |||
797 AATCGACCCCGTGGTTTTTGCACGGTCTGCGGGGTTGCACGGTGCCGCCGACACTGGCGCGACAAAACACCGGCGACACTGGCGTTGCCCAACACCCCGACGACCAG  896
```

Fig.25 (Cont 1).

```
 854 AAACCACC.GCGCGGATTTCTGGCGCCGCCGGACGAACTAAACCTGACTACGGCCATCTCTGCCCCTTCTTCGCTGGTACGAGGAGCGCTTTGTTTTGTA  952
          ||| || |||||||        |||||||||  |  |||| |||| || |  |||||  ||||| |  |||||||  |||||||   |||||||||||
 897 CGACCCCCAGCGCGGACGCTTGGCGCCCCCCGGGC..AACTCAACCTGACTACGGCCATCCGTGCCCATGCTTCGGTGTACGGCGAGCGCTTTGTTTCGTG  995

953 TTGGTCACCACGGCCGAGTTTCCGGGACCCCGGGCCAGCTGCTTTACATCCGAAGACCTACCTGCTCGGCCGCCGCCCCCCGAACGCGAGCCTGCCCGCCC  1052
     |||||||||||||  |||||| ||||||||||||||||||||| |||||||||||||||| |||||||||||  | |||||||| ||||||||||| ||
 996 TTGGTCACCACGGCCGAGTTTCCTCGGACCCCGGGCCAGCTGCTTTACATCCAAAGACCTATCTGCTCGGCCGCTCGGAACGCGAGCCTGCCCGAGC     1095

1053 CCACCACGGTCGAGCGACGCGACCGCCCCCCCCTCGGTCGCGCCAGCCTCTCTTGCACAATCCAGCCGCCTCCGTGTGCTGCTTCCGGGC             1152
     |  || |  ||||||| ||   |||  ||  ||| | ||||||||  | || ||  || ||| ||||| |||| |||||| |  |||||
1096 TCCCCGAGGCGGGGCCCACGTCCCCGTCCCCCCCGAGGTGACCCAGTCTGCACAAGGACTCAAGGAGACTGCTGCACAACCCGGATGTTGCGGTCCCGGGC  1195

1153 CTGGGTAACGTTTCGGCCGTCCCTGACCCCGAGGCCTCCGGCGGCACCCGAGACAACGTGGCGACGGAGAGCGAGCGGCCGCGTGAGCCGCGTGATACA   1252
     |||||||||  ||| ||||| ||||||||| | ||   |||   ||||  |||  |||  || |||  |  |||||| ||:|||  ||||
1196 CTGGGTAACATTCGCGGCCGAGCTTACGTTNCCGGACCCGAGGCATCCGACGAACCTGAGCATCTGCACAAGAGGACACCCGGACGACCGGCGACG...CAAC 1292

1253 CCGCCCCCCGACGGCCGGTTGGGCGGCCACCCGAGCGGAGCTGGACATCACGGACCTGCACAACGCGTCACGACCTGGTTGGCCACCCGG            1352
     ||: |||                                  ||      ||                      |  | |||| ||||| |||
1293 GCGNCCCGGGGCGCCGCCGGAGTCGGTACCTGCTTCGGGCCAGGGCATCAGTATCTGAACCTGCACAACGCGTCCGGAGGTGCTGGTCTGGGTGCGA    1392

1353 GCCTGTTGAGATCCCAGGTAGGTACGTGTATTCTCCCCGTGGGCCTCGACGTCGGCATCTGAACGCGGGAGCTGGTCGTCGGGTGCCA              1452
     ||||||  |    ||                           |||||||  ||||||  ||||||||||  |||
1393 GCCTGCTACGGACTCCGGGTCGGTACGTGTACCTCTCCCCGTCGGCCTCGACGACGGCTGACGCGCGGGGCGGGCCGGTTCGGGTGCGA              1492

1453 TGCCCGCTGGTGCGCGCGACGGGCGGGAATTCATGGGCTCGTGATATCCATGCACGACAGCCCTCCGGTGGAAGTGATGGTGGTCCCCGGGGC          1552
     | ||||  ||||||||||||||| ||   |||||||    ||    |||||||||||    |||||    || |||     |||| ||
1493 CGCCCGGCTCGTGCGCGCGGATACGGGAAGGGCTTCATGGGCCGAAGCCGAGATCATGATGCGGGGACAGCCCTCCGGGCGGACAGCCTGCCGAC        1592

1553 CAGAGCGCTAGATCGGTCGGGGACCCCGCGCGACGAAAACCCCCCGGGCTCTTCCCGGGAAACCCCC...TGATCGGGTCTTTGTCCTAGGGT          1652
     |||| || | |    ||||| |  ||   ||   |||||     |||   |||||||  ||||      ||||||| ||||||||||||||
1593 AAGACCCCTGCCTCGGGTCGGAATCCGACCGACGAAAAACGCGCCCCGCGCGTGC...TCCCCGCGCTCCCGGCTCCGGCCGCCCCCAGGTATCGCGTCTTGTCCTCTGGGG 1689

1653 CCCCTGACGCGGGGCCCGACAACGCTCCGCGGGCTGACGCGGCGCTACCCGGAGGAGGGCACGAACTACGCCCAGTTCCTGTCGCGGGC            1752
     |||||||||   |    ||     |||   ::| ||                |||| ||||| || |||| ||||||| || ||||||
1690 CCCCGACGCGCCGCCGACAACGGNTCGGCGCGCTGGACCCCGCGCTACCCCCGGAGGAGCGCCGAACTACGAACTACGCCCAGTATGTCGCGGGC       1789

1753 ATACGCGGAGTTTTCTCGGGGGACGCGGGCCGCG...AGCAGGGCCCCGACGCGGCTCGGGCGCCTAACGGGGCTGTCGGACGTCGGGTTTT         1849
     |||||||||||||||  | || |||| ||   |||              |||||||||||||||| ||||| ||  |||||||||||||
1790 CTATGCGGAGTTTTTGGGGGAGGAGGACCCGCGAGCACCCGACGACGACGGCTCGGGCTCGGGGCGCTGCTCGGACTTCTCGCCTCGTCGTGGGGTTT    1889
```

Fig.25 (Cont 2).

```
1850 GCTTTCGTGAACGCGCCACCCAAACGGGCGGTCTGCCTCTCCGACCTGCTAGGCTTTTGCCCACTCGCGCGCGCTTGCCGCGGTTGGCCGCCCCGCG 1949
     ||  |  ||||||  ||||||||||  |||   ||  ||||||  ||||||   ||||||||||||| ||  ||||  |||||| ||  ||||||
1890 GCGTTCGTCAACGGGCCCACGCCCACGACGCGATTCGCCCTCTCCGACCTGCTGGGTTTTTTGGCCCACTCGCGCCGCTGCCGGCCCTGCCGCCCCGGG 1989

1950 GGGCCCGCGGGCTGTGCCGCGGATTCTGTGTTTTTTAATGTGTCAGTCTTGACTCCCACGGCCCCGCCTGCAGCTAGAGAGCTCGGCTCCAGCACCTGGTGGC 2049
     |||||||||||||| |||||||| || || |||||   |||||||||||| ||||| |||||||||||  ||  ||||||||||||||||| ||||||||
1990 GAGCAGCGGGGCTGCGCGGCCGACTCGGTGTTCCGTGAACGTGTCCGTGTTGGACCCGGCGGCCCGTCTGCGCGCTGGAGGGCGCCTCGGGCATCTGGTGGC 2089

2050 CGAGATTCTGGAGGCGCGAACAGAGCTTGGCATTACACGCGCTGGGCTATCAGCTGGCTGCCTTCGTGCTGGATAGCCCCTCGGCGTACGACGCAGTGGCGCCC 2149
     |||||||||||||| ||||| |||||||| |||   ||||||||||||||||||||||||||||||||||||||||||  ||||  ||||| ||||||||
2090 CGCGATCCTCGAGCGAGAGCAGAGCGCACTGGCGCGCGCACGCGCTGGGCTATCAGCTGGCTGCCGTTCGTGTTGGACAGCCCCTATGCGGGTTGGCCCCG 2189

2150 AGCGCAGCCCATCTCATCGACGCCCTGTATGCCGAGTTTCTAGGGGCCGCGTGCTGACCACCCCGGTCGTCCACCGGGCGCTATTTTACGCCTCGGCTG 2249
     |||||||||||||||  ||||||||||||||||||| |||| |||   | ||| ||||| ||||||    |||||||    | ||||||||||||||
2190 AGCGCGGCCCCGCCCTGATCGACGCCCTTGTTACCGCGAGTTTCTCGGCGCGCCCGATGGTCCGCCCGAGCGCGTGTTTTACGCCACGGCCG 2289

2250 TCCTCCGGCAGCCGTTCTTGGCTCCCCTCGGCGTCTGCGTCGGCGTGCAGCGGGAACGCGCCCGAGCCTTCTGATAGCCTGTACGTCCGACGT 2349
     ||||||||||||   ||||||||||||||||||||||||||||||||||| ||                || |||| ||||| ||||||||
2290 TCCTCCGGGCGCCGTTCCTGGCGGCCGTGCCGGCGGTCCGCGCGGCCCGCGGCAGCGGGAACG...CCCGGGGGCCTCCTCATAACCACGGCCCCGTGTACGTCCGACGT 2386

2350 CGGCCGCAGCGACCAACGCCGACCTCCGGACCGCGCTGGCCCTGCGGGCCCGACCACTTTCGCCATGCGGCCC 2449
     |||||||||||||||||||||| |||| ||||||||||||||||||| ||||||||||| ||||||||| ||
2387 CGCCGCGGCGACCACGCCGACCGCCGATTCCGGACCGCGCTGGCCCCGGGCCCGACCACTTTTCCCCATGCGGCAGT 2486

2450 TCCCTGCGCTTTGATCTAGACGAGAGCCGTGTTTATCCTGGACGCGCTGGCTCAAGCCACCCGGTCGAAGTCCTGGCCCAGCAGACCC 2549
     ||||||||| |||||||| || ||||  ||||| |||||||||||||||||||| ||  |||||||||||||||||||||||||||
2487 TCCCTGCCGTTCGATCTCGCCGAGGGCCGGTTCATCCTGGAACGCGCTGGCCATGCCACATCCCGGCCGACTCCCGGACGTCATGCGGAGCACAACAGACCC 2586

2550 ACGGCCTCGCCTCGACCCTGACGCGTTGGGCACACTACAACGCCCTGATCCGCCCTCGTCCCTGAGGCCTCACATCGGTGCGGGGCCAGTCTGCCAA 2649
     ||||||||||||||||  || ||| ||| |||  ||                ||  |||||||||  |||      |||||| |||||||||||||
2587 GCGGCGTGGCCTCCGCTCTCACGCNCTGGGCGACTCACAACGCCCGTCACAACGCCCTCGATCCGCCCCTCGTCCCGGAGGCCACCACCAGTGTAGCGGCCCGTCGCACAA 2686

2650 CGTCGAGCCACGGATCCTGCGTACCCATCACCCCACAAACGCCAGCTACGTCGTCACCCACT...CCCCCTCTGCCCCGGGGATCGGCTACAAGCTCACCGGC 2746
     ||  ||||||||||  ||| ||  ||| ||||||||||||||||||| ||||||| || |||              ||||  |||||||||||| |||
2687 CGNGGAGCCCCGGATCCTCGCCCATCACCCCACAACGCCAGCTACGTCGTCACCCACAACGCCCACTACCCCCCCTTGCCCCGGGATCGGGATCGGATACAAGCTTACGGGC 2786

2747 GTCGACGTCCGACGCCCACTGTTCCTAACCTCACCGCGAAGGCTCACCGCGACATGCGAAAGCTCCACCGCGGATATCGAGTCCAGCCAAAACC 2846
     || ||||||||||||||||||| ||| |||| ||||||  |||||||||||||| ||    ||||||| | ||    ||||||  ||| | ||
2787 GTTGACGTCCGCGCCCGCCTGTTTTATCACCACTATCTCACCGCCACCTGCGAAGGGCACGCGCGCGGCACCGGGCGAGATTGAGCCGCGGGCGCCCTGGCGCGCCCCGAAAACC 2886
```

Fig.25 (Cont 3).

```
2847 AGCGCGACCTGGGGCTCGTGGGGGCCGTGTTTATGCGCTACACCCCGGCCGGGAGGTCATGTCTGTGTTGCTGGTGGATACGGACAACACACAGCAGCA 2946
     ||||||||| || |||||||||| || ||||||||||||||||||||||||| ||||||||| ||| ||||| ||  |||| || ||| || |||||
2887 GGGCGCGACCCTCGTGGGGGCCTCGTGTTTCGCGCTACACCCCGGCCGTGTTTCCGCGCTACACGGGAGGTCATGTCCGCGCTGGTGGACACCAACAGCA 2986
                                                                                                      .
2947 AATCGCCGCCCGGCCGGACGGAGGGGCGCCCCAAGCGTGTTTCGAGCGACGTGCCGCCTTGTTGCTATTTCCAAACGGAACCGTCATTCATTTG 3046
     | ||| ||||| ||  |  |||||| |||||||||| |||  |||||||| |||||||| |||| || ||||||||||||||||||||| ||
2987 GCTGGCCCAGGGCCGGTGCGGGCACCCCGAACGTGTTTTCCAGCGACGTGTTTGCGCCGCTGCCGCCCTGTTGTTGTCCCCAACGGAACTGTGATTCATCTG 3086
                                                                                                      .
3047 CTAGCCTTTGACACGCAGCCCGTGGCCGCCCGCAATTGCGCCCGGGTTTCTGCCGCGCCCTCTGGGCGTGGTTTATGATTACCGCCTGGCTGGCATCC 3146
     ||  |||||||||||    ||| |||  || ||| || ||||| ||||||||| ||| |||||  |||||| |||||||||||| |||||||| ||
3087 CTGGCCTTTGACACGCTGCCGCCCATCGCCCCACCATCGCCCCCCGGGTTTCTGCCGTGGGGGCGTGTTATGATTACCGGCCCTGGGGGCATCC 3186
                             End of HSV1 gH
3147 TAAAGGTTCTCCGGACAAGTGTCCCGTTTTTTTGGAGACGCGAATAAAGTGGGCGTTGGCCTTCGGCCTGTTTCTCCGCCCGACCGAATAAACTGTAACCGTG 3246
     |||| ||||  ||||  ||||  |||| || ||| ||  ||||| || |  ||| || || ||| ||  ||  |||   ||||||||  |||||||||
3187 TCAGGGTGGTCCGAACGTGCGTCCCATTTTTGTGGAGACGCGAATAAAACGGGTGTGTGACGCAGCGGCGTCCAGCCAACCCAACCGACTCCCCTCCGTG 3286
                             End of HSV2 gH                          Oligo MB61.
3247 TCTGTGGTTTGTTTGTTCAGGCCCCCGGTGGTCGTGCCGCTCTCCCCCCAGCC........CCTCTTTGCTTTCCCCTCCCCCC.......... 3314
     ||  ||| |   ||||   |  |||       |||     |||    |  |          |||  ||| |||  |||
3287 TCCGCGGTCTGTTTATTGTGTCCGCCGTGGCCTGCGCCGTCCGGCCTACCGCCCTCGTCCTTTCCCCTGTTTCCTTCCTTCCTTCCTTCCCCATAG 3386
                                                Oligo MB57
                                                                          End of HSV1 UL21
3315 .CCCCCGGAGAGGCGTCCATTGACACACAAGGGTGTAGTAGCGATATACGTTTATTGGGGTCTTTTACACAGACTGTCCGTGTTGGGAGCGAGCGAGACG 3413
     |||||| |||| || ||||| || ||||| |||||||   ||||    ||||| |  | ||| ||  |||||| ||| |||| | ||||||||| ||
3387 TCCCCCGTATAGGCATACAACGCATCCGTGGGTTAGAAAACGACTGCACTTTATTGGATATCTCACACAGACTGGCCGTGCGGCGAGCCAGGCA 3486
                                                                          End of HSV2 UL21
3414 AACGGTAAGAAGCACATCCAGGTACCCGGCCGGCGTGCCGGCTGCCCGCCCTCCCGGTCAAACGGGAAAGACGGTCCACGTCACCCACC 3513
     ||||||||| || || |||||||||||||||||| ||  ||  | |||||  ||| ||  ||||||  ||| |  ||||| |||  |
3487 AACGGTAAGCAGCGCGTCCAGTACCCGGCCGGTTCGCGTTGCGGCCAGCCGCCCGCGTCGACGACATCCGGTCAAACGCGACATCCCCCACG 3586
                                                                                              .
3514 GCTAGCACCAGGGAGGTCACCCTGTCAGCGACATGCCGGCTGCCTGGCGTGCGTTGCCGCCGGGCTACAGCACGCTCAGGAACGCACCAAGGT 3613
     ||    |||||||| ||||| ||  ||||  |   |||| ||||| ||| ||||:|||| || || ||||||:|||| |    || ||| ||
3587 GTCAGGACCAGGAGGACGTCACGCGTCAGGCCGCCCGTCAGGCGCCCGCCGTGGCCCGCCCAGGGCCTATGCGCCAGCGACACGCCGGCCGAGGT 3686
```

Fig.25 (Cont 4).

```
3614 ACGCGACGTGCTCGGGGAGATCACCCCCCGGGGACGGCGAGACGTTGCGATTCTATAAAGCGGACAGAGAGGCGGTGCTGTCGGCCTGC.ACGTCGCTTC 3712
      ||  ||||||||||  ||||       ||||  ||  |||||||  ||   |||||||||  || |||||||  || ||||||  || |||||||||
3687 ACATGACGTGCTCGGGCGAGACGACCCCCGG...GGTCAGGCGTTGCGAGTCCACAAAGCCAGCAGGGCGGCGCTGTCGGCCCCGGACGTCGCTCC 3783

3713 CCACCGGGCACGTCCTTTGGGGGAGAAGGTCGAACATGAGGAGCTGCTCG 3762
      ||||||||||||||  ||  ||||  || |||||||||||||||||||||
3784 CCACCGGGCACGTCCTTGGGCGGGAGGAGGAGGTCGAACATGAGGAGCTGCTCG 3833
                                        Oligo MB58
```

Fig.26.

```
  1 MGNGLWFVGVIILGVAWGQVHDWTEQTDPWFLDGLGMDRMYWRDTNTGRLWLPNTPDPQK  60
    ::  :::  :   .:  ::  :.    ::::  :::::  :::.  :  ::::::::::::::::  :.
  1 MGPGLW VVMGVLVVAGGHDTYWTEQIDPWFLHGLGLARTYWRDTNTGRLWLPNTPDDQR  59

61 PPRGFLAPPDELNLTTASLPLLRWYEERFCFVLVTTAEFPRDPGQLLYIPKTYLLGRPPN  120
    ::   :...:.:::::::.:.::::  ::::::::::::::::::::::::::::::::::  :
 60 PPARTLGAPGQLNLTTASVPMLRWYAERFCFVLVTTAEFPRDPGQLLYIPKTYLLGRPRN  119

121 ASLPAPTTVEPTAQPPPSVAPLKGLLHNPAASVLLRSRAWVTFSAVPDPEALTFPRGDNV  180
    ::::       .::   ::.  :   :::::::::.::   .:::::::::  :  ::  :..:  ::::..
120 ASLPELPEAGPTSRPPAEVTQLKGLLHNPGASAMLRSRAWVTFAAAPDREGLT PRGDDG  178

181 ATASHPSGPRDTPPPRPPVGARRHPTTELDITHLHNASTTWLATRGLLRSPGRYVYFSPS  240
    ::  ::   :  :..  :     ::  ::  :::::.:  :  ::::::  .::  :::::  :::::.:::
179 ATERHPDGRRNAPG  PPAGAPRHPTTNLSIAHLHNAS VLLAARGLLRTPGRYVYLSPS  235

241 ASTWPVGIWTTGELVLGCDAALVRARYGREFMGLVISMHDSPPVEVMVVPAGQTLDRVGD  300
    :::::::.:::::.:  ..::::::::::::..:::::::::::::.:::  :..:::::.  ::  :::.
236 ASTWPVGVWTTGGLAFGCDAALVRARYGKGFMGLVISMRDSPPAEIIVVPADKTLARVGN  295

301 PADENPPGALPGPPGGPRYRVFVLGSLTRADNGSALDALRRVGGYPEEGTNYAQFLSRAY  360
    :   :::.:  :  :   :..:::::::::::  :    :::::.:  ..  :::.:::::::::..:::::
296 PTDENAPRA PRAPAGPRYRVFVLGAPTPADNGGA GPPRRVAGYPEESTNYAQYMSRAY  353

361 AEFFSGDAG AEQGPRPPLFWRLTGLLATSGFAFVNAAHANGAVCLSDLLGFLAHSRALA  419
    :::,....:..   ....::   :::::  ::::   :::::::::::::..:.  :::::::::::::  ::
354 AEFLGEDPGSGTDDARPSLFWRLAGLLASSGFAFVNAAHAHDAIRLSDLLGFLAHSRVLA  413

420 GLAARGAAGCAADSVFFNVSVLDPTARLQLEARLQHLVAEILEREQSLALHALGYQLAFV  479
    ::::::::::::::::::.::::::::  :::  :::::  ::::  :::::::::::  ::::::::::
414 GLAARGAAGCAADSVFLNVSVLDPAARLRLEARLGHLVAAILEREQSLAAHALGYQLAFV  473

480 LDSPSAYDAVAPSAAHLIDALY AEFLGGRVLTTPVVHRALFYASAVLRQPFLAGVPSAV  538
    ::::  ::....:::::::.:::::    :.:::::::  :  :,.:::::::  ::::  ::::::::::
474 LDSPAAYGGLAPSAARLIDALVTAQFLGGRV TAPMVRRALFYATAVLRAPFLAGVPSAG  532

539 QRERARRSLLIASALCTSDVAAATNADLRTALARADHQKTLFWLPDHFSPCAASLRFDLD  598
    ::::.  :..:::  :::::::::::::.:::::  ::  :  ::::  :::::::::::  ::  :::
533 QRERP  RGLLITTALCTSDVAAATHADLRAALRRTDHQKNLFWLPDHFSPCARSLPFDLA  591

599 ESVFILDALAQATRSETPVEVLAQQTHGLASTLTRWAHYNALIRAFVPEASHRCGGQSAN  658
    :.  :::::::  : ..::::::  : .:.::::::::  ::::::: ::::::::::::  :  ::
592 EGGFILDALAMATRSDIPADVMAQQTRGVASALT WATHNALIRAFVPEATHQCSGPSHN  650

659 VEPRILVPITHNASYVVTH SPLPRGIGYKLTGVDVRRPLFLTYLTATCEGSTRDIESKR  717
    :::::::::::::::::::  :   :::::::::::::::::::::::::::::  :.::  :
651    EPRILVPITHNASYVVTHYPPCPRGIGYKLTGVDVRRPLFITYLTATCEGHAREIEPPR  709

718 LVRTQNQRDLGLVGAVFMRYTPAGEVMSVLLVDTDNTQQQIAAGPTEGAPSVFSSDVPST  777
    ::::  :::::::::::::::::  :::::::::::::::::::::.::  :  ::  ::::::::::
710 LVRTENRRDLGLVGAVFLRYTPAGEVMSVLLVDTDATQQQLAQGPVAGTPNVFSSDVPSV  769

778 ALLLFPNGTVIHLLAFDTQPVAAIAPGFLAASALGVVMITAALAGILKVLRTSVPFFWRR  837
    :::::::::::::::::::::::  :..:  ::::::::::::::::::::::::::::::  :..:::
770 ALLLFPNGTVIHLLAFDTLPIATIAPGFLAASALGVVMITAALAGILRVVRTCVPFLWRR  829
```

838 E 838
    :
830 E 830

VIRAL VACCINES

This application is a continuation-in-part of copending U.S. Ser. No. 08/384,963 filed 7 Feb. 1995, which is itself a continuation of U.S. Ser. No. 08/030,073, corresponding to International patent application PCT/GB91/01632, which was published on 2 Apr. 1992 as WO 92/05263, having an international filing date of 23 Sep. 1991 and entered into US national phase with serial number U.S. Ser. No. 08/030,073 and date 20 May 1993.

This application is also a continuation-in-part of copending U.S. Ser. No. 08/216,260 filed 21 Mar. 1994, which is itself a continuation-in-part of U.S. Ser. No. 08/168,643 filed 16 Dec. 1993. The specifications of the above-mentioned applications are hereby incorporated by reference.

The present invention relates to viral vaccines. In particular, it relates to genetically engineered mutant viruses for use as vaccines; to vaccines comprising the mutant viruses; recombinant cells; and to methods relating to the production of vaccines.

Viral vaccines are traditionally of two sorts. The first sort are 'killed' vaccines, which are virus preparations which have been killed by treatment with a suitable chemical such as beta-propiolactone. The second type are live 'attenuated' vaccines, which are viruses which have been rendered less pathogenic to the host, either by specific genetic manipulation of the virus genome, or, more usually, by passage in some type of tissue culture system. These two types of vaccine each have their own disadvantages.

Killed vaccines do not replicate in the host, and they must be administered by injection, and hence may generate an inappropriate kind of immune response. For example the Salk vaccine, a killed preparation of poliovirus, produces an immunoglobulin (Ig) G antibody response, but does not stimulate the production of IgA in the gut, the natural site of primary infection. Hence this vaccine, though it can protect the individual from the neurological complications of poliomyelitis, does not block primary infection, and so does not confer "herd immunity".

In addition, killed viruses do not enter and replicate inside host cells. Hence any beneficial immunological response to non-structural proteins produced during replication is not available. They also cannot stimulate the production of cytotoxic T cells directed against virus antigens. "Dead" antigens can be picked up by antigen presenting cells and presented to T cells. However, the presentation occurs via MHC Class II molecules and leads to stimulation of T helper cells. In turn, the T helper cells help B cells to produce specific antibody against the antigen. In order to stimulate the production of cytotoxic T cells, virus antigens must be processed through a particular pathway inside the infected cell, and presented as broken-up peptide fragments on MHC Class I molecules. This degradation pathway is thought to work most effectively for proteins that are synthesised inside the infected cell, and hence the only virus that enters host cells and expresses immunogenic viral protein is capable of generating virus-specific cytotoxic T cells. Therefore, killed vaccines are poor inducers of cellular immunity (cytotoxic T cells) against virus infection. From this point of view, live attenuated vaccines are more satisfactory.

Live attenuated viruses have been made hitherto by deleting an inessential gene or partly damaging one or more essential genes (in which case, the damage is such that the genes are still functional, but do not operate so effectively). However, live attenuated viruses often retain residual pathogenicity which can have a deleterious effect on the host. In addition, unless the attenuation is caused by a specific deletion, there remains the possibility of reversion to a more virulent form. Nevertheless, the fact that some viral protein production occurs in the host means that they are often more effective than killed vaccines which cannot produce such viral protein.

Live attenuated viruses, as well as being used as vaccines in their own right, can also be used as "vaccine vectors" for other genes, in other words carriers of genes from a second virus (or other pathogen) against which protection is required. Typically, members of the pox virus family, e.g. vaccinia virus, are used as vaccine vectors. When a virus is used as a vaccine vector, it is important that it causes no pathogenic effects. In other words it may need to be attenuated in the same way that a simple virus vaccine is attenuated. The same disadvantages as those described above therefore apply in this case.

It has been found possible to delete a gene (especially, an essential gene) from a viral genome and (also) provide a so-called "complementing" cell which provides the virus with the product of the deleted gene. This has been achieved for certain viruses, for example adenoviruses, herpesviruses and retroviruses. For adenoviruses, a human cell line was transformed with fragments of adenovirus type 5 DNA (F L Graham, J Smiley, W C Russell and R Nairn, J Gen Virol, 36 (1977) 59-72). The cell line expressed certain viral genes, and it was found that it could support the growth of virus mutants which had those genes deleted or inactivated (T Harrison, F Graham and J Williams, Virology 77 (1977), 319-329). Although the virus grew well on this cell line (the "complementing cell line") and produced standard viral particles, it could not grow at all on normal human cells. Cells expressing the T-antigen-encoding region of the SV40 virus genome (a papovavirus) have also been shown capable of supporting the replication of viruses specifically deleted in this region (Y Gluzman, Cell, 23 (1981), 182-195). For herpes simplex virus, cell lines expressing the gB glycoprotein (W Cai et al, J Virol 62 (1987), 714-721) the gD glycoprotein (M W Ligas and D C Johnson, J Virol 62 (1988) 1486-1494) and the Immediate Early protein ICP4 (N A Deluca et al, J Virol 56 (1985) 558-570) have been produced, and these have been shown capable of supporting the replication of viruses with specifically inactivated copies of the corresponding genes.

According to the present invention, there is provided a mutant virus for use as a vaccine, in which a viral gene encoding a protein which is essential for the production of infectious virus has been deleted or inactivated: and wherein said virus can be grown in a cell which has a heterologous nucleotide sequence which allows said cell to express the essential protein encoded by said deleted or inactivated viral gene. Such a mutant virus with a genome defective in respect of an essential gene can protect a susceptible species immunised therewith against infection by e.g. the corresponding wild-type virus. As discussed below, the mutant virus in such a vaccine can be infectious for cells of a susceptible species, e.g. a mammalian species, immunised therewith. Viral protein can thereby be expressed in the cells.

The present invention also provides a vaccine which comprises a virus as described above, together with one or more excipients and/or adjuvants. The viral genome may itself provide the immunogen. In certain embodiments it can contain genetic material such as a heterologous gene insert expressing an immunogenic protein, e.g. from a pathogen exogenous to the virus. In such a case exogenous immunogenic protein can be expressed in cells of a susceptible species immunised with the vaccine containing the mutant virus and infected by the mutant virus of the vaccine.

Immunity against the pathogen can thereby be conferred in a species normally susceptible to the pathogen. The exogenous protein can be from e.g. an immunodeficiency virus, and can be an immunodeficiency virus glycoprotein.

The mutant virus of the vaccine can be one that is capable in an infected species of establishing a latent infection with periodic reactivation. The mutant virus can be such that the defect in the essential gene allows the mutant virus still to infect normal cells and replicate therein to give rise to the production and release from the cells of non-infectious viral particles, but not to give rise to infectious viral particles.

The present invention also provides a complementing cell transfected with an attenuated virus as described above, for use in the preparation of a vaccine.

The present invention also provides a method which comprises the use of a virus as described above in the preparation of a vaccine for the therapeutic or prophylactic treatment of a disease, and for prophylactic or therapeutic use in generating an immune response in a subject infected therewith.

The present invention also provides a method for the production of a vaccine which comprises: culturing a cell infected with a virus having a deleted or inactivated viral gene encoding a protein which is essential for the production of infectious virus, and wherein the host cell has a heterologous nucleotide sequence comprising said viral gene and which is able to express the essential protein encoded by said gene; harvesting the viral thus produced, and using it in a vaccine.

The mutant can be from a double-stranded DNA virus, e.g. a herpesvirus, e.g. a herpes simplex virus (HSV). The mutant can be a type-1 HSV or a type-2 HSV. The defect can be in for example the glycoprotein gH gene.

It can be seen that the invention provides a mutant non-retroviral virus whose genome is defective in respect of a gene essential for the production of infectious virus, such that the virus can infect normal cells and undergo replication and expression of viral antigen genes in those cells but cannot produce normal infectious virus.

The applicants have termed the mutant viruses described herein DISC viruses (standing for 'defective infectious single cycle viruses') and an outline of the concept is illustrated in FIG. 35 of the accompanying drawings. Such DISC viruses can provide the sort of immune response traditionally obtainable from live virus vaccines, but without the deleterious side effects that live attenuated viruses pose, such as residual pathogenicity and reversion to virulence.

The virus may be derived from herpes simplex virus (HSV) in which, for example, the gene encoding glycoprotein H (gH) has been inactivated or deleted. The mutant virus may also comprise a heterologous sequence encoding an immunogen derived from a pathogen. The host cell will suitably be a recombinant eukaryotic cell line containing the gene encoding HSV glycoprotein H. As another example the virus may be derived from an orthopox virus, for example, vaccinia virus, which again may comprise a heterologous sequence encoding an immunogen derived from a pathogen.

The general teaching hereof may be exemplified by (i) the creation of a cell line expressing the HSV-1 gH glycoprotein gene (a gH+ complementing cell line): (ii) the production of HSV-1 virus with an interrupted gH gene (an HSV-1 gH– virus) and carrying a heterologous gene (beta-galactosidase); (iii) the growth of the HSV-1 gH– virus in the gH+ complementing cell line. It is shown herein that in experiments investigating the ability of HSV-1 gH-virus and killed HSV-1 to protect against infection with wild-type HSV-1, the HSV-1 gH-virus provided good protection.

The present application provides in certain examples mutant type-2 HSV (HSV-2 virus) for use as a vaccine, whose genome is defective in respect of a gene essential for the production of infectious HSV-2 such that the virus can infect normal cells and replicate therein to give rise to the production and release from the cells of non-infectious viral particles. The defect can be such that the gH gene encoding the gH protein which is essential for the production of infectious virus has been deleted or inactivated; this mutant HSV-2 defect allows the production and release from the cells of non-infectious virus particles. Such mutant HSV-2 virus can be grown in a cell which has a heterologous nucleotide sequence which allows said cell to express the essential gH protein encoded by said deleted or inactivated gH gene. Such mutant type-2 HSV can infect normal cells and undergo replication and expression of viral antigens in those cells but cannot produce normal infectious virus. Such mutant virus can be used prophylactically or therapeutically in generating an immune response in a subject infected with HSV eg with HSV-2.

This invention shows a unique way of combining the efficacy and safety of a killed vaccine with the extra immunological response induced by the in-vivo production of viral protein by the attenuated vaccine. In preferred embodiments it comprises two features. Firstly, a selected gene is inactivated within the virus genome, usually by creating a specific deletion. This gene will be involved in the production of infectious virus, but preferably not preventing replication of the viral genome. Thus the infected cell can produce more viral protein from the replicated genetic material, and in some cases new virus particles may be produced, but these would not be infectious. This means that the viral infection cannot spread from the site of the inoculation.

A second feature of the invention is a cell which provides the virus with the product of the deleted gene, thus making it possible to grow the virus in tissue culture. Hence, although the virus lacks a gene encoding an essential protein, if it is grown in the appropriate host cell, it will multiply and produce complete virus particles which are to outward appearances indistinguishable from the original virus. This mutant virus preparation is inactive in the sense that it has a defective genome and cannot produce infectious virus in a normal host, and so may be administered safely in the quantity required to generate directly a humoral response in the host. Thus, the mutant virus need not be infectious for the cells of the host to be protected and merely operates in much the same way as a conventional killed or attenuated virus vaccine. However, preferably the immunising virus is itself still infectious, in the sense that it can bind to a cell, enter it, and initiate the viral replication cycle and is therefore capable of initiating an infection within a host cell of the species to be protected, and producing therein some virus antigen. There is thus the additional opportunity to stimulate the cellular arm of the host immune system.

The deleted or inactivated gene is preferably one involved as late as possible in the viral cycle, so as to provide as many viral proteins as possible in vivo for generating an immunogenic response. For example, the gene may be one involved in packaging or some other post-replicative event, such as the gH glycoprotein of HSV. However, the selected gene may be one involved in the viral genome replication, and the range of proteins expressed in vivo will depend upon the stage at which that gene is normally expressed. In the case of human cytomegalovirus (HCMV) the selected gene may be one (other than the Immediate Early gene) that effectively prevents viral genome replication in vivo, since the Immediate Early gene which is produced prior to viral genome replication (and indeed is essential for it) is highly immunogenic.

This invention can be applied to any virus where one or more essential gene(s) can be identified and deleted from or inactivated within the virus genome. For DNA viruses, such as Adeno, Herpes, Papova, Papilloma and Parvo viruses, this can be achieved directly by (i) the in vitro manipulation of cloned DNA copies of the selected essential gene to create specific DNA changes; and (ii) re-introduction of the altered version into the virus genome through standard procedures or recombination and marker rescue. The invention however, is also applicable to RNA viruses. Techniques are now available which allow complementary DNA copies of a RNA virus genome to be manipulated in vitro by standard genetic techniques, and then converted to RNA by in vitro transcription. The resulting RNAs may then be re-introduced into the virus genome. The technique has been used to create specific changes in the genome of both positive and negative stranded RNA viruses, e.g. poliovirus (V R Racaniello and D Baltimore, Science 214 (1981) 916-919) and influenza virus (W Luytjes et al, Cell 59 (1989) 1107-1113).

In theory, any gene encoding an essential protein should be a potential target for this approach to the creation of attenuated viruses. In practice however, the selection of the gene will be driven by a number of considerations.

1. The gene should preferably be one which is required later in infection.

Thus replication of the attenuated virus is not interrupted in the early phase. This means that most and possibly all other virus antigens will be produced in the infected cell, and presented to the host immune system in conjunction with host cell MHC class 1 molecules. Such presentation leads to the development of cellular immunity against virus infection through the production of cytotoxic T cells. The cytotoxic T cells can recognise these antigens, and therefore kill virus infected cells. It is possible that the deleted gene could represent one which is not required at all for virus assembly, but is necessary for the assembled virus to be able to infect new cells. An example of such a protein is the HSV gH protein. In the absence of this protein, HSV virions are still produced, but they are non-infectious.

2. Ideally, the product of the selected gene should not, on its own, be toxic to the eukaryotic cell, so that a complementing cell can be produced relatively easily. This however is not an absolute requirement, since the gene may be placed under the control of an inducible promoter in the complementing cell, such that its expression may be switched on only when required.

The nature of the mutation created in the target gene is also a matter of choice. Any change which produces a non-functional gene product is satisfactory, as long as the risk of reversion of a wild type structure is minimised. Such changes include interruption of the target with extraneous sequences and creation of specific deletions. The most satisfactory strategy for a vaccine to be used as a therapeutic and/or prophylactic however, would be one where a deletion is made that encompasses the entire sequence to be introduced into the complementing cell. The approach minimises the risk of regenerating wild type virus through recombination between the virus and cell DNA in the complementing cell.

Although there are several examples of combinations of specifically inactivated viruses and complementing cells, (see earlier discussion), to date, these have been used either for basic research on the virus, or, as in the case of retroviruses, to make a safer vector for producing transgenic animals. They have not been used for vaccine purposes, and to the applicants knowledge no suggestion of this kind of use has been proposed.

As well as using such an inactivated virus/complementing cell combination to produce safe vaccines against the wild-type virus, this invention also deals with the use of the same system to produce safe viral vectors for use as vaccines against foreign pathogens.

An example of such a vector is one based on HSV. The HSV genome is large enough to accommodate considerable additional genetic information and several examples of recombinant HSV viruses carrying and expressing foreign genetic material have been described (e.g. M W Ligas and D C Johnson, J Virol 62 (1988) 1486-1494, op. cit.). Thus a virus with a deletion in an essential virus gene as described above, and also carrying out and expressing a defined foreign gene, could be used as a safe vector for vaccination to generate an immune response against the foreign protein.

A particular characteristic of HSV is that it may become latent in neurones of infected individuals, and occasionally reactivate leading to a local lesion. Thus an HSV with a deletion in an essential virus gene and expressing a foreign gene could be used to produce deliberately latent infection of neurones in the treated individual. Reactivation of such a latent infection would not lead to the production of a lesion, since the virus vector would be unable to replicate fully, but would result in the onset of the initial part of the virus replication cycle. During this time expression of the foreign antigen could occur, leading to the generation of immune response. In a situation where the deleted HSV gene specified a protein which was not needed for virus assembly, but only for infectivity or assembled virions, such a foreign antigen might be incorporated into the assembled virus particles, leading to enhancement of its immunogenic effect. This expression of the foreign gene and incorporation of its protein in a viral particle could of course also occur at the stage where the mutant virus is first produced in its complementing host, in which case the mutant virus when used as a vaccine could present immediately the foreign protein to the species being treated.

In another example, vaccinia virus, a poxvirus, can carry and express genes from various pathogens, and it has been demonstrated that these form effective vaccines when used in animal experimental systems. The potential for use in humans is vast, but because of the known side effects associated with the widespread use of vaccinia as a vaccine against smallpox, there is reluctance to use an unmodified vaccinia virus on a large scale in humans. There have been attempts to attenuate vaccinia virus by deleting non-essential genes such as the vaccinia growth factor gene (R M L Buller, S Chakrabarti, J A Cooper, D R Twardzik and B Moss, J Virology 62 (1988), 866-874). However, such attenuated viruses can still replicate in vivo, albeit at a reduced level. No vaccinia virus with a deletion in an essential gene has yet been produced, but such a virus, deleted in an essential gene as described above, with its complementing cell for growth, would provide a safer version of this vaccine vector.

A further advantage of this general strategy for immunisation against heterologous proteins is that it may be possible to perform multiple effective vaccinations with the same virus vector in a way not possible with conventional live virus vectors. Since a standard live virus vaccine probably relies for its efficacy on its ability to replicate in the host animal through many cycles of infection, its usefulness will be severely curtailed in an individual with immunity against that virus. Thus a second challenge with the same virus, whether to provide a booster immunisation against the same protein, or a new response against a different protein, is likely to be ineffective. Using a virus vector with a deletion in an essential gene however, where multi-cycle replication is not desired or required, the events leading to effective immunisation will occur very soon after immunisation. The dose of the mutant virus can be relatively large (since it should be completely safe), and it is therefore unlikely that these early events will be blocked by the host immune response, which will require some time to be mobilised completely.

Although we have referred above to a mutant virus being defective in an essential gene, and optionally containing a gene for an immunogenic pathogen protein, the mutant could be defective in more than one essential gene, and/or contain more than one immunogenic pathogen protein gene. Thus, the mutant virus might include the gene for HIV gp 120, to act as a vaccine in the manner suggested above, and also the gene for the HSV gag protein to be expressed within the vaccinated host and presented at the surface of the host cell in conjunction with MHC-I to stimulate a T-cell response in the host.

The present invention also provides a pharmaceutical preparation which comprises a mutant non-retroviral virus whose genome is defective in respect of a gene essential for the production of infectious virus such that the virus can infect normal cells and undergo replication and expression of viral antigen genes in those cells but cannot produce normal infectious virus, for prophylactic or therapeutic use in generating an immune response in a subject infected therewith.

The mutant virus of the pharmaceutical preparation can be a mutant non-retroviral virus whose genome is defective in respect of a gene essential for the production of infectious virus such that the virus can infect normal cells and replicate therein to give rise to the production and release from the cells of non-infectious viral particles. The pharmaceutical can be a vaccine capable of protecting a patient immunised therewith against infection or the consequences of infection by a non-retroviral virus. The pharmaceutical can be a vaccine capable of protecting a patient immunised therewith against infection or the consequences of infection by the corresponding wild-type virus.

The pharmaceutical can be a therapeutic capable of treating a patient with an established non-retroviral virus infection, e.g. an infection established by the corresponding wild-type virus.

The pharmaceutical can be adminstrable sub-cutaneously, intra-muscularly, intra-dermally, epithelially-, (with or without scarification), nasally-, vaginally-, or orally- and can comprise excipient(s) suitable for the selected administration route.

The mutant virus contained in the pharmaceutical preparation can be capable of protecting a patient immunised therewith against infection or the consequences of infection with HSV eg infection by the corresponding wild-type virus.

The present invention also provides use of a mutant type-1 HSV whose genome is defective in respect of a gene essential for the production of HSV-1 such that the virus can infect normal cells and undergo replication and expression of viral antigen genes in those cells but cannot produce normal infectious virus, for preparation of a pharmaceutical for prophylactic or therapeutic use in generating an immune response in a subject against type-2 HSV infection.

The use may be in respect of pharmaceuticals for intra-epithelial (with or without scarification), intra-vaginal, intra-nasal or per-oral administration.

The present invention also provides an assembly comprising a pharmaceutical (for prophylaxis ie a vaccine or for therapy ie a therapeutic) as described above in a container preferably a pre-filled syringe or glass vial/ampoule with printed instructions on or accompanying the container concerning the administration of the pharmaceutical to a patient to prevent or treat conditions caused by infection with a non-retroviral virus, e.g. HSV infection by HSV-1 and/or HSV-2. The printed instructions may concern the prevention or treatment of facial or genital lesions.

Vaccines containing the mutants as described can be prepared in accordance with methods well known in the art wherein the mutant is combined in admixture with a suitable vehicle. Suitable vehicles include, for example, saline solutions, or other additives recognised in the art for use in compositions applied to prevent viral infections. Such vaccines will contain an effective amount of the mutant as hereby provided and a suitable amount of vehicle in order to prepare a vaccine useful for effective administration to the host.

Dosage rates can be determined according to known methods.

For example, dosage rate may be determined by measuring the optimum amount of antibodies directed against a mutant resulting from administration of varying amounts of the mutant in vaccine preparations. Attention is directed to 'New Trends and Developments in Vaccines', editors A Voller and H Friedman, University Park Press, Baltimore, 1978, for further background details on vaccine preparation.

Therapeutics comprising a mutant as herein provided can be formulated according to known methods to provide therapeutically useful compositions, whereby the mutant is combined in admixture with a pharmaceutically acceptable carrier vehicle. Suitable vehicles and their formulation are described in 'Remington's Pharmaceutical Sciences' (Mack Publishing Co, Easton, Pa., ed. A R Gennaro), by E W Martin, and by F Rola. Such compositions contain an effective amount of the mutant virus hereof together with a suitable amount of carrier vehicle in order to prepare therapeutically acceptable compositions suitable for effective administration to the host.

Typically vaccines are prepared as injectables, (traumatic or non-traumatic) either as liquid solutions or suspensions: solid forms suitable for solution in, or suspension in, liquid prior to injection may also be prepared. Preparations may also be encapsulated in liposomes. The active immunogenic ingredients are often mixed with excipients which are pharmaceutically acceptable and compatible with the active ingredient. Suitable excipients are, for example, water, saline, dextrose, glycerol, trehalose, or the like and combinations thereof. In addition, if desired, the vaccine may contain minor amounts of auxiliary substances such as other stabilisers and/or pH buffering agents, which enhance the stability and thus the effectiveness of the vaccine.

The vaccines may be administered parenterally, by injection, for example, subcutaneously, intraepithelially (with or without scarification). Additional formulations which are suitable for other modes of administration eg oral, vaginal and nasal formulations are also provided. Oral formulations include such normally employed excipients as, for example, pharmaceutical grades of trehalose mannitol, lactose, starch, magnesium stearate, sodium saccharine, cellulose, magnesium carbonate, and the like. The compositions may take the form of solutions, suspensions, tablets, pills, capsules sustained release formulations or powders.

The vaccines are administered in a manner compatible with the dosage formulation, and in such amount as will be prophylactically effective. The quantity to be administered will have been predetermined from preclinical and clinical (phase I) studies to provide the optimum immunological response.

The vaccine may be given in a single dose schedule, or preferably in a multiple dose schedule. A multiple dose schedule is one in which a primary course of vaccination may be with 1-3 separate doses, followed by other doses given at subsequent time intervals required to maintain and or re-enforce the immune response, for example, at 1-4 months for a second dose, and if needed, a subsequent dose(s) after several months. The dosage regimen will also, have been determined from preclinical and clinical studies as maintaining the optimum immunological response over time.

The invention is further described herein by way of example only, and not by way of limitation, with reference to the following sections of detailed description, and to the accompanying Figures.

Sections of detailed description in the present application are:

A. Generation of a Cell line expressing the HSV type 1 gH gene.
B. Production of HSV type 1 virus with an interrupted gH gene.
C. Studies on the protective effect of gH-negative HSV compared to heat killed virus. The data given herein include in-vivo data which show that intra-epithelial vaccination of mice via the ear with a gH-negative mutant form of HSV-1 gave better protection against later challenge with wild-type HSV-1, than similar vaccination with killed HSV-1. A clear protective effect against the establishment of latent infection in the cervical ganglia was also shown for vaccination with the mutant HSV-1.
D. HSV lacking the gH gene as a vector for immunisation against a foreign antigen: introduction of a gp120 gene.
E. Preparation of a DISC HSV-2 mutant virus and complementing gH+ cell line.
F,G. Sections F and G of the detailed description show results indicated as follows:

(1) In a study using the mouse ear model the results reported in section C of the detailed description herein were confirmed. Intra-epithelial vaccination of mice with DISC HSV-1 led to complete protection against replication of the challenge virus wild type (w.t.) HSV-1. Little effective protection was provided by equivalent doses of inactivated HSV-1. DISC HSV-1 also protected against the establishment of latent infection in the cervical ganglia.

(2) Also in the mouse ear model it is shown that no significant differences in antibody titres were observed between animals vaccinated with DISC HSV-1 and an equivalent amount of inactivated HSV-1.

(3) Also in the mouse ear model it is shown that at low vaccination doses, inactivated HSV-1 failed to establish a delayed-type hypersensitivity (DTH) response, whilst equivalent doses of DISC HSV-1 established a DTH response. At high doses, both DISC HSV-1 and inactivated HSV-1 induced similar DTH responses.

(4) Also in a mouse study it was shown that in contrast to vaccination with inactivated HSV-1, vaccination with DISC HSV-1 induced HSV-1 specific cytotoxic T cell activity.

(5) The in vivo mouse ear model was used to study long term prophylactic effect of DISC HSV-1. Two vaccinations of DISC HSV-1 was found to provide better long term protection against challenge with w.t. HSV-1 than two vaccinations of inactivated DISC HSV-1

(6) The in vivo mouse ear model was used to investigate the prophylactic effect of DISC HSV-2 against HSV-2 infection. Intra-epithelial vaccination of mice with DISC HSV-2 provided better protection against replication of the challenge virus w.t. HSV-2 than inactivated DISC HSV-2.

(7) The in vivo guinea-pig vaginal model was used to study the prophylactic effect of DISC HSV-1 against HSV-2 infection. It was shown that intra-epithelial or intra-vaginal vaccination with DISC HSV-1 provided a high degree of protection against the primary symptoms of HSV-2 infection. Immunisation with DISC HSV-1 or inactivated virus retarded growth of challenge virus w.t. HSV-2 in the vagina. Further intra-vaginal vaccination with DISC HSV-1 lessened the number of recurrent HSV-2 lesions in a 100 day follow-up period. Intra-epithelial vaccination with DISC HSV-1 and inactivated virus also resulted in reduced recurrent lesions, but compared to intra-vaginal vaccination with DISC HSV-1, the reduction was less.

(8) Oral and intranasal vaccination of guinea-pigs with DISC HSV-1 led to protection against acute disease symptoms following challenge with w.t. HSV-2. The intranasal route appeared to be more effective than the oral route.

(9) In guinea-pigs which had recovered fully from primary HSV-2 disease, the therapeutic administration of DISC HSV-1 either intra-vaginally or intra-epithelially resulted in an apparent reduction in the frequency of recurrent of disease symptoms compared with mock vaccinated animals. The per vaginum vaccination route in comparison to oral or intra-nasal vaccination resulted in significantly lower levels of recovered virus following challenge.

(10) In guinea-pigs which had recovered fully from primary HSV-2 disease, intra-vaginal therapeutic administration of DISC HSV-2 was more effective in reducing the frequency of recurrence of disease symptoms than treatment with DISC HSV-1.

Referring to the Figures herein:

FIG. 1 illustrates the production of plasmid pGH1.

FIG. 2 illustrates the production of plasmid pGH2.

FIG. **3*a*** shows the pair of complementary oligonucleotides (SEQ ID NO:1, SEQ ID NO:2) used to generate the plasmid pSP64Ta.

FIG. **3*b*** illustrates the production of plasmid pSP64TA.

FIG. **4*a*** shows the two oligonucleotides (SEQ ID NO:3, SEQ ID NO:4) used to generate the plasmid pCMVIEP.

FIG. **4*b*** illustrates the plasmid pCMVIEP.

FIG. 5 illustrates the plasmid pCMVlacZ.

FIG. 6 illustrates the plasmid pGH3.

FIG. 7 illustrates the strategy for construction of plasmid pGH-120.

FIG. 8 shows clearance of wild-type HSV-1 (w.t. HSV-1) strain SC16 virus in the ears of mice vaccinated with either live DISC HSV-1 or inactivated (β-propiolactone treated) w.t. HSV-1 (strain SC16). Groups of 4 mice were vaccinated at the doses indicated by scarification of the left ear pinna. Mice were challenged 14 days post-vaccination with $2\times10^6$ pfu w.t. HSV-1 strain SC16 in the right ear pinna and virus titres were measured 5 days post challenge. Data are expressed as the geometric means and standard errors of the means.

FIG. 9 shows measurement of titres of neutralising and ELISA antibody to w.t. HSV-1 in mice vaccinated with either w.t. HSV-1 (strain SC16), live DISC HSV-1, killed DISC HSV-1 or PBS. Sera from mice were assayed in the presence of complement for neutralising antibodies to w.t. HSV-1 in a plaque reduction assay. Individual titres are expressed as the reciprocal dilution of sera required to neutralise 50% of the infectivity obtained in the absence of antibody.

FIG. 10 shows delayed-type hypersensitivity (DTH) responses in mice vaccinated with either w.t. HSV-1 (strain SC16), live DISC HSV-1, killed DISC HSV-1 or PBS. Mice were vaccinated in the left ear pinna at the doses indicated 14 days prior to challenge with $10^6$ pfu w.t. HSV-1 (strain SC16) in the opposite ear. Ear thickness was measured 24 and 48 hours post-challenge and is expressed as the difference between the challenged and vaccinated ear. Data are presented as the means of differences in ear thickness (in μm).

FIG. 11 shows cytotoxic T cell (CTL) responses in mice vaccinated with either live DISC HSV-1, killed DISC HSV-1, MDK (a thymidine kinase negative HSV-1 strain) or PBS. Mice were immunised twice intraperitoneally three weeks apart and cell suspensions made from spleens 10 days after the second injection. Cells were stimulated in vitro for 4 days before being tested in a CTL assay using $^{51}$Cr-labelled A20/2J as target cells. Data are presented as mean % $^{51}$Cr release from quadruplicate samples at each point. Standard errors of the means are all <10%.

FIG. 12 shows clinical symptoms as assessed by erythema score in guinea-pigs post challenge with $10^{5.2}$ pfu w.t. HSV-2 (strain MS) subsequent to vaccination with doses of $2\times10^7$ pfu DISC HSV-1 at a 3 week interval either by the intra-epithelial or the intra-vaginal route;

FIG. 13 shows clinical symptoms as assessed by total lesion score in guinea-pigs post challenge with $10^{5.2}$ pfu w.t. HSV-2 (strain MS) subsequent to vaccination with doses of $2\times10^7$ pfu DISC HSV-1 at a 3 week interval either by the intra-epithelial or the intra-vaginal route.

FIG. 14 shows post challenge virus w.t. HSV-2 (strain MS) replication in guinea-pigs post challenge with $10^{5.2}$ pfu w.t. HSV-2 (strain MS) subsequent to vaccination with doses of $2\times10^7$ pfu DISC HSV-1 at a 3 week interval either by the intra-epithelial or the intra-vaginal route.

FIGS. 15a and 15b show recurrent disease in guinea-pigs post challenge with $10^{5.2}$ pfu w.t. HSV-2 (strain MS) subsequent to vaccination with doses of $2\times10^7$ pfu DISC HSV-1 at a 3 week interval by the intra-epithelial or the intra-vaginal route. FIG. 15a shows recurrent disease as the cumulative mean erythema index per animal. FIG. 15b shows recurrent disease as cumulative mean number of days with disease per animal.

Figure 16A:
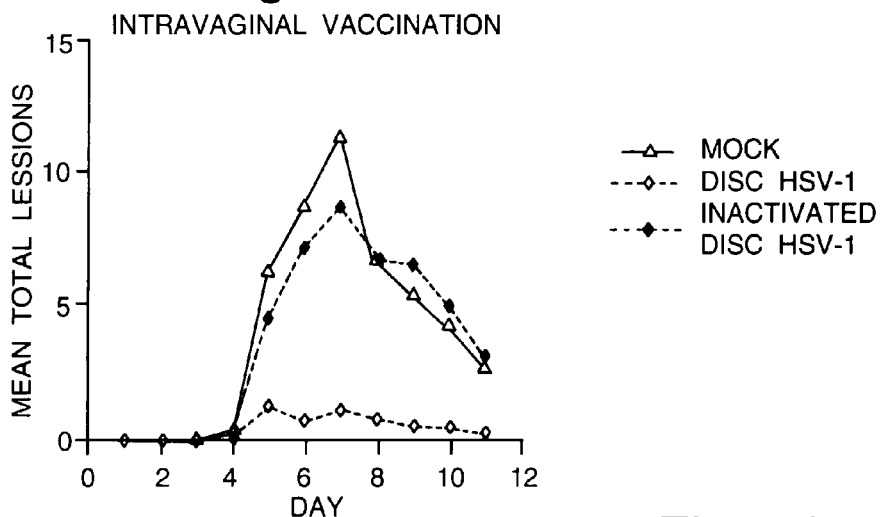
Figure 16B:
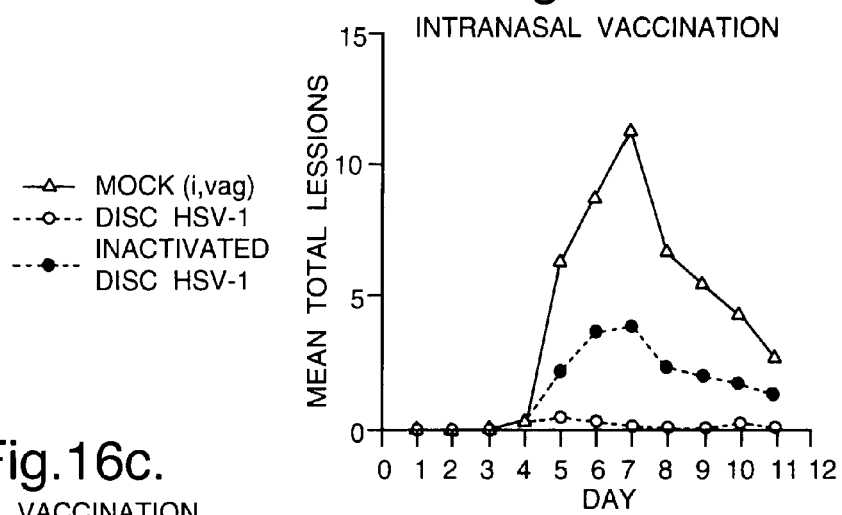
Figure 16C:
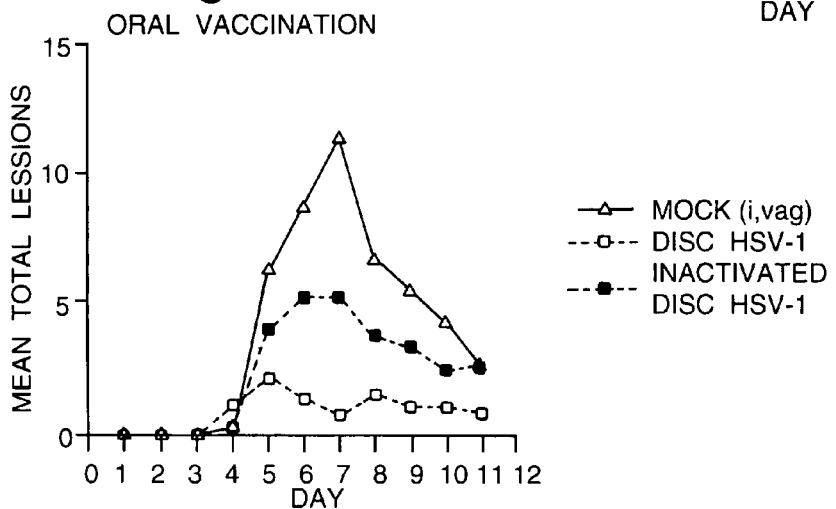

FIG. 16 shows mean lesion score per animal (guinea-pigs) with w.t. HSV-2 (strain MS) infection and which have been vaccinated via the vaginal, oral or nasal routes with a mock virus preparation, DISC HSV-1 or inactivated DISC HSV-1.

Figure 17A:
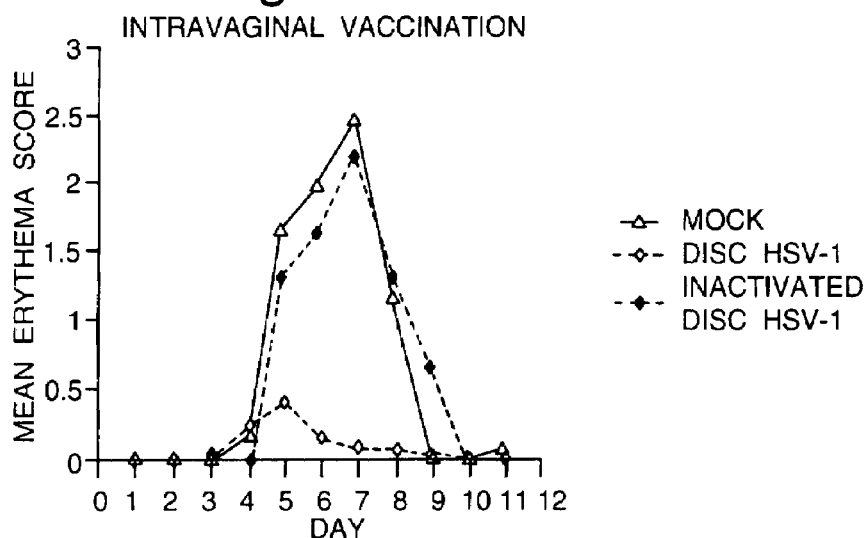
Figure 17B:
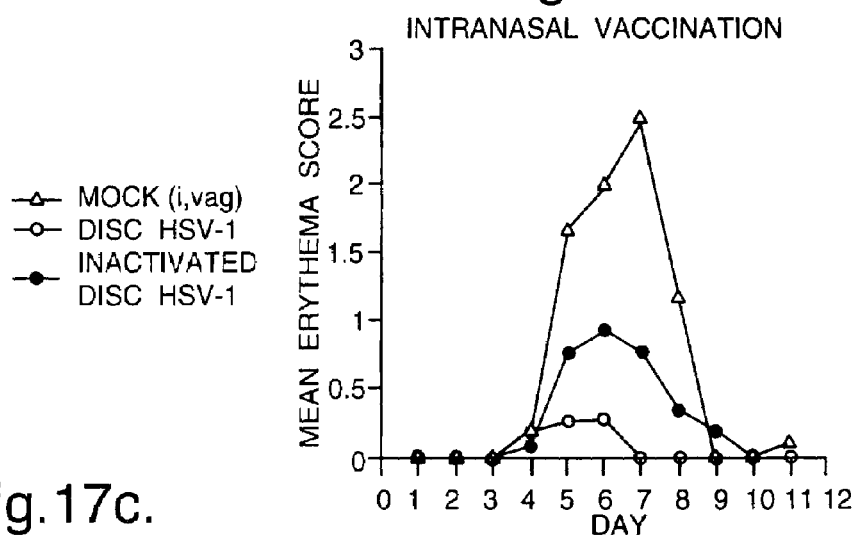
Figure 17C:
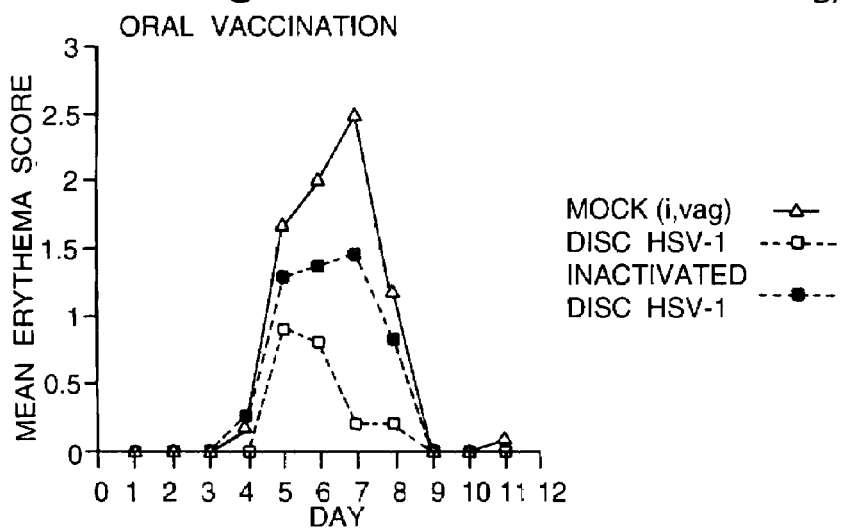

FIG. 17 shows mean erythema score per animal (guinea-pigs) with w.t. HSV-2 (strain MS) infection and which have been vaccinated via the vaginal, oral or nasal routes with a mock virus preparation, DISC HSV-1 or inactivated DISC HSV-1.

Figure 18A:
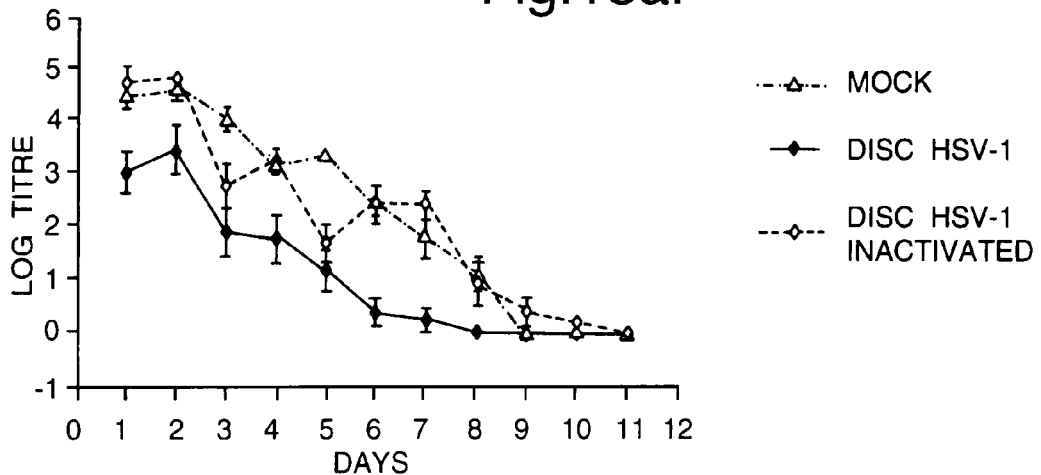
Figure 18B:
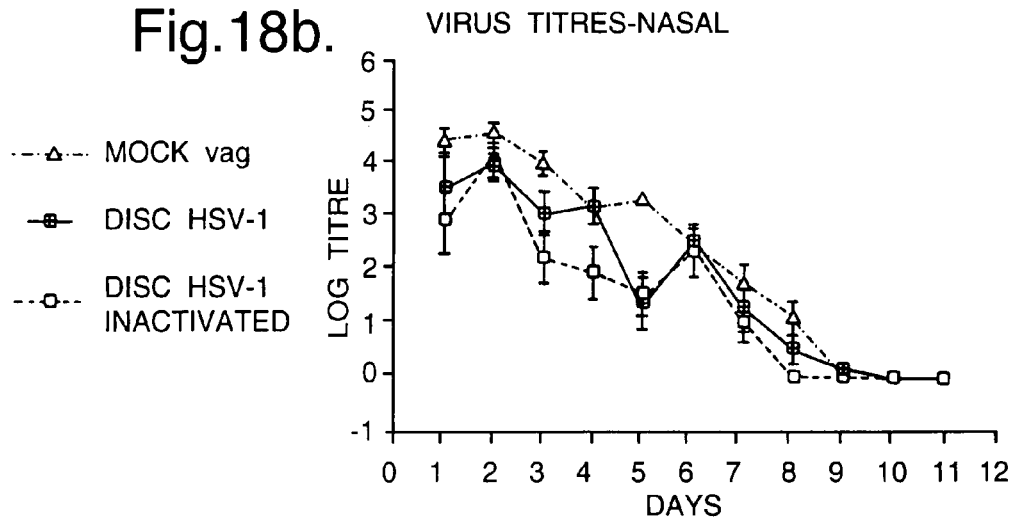
Figure 18C:
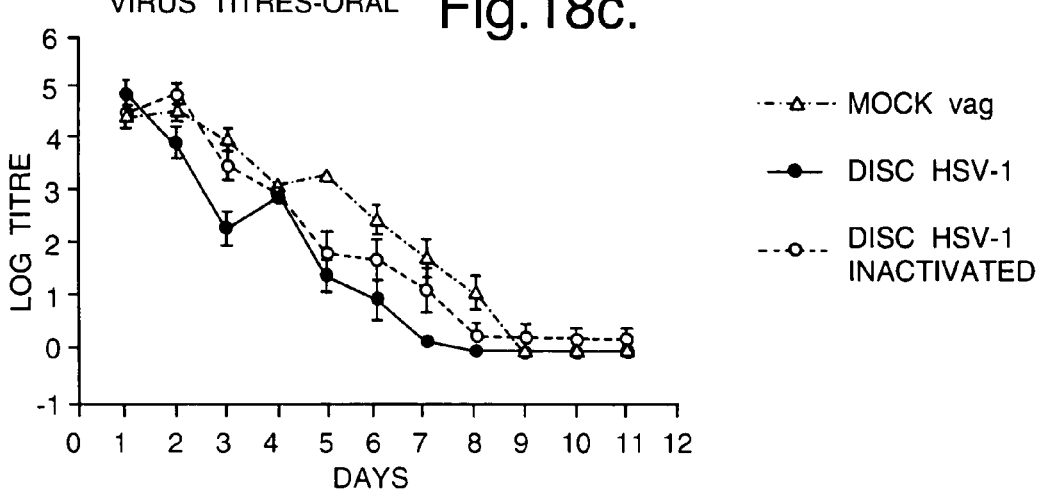

FIG. 18 shows the mean log titre of w.t. HSV-2 (strain MS) per animal (guinea-pigs) with w.t. HSV-2 (strain MS) infection and which have been vaccinated via the vaginal, oral or nasal routes with a mock virus preparation, DISC HSV-1 or inactivated DISC HSV-1.

FIG. 19 shows recurrent disease following therapeutic vaccination. This is shown as mean cumulative number of days on which disease was observed (disease/days) in groups of guinea-pigs vaccinated with DISC HSV-1 either intra-epithelially or intra-vaginally or with a mock virus preparation intra-vaginally after challenge with w.t. HSV-2 (strain MS). Disease was classified as either presence of one or more lesions or an erythema score of 1 or more. Animals were monitored from 4 weeks after initial challenge with w.t. HSV-2 (strain MS) (day o) for 100 days. Animals were vaccinated at Day 0, Day 24 and Day 44 with $2\times10^7$ pfu or equivalent dose as indicated.

FIG. 20 relates to the long-term protective effect in mice of vaccination with DISC HSV-1 against challenge with w.t. HSV-1 (strain SC16). The graph shows the mean log titre of w.t. HSV-1 in the ears 5 days post challenge and 223 days post vaccination.

FIG. 21 relates to the long-term protective effect in mice of vaccination with DISC HSV-1 against challenge with w.t. HSV-1 (strain SC16). The graph shows neutralising antibody titres days 15, 27, 90, 152 and 218 post vaccination as stated.

FIG. 22 relates to the protective effect in mice of vaccination with DISC HSV-2 against challenge with w.t. HSV-2 (strain HG52) for vaccinations with live DISC HSV-2, killed DISC HSV-2 and w.t. HSV-2 (strain HG52) at varying doses, the graph shows mean log titre of w.t. HSV-2 in the ear post challenge.

Figure 23:
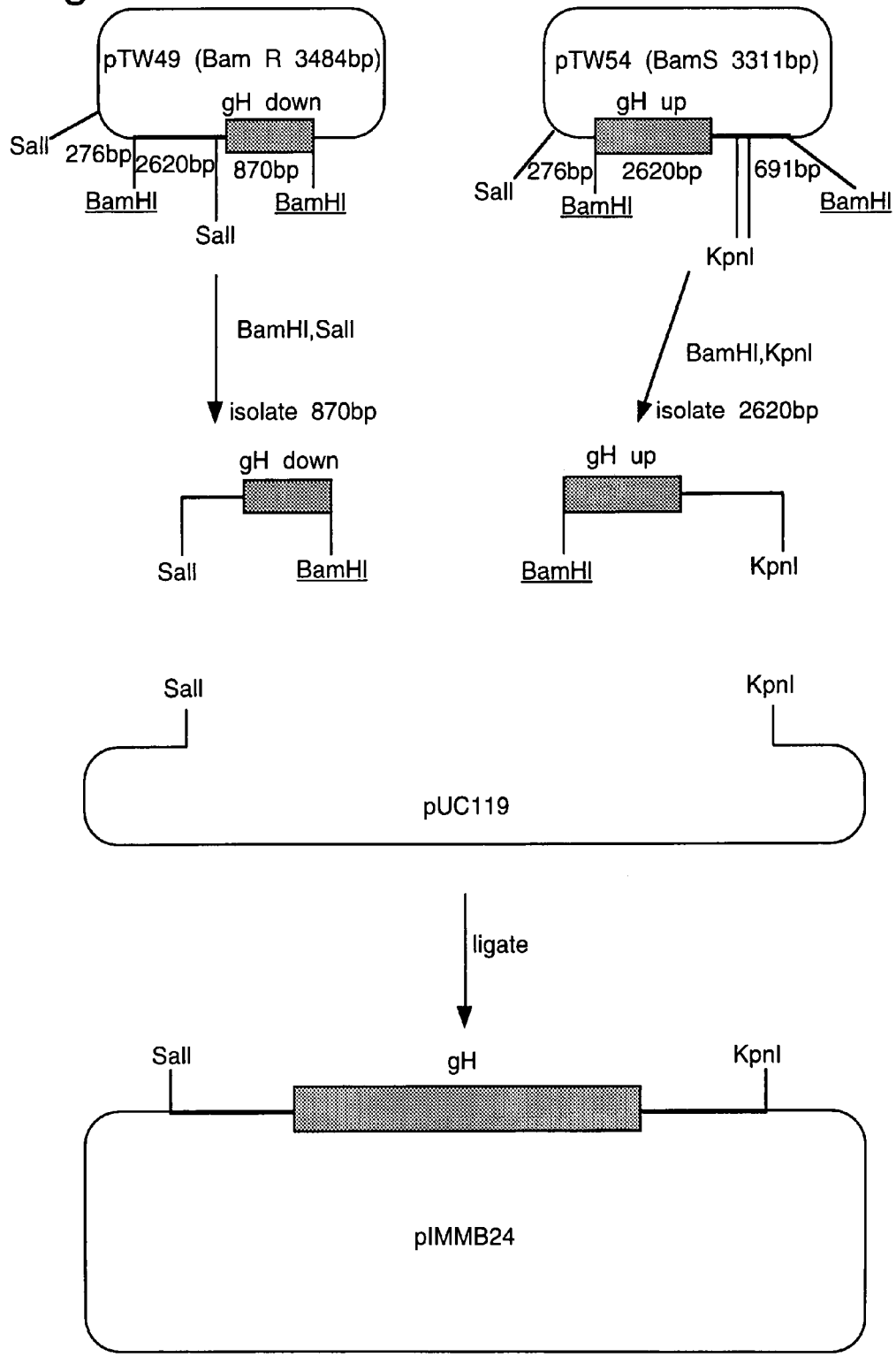

FIG. 23 illustrates the construction of a single plasmid containing the complete HSV-2 gH gene.

FIG. 24 shows the sequence (SEQ ID NO:5) of HSV-2 strain 25766 in the region of the gH gene including a translation of the gH gene in single letter amino acid code (SEQ ID NO:6).

FIG. 25 shows a comparison of the DNA sequence of HSV-1 (SEQ ID NO:7) and HSV-2 strain 25766 (SEQ ID NO:6) in the region of the gH gene.

FIG. 26 shows a comparison of the deduced amino acid sequences of the HSV-1 strain 17 (SEQ ID NO:8) an HSV-2 strain 25766 (SEQ ID NO:6) gH proteins.

Figure 27:
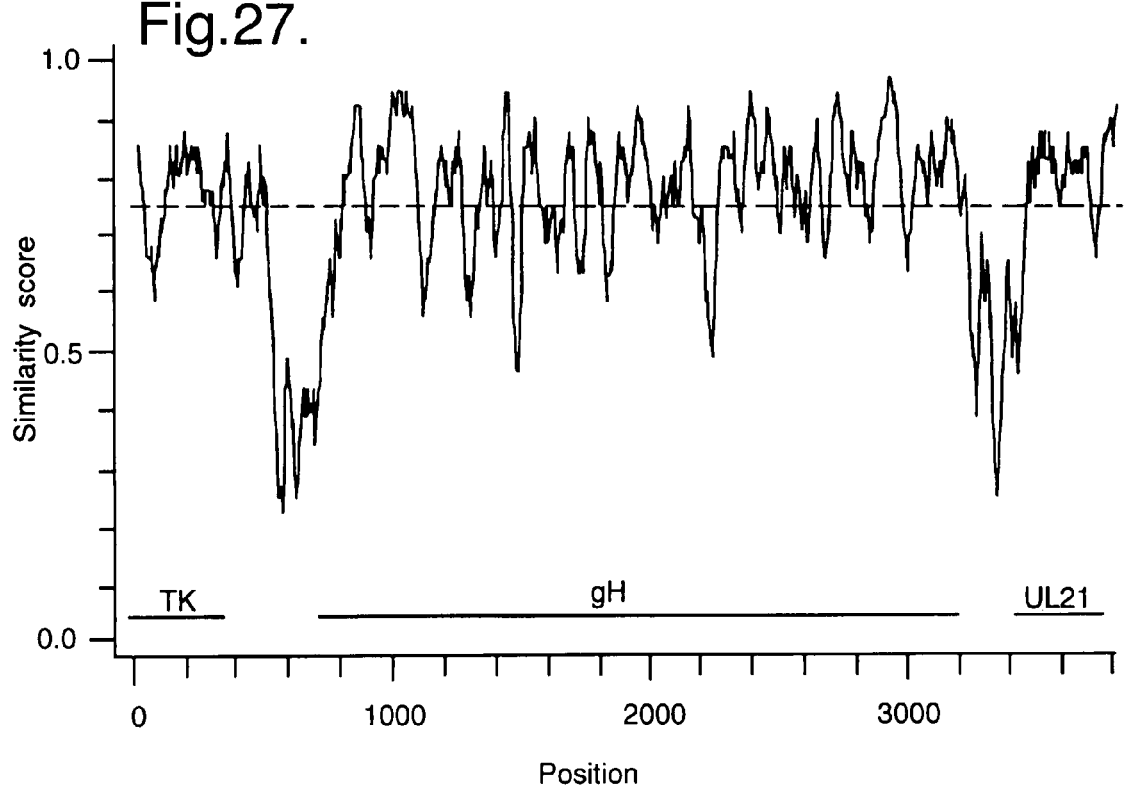

FIG. 27 shows graphically the level of similarity between the DNA sequences of HSV-1 and HSV-2 (SEQ ID NO:5) in the region of the gH gene (from UWGCG program Plotsimilarity).

Figure 28:
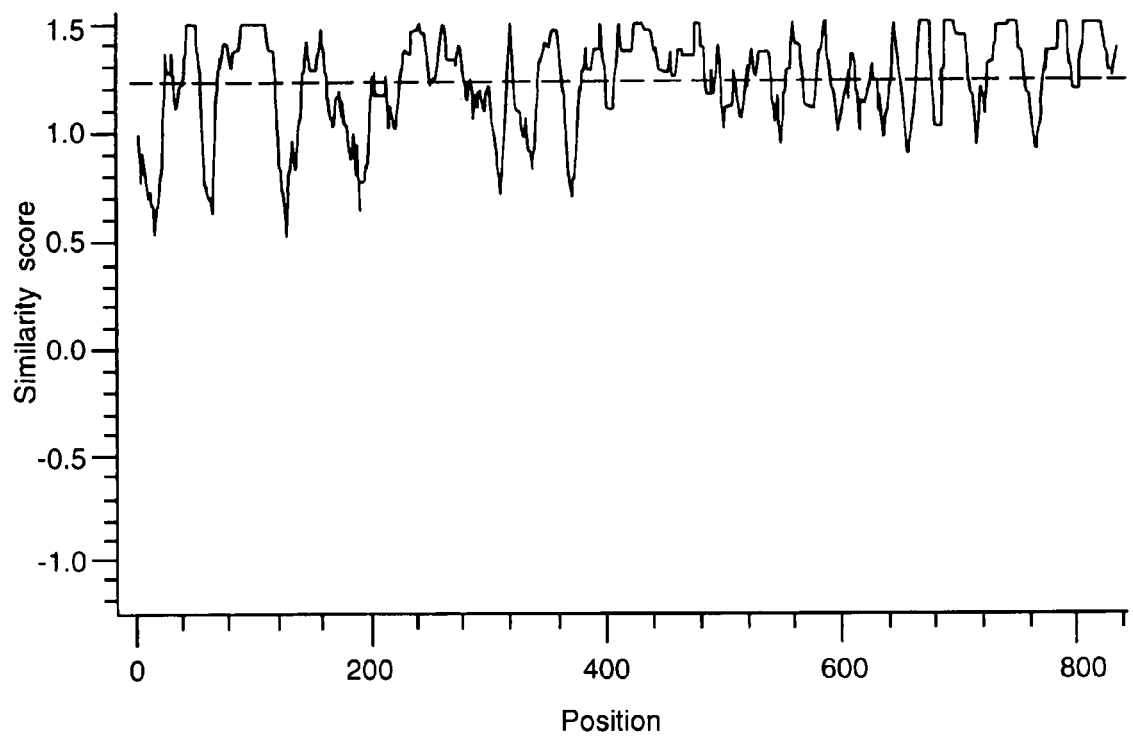

FIG. 28 shows graphically the level of similarity between the amino acid sequences of the HSV-1 (SEQ ID NO:8) and HSV-2 (SEQ ID NO:6) gH proteins (from UWGCG program Plotsimilarity).

Figure 29:
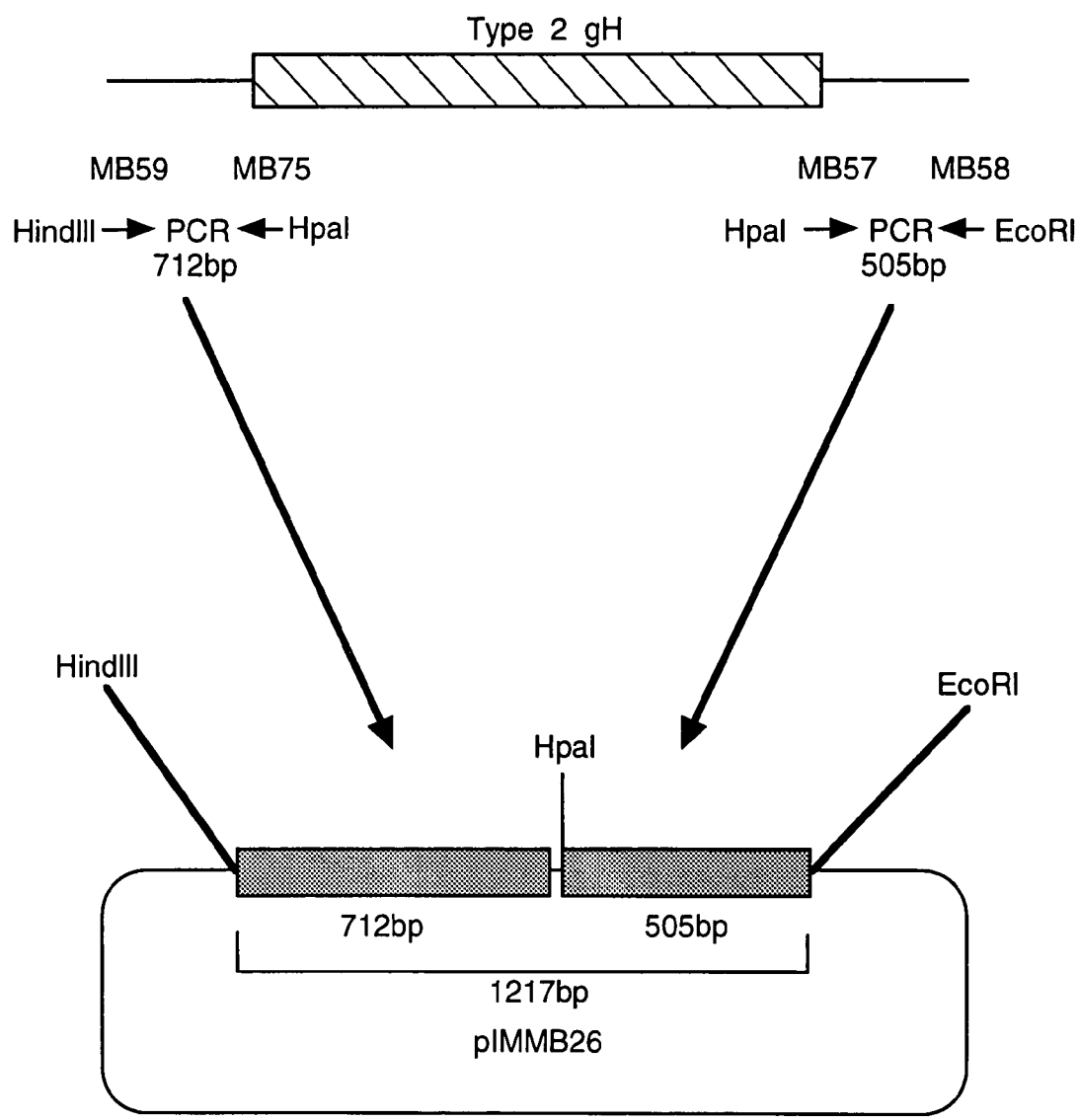

FIG. 29 shows the construction of pIMMB26; two fragments from the left and right sides of the HSV2 gH gene were amplified by PCR and cloned into pUC119. The four oligonucleotides MB57 (SEQ ID NO:9), MB58 (SEQ ID NO:10), B59 (SEQ ID NO:11), MB60 are shown.

Figure 30:
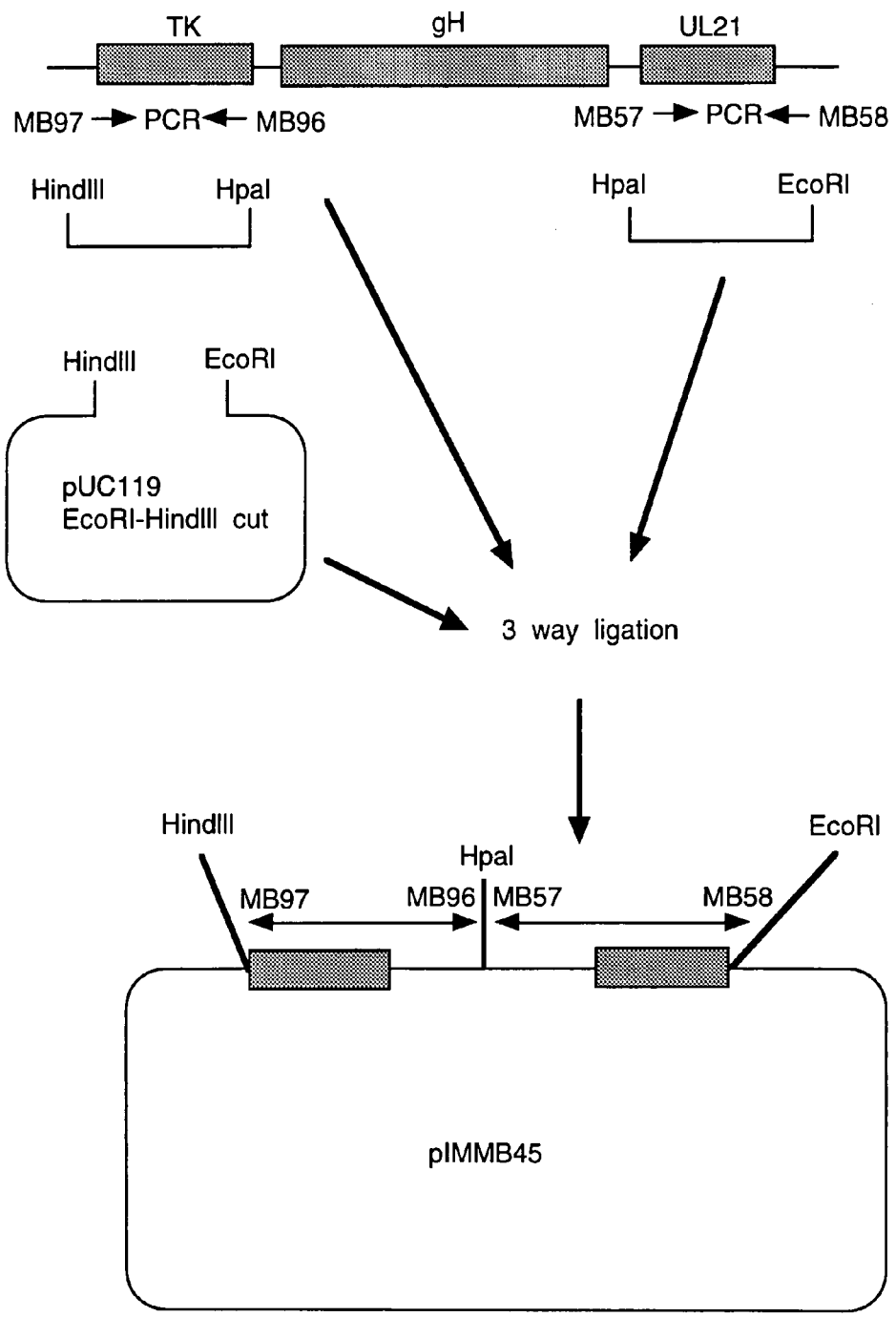

FIG. 30 shows the construction of pIMMB45.

Figure 31:
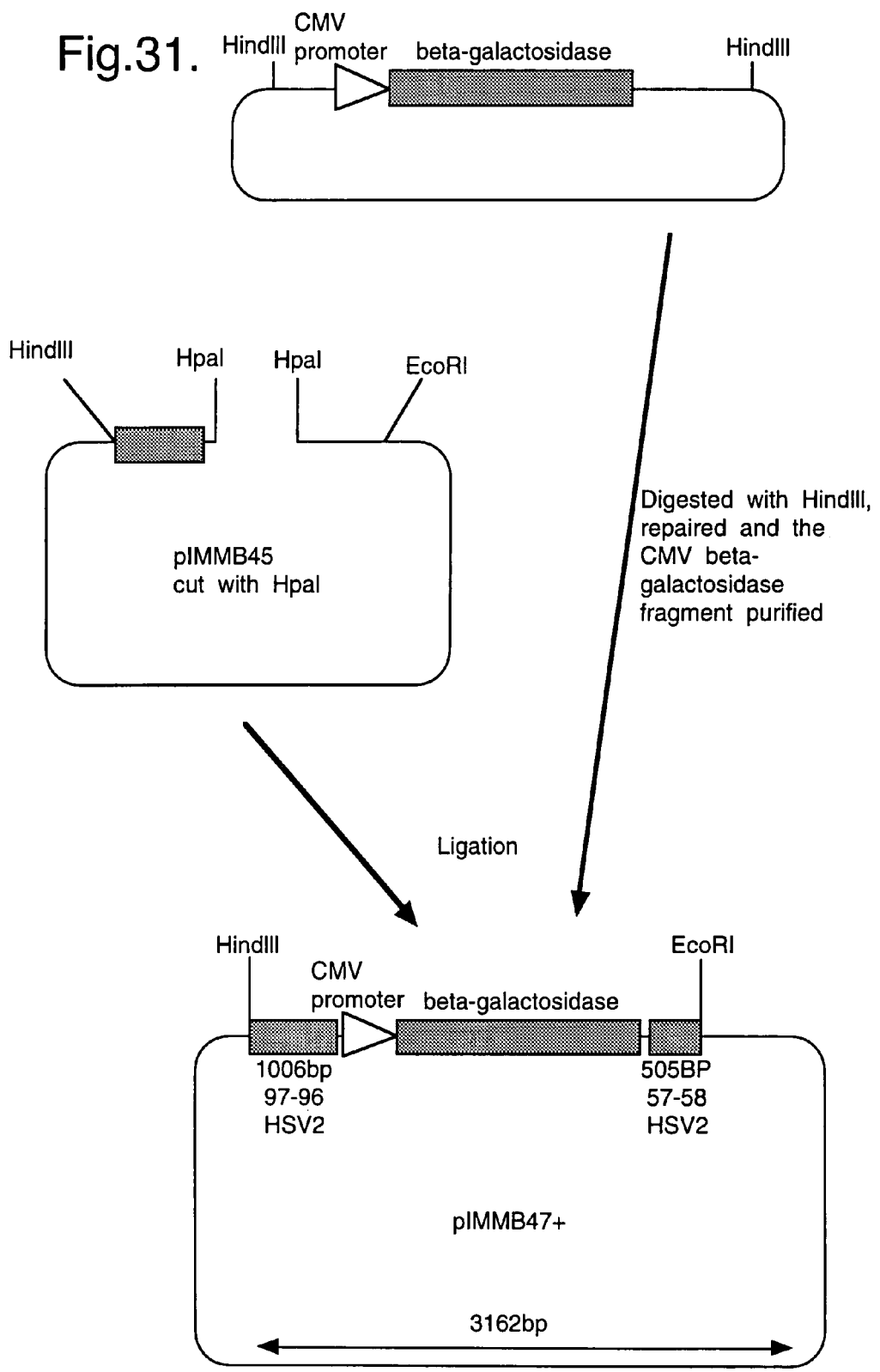

FIG. 31 shows construction of the first stage recombination vector pIMMB47+.

Figure 32:
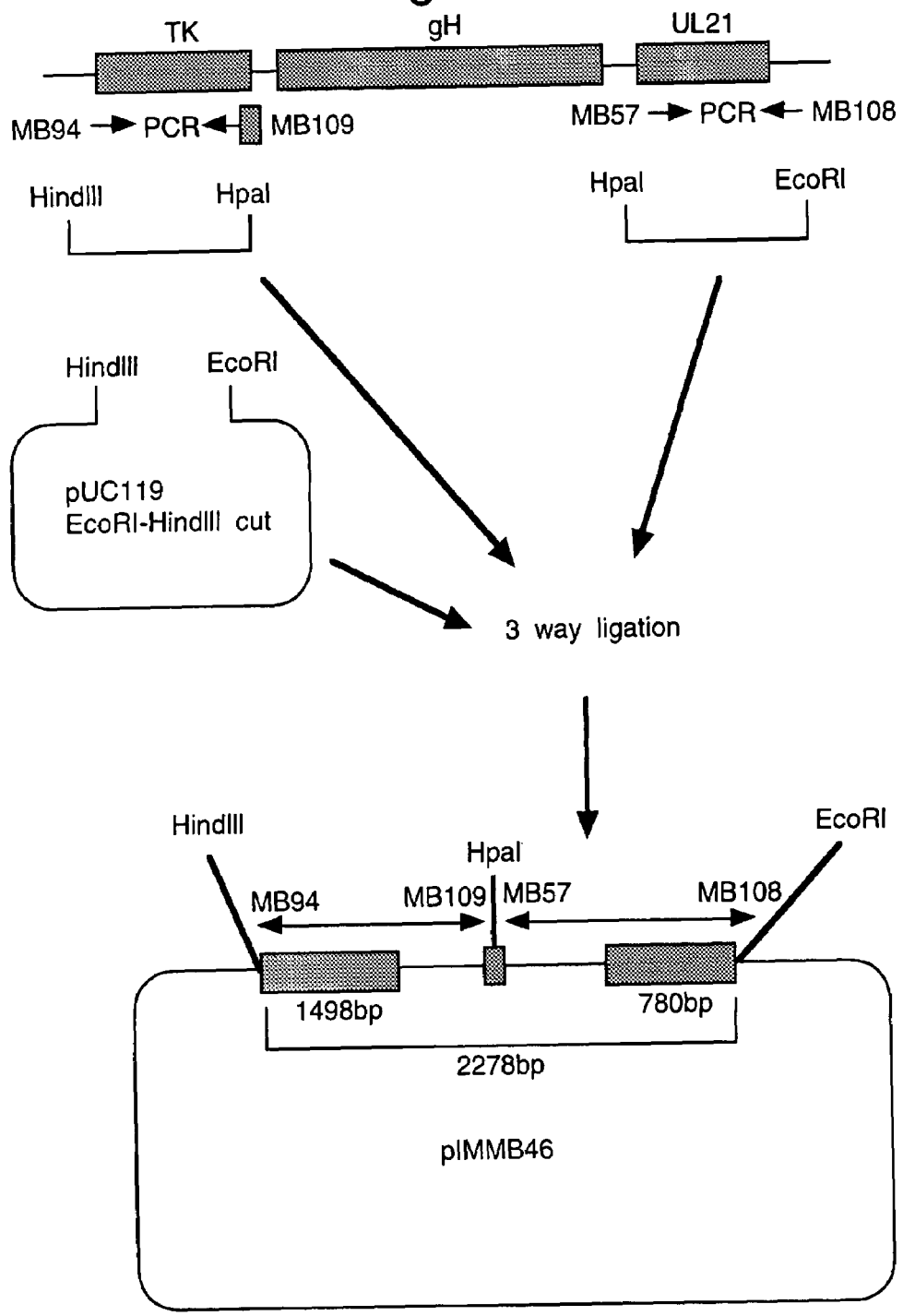

FIG. 32 shows construction of the second stage recombination vector pIMMB46.

Figure 33:
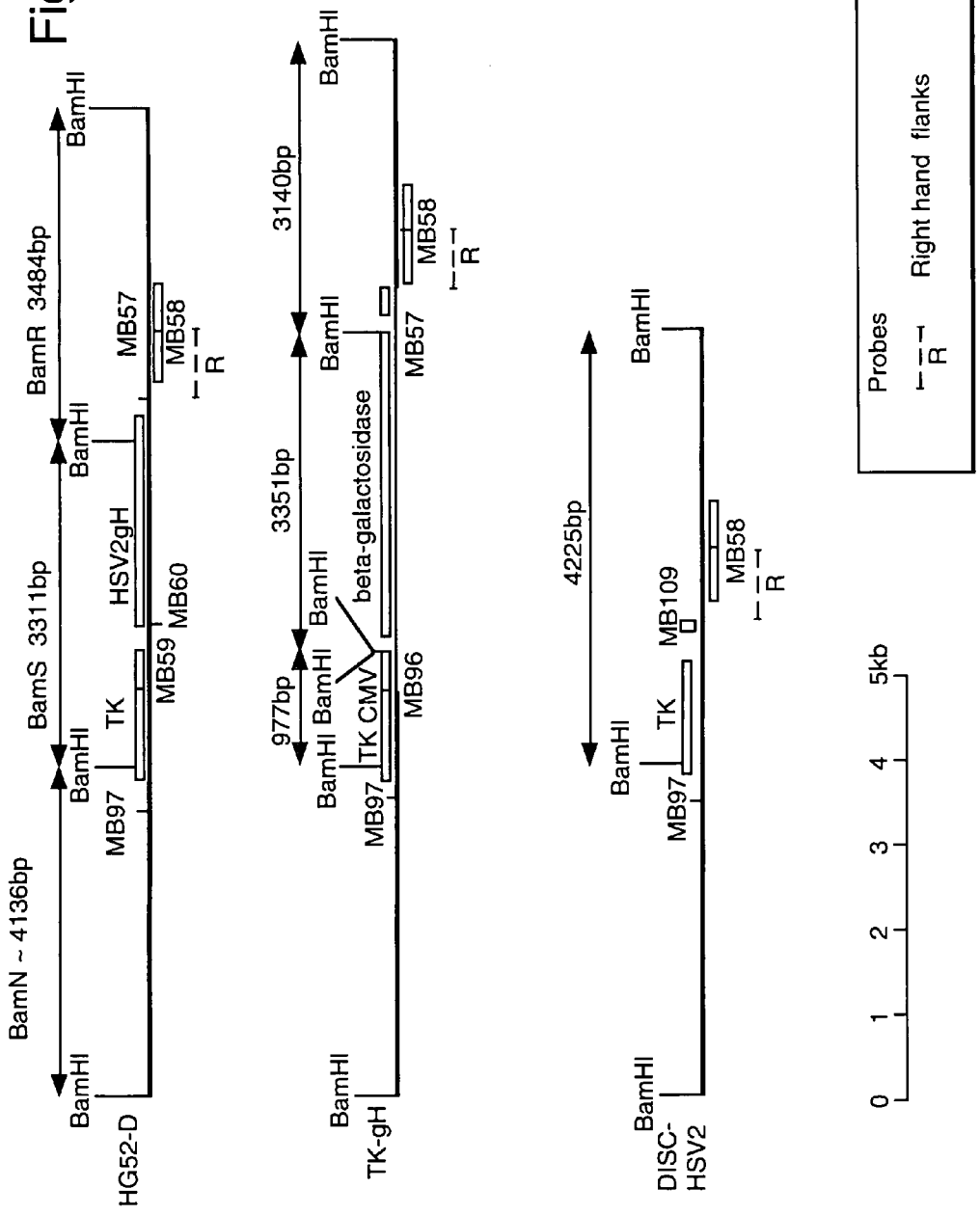

FIG. 33 shows a restriction map analysis for recombinants HG52-D, TK minus DISC virus, TK plus DISC virus.

Figure 34:
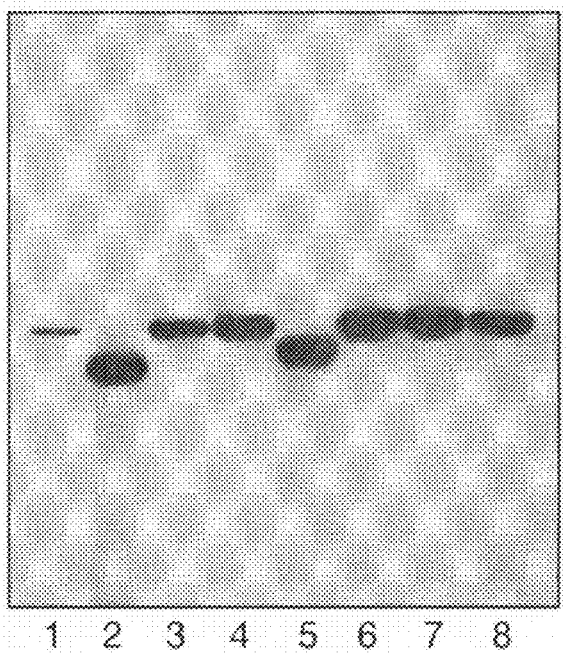

FIG. 34 shows Southern blots of BamHI digestions of various viruses, probed with the right-hand flanking sequence as shown in FIG. 33. Lane 5: HG52-D virus, lane 2: TK-minus "first stage" DISC virus and lanes 3, 4, 6, 7 and 8: TK-plus "second stage" DISC viruses.

Figure 35:
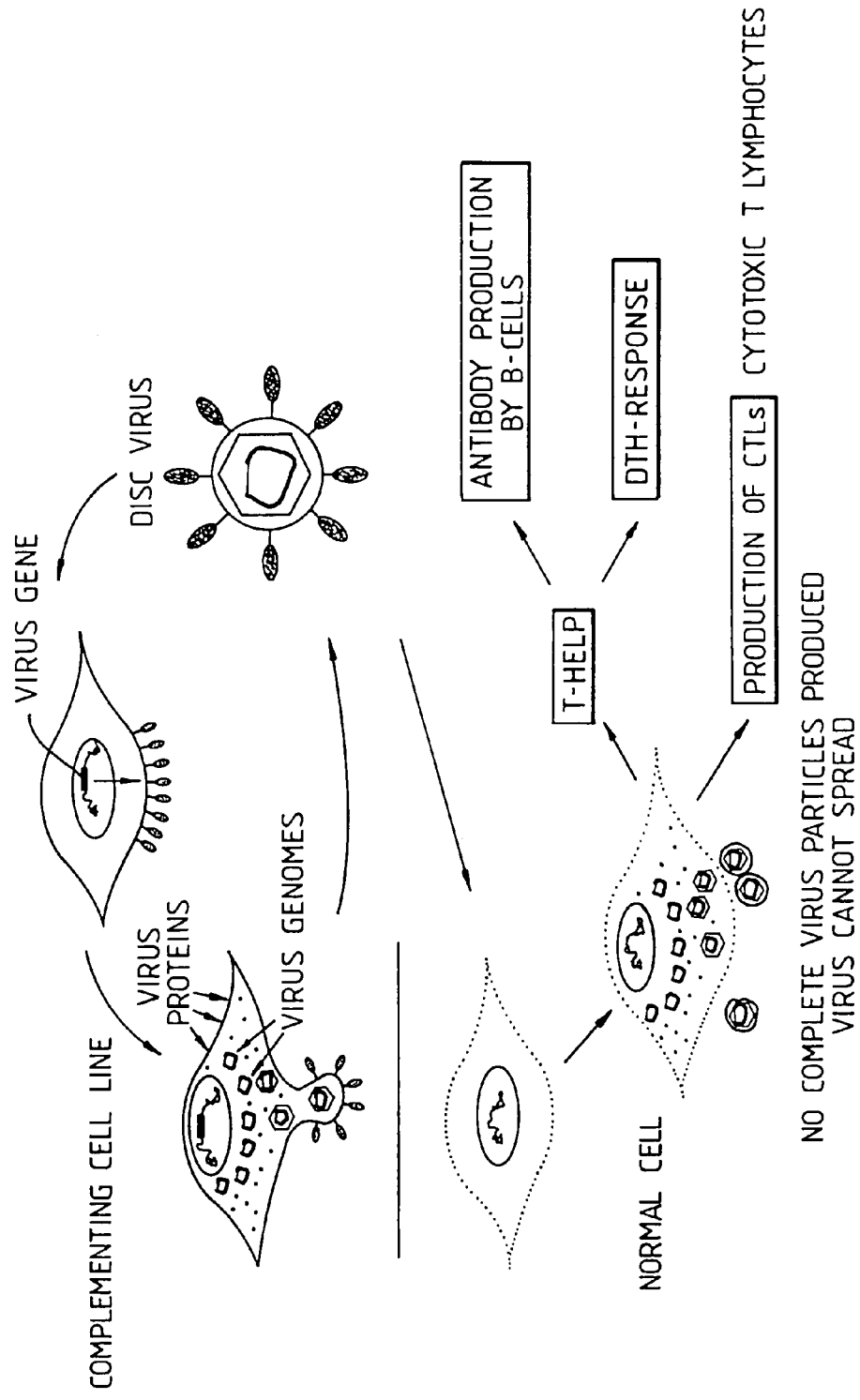

FIG. 35 illustrates diagrammatically the DISC virus concept.

HERPES SIMPLEX VIRUS DELETED IN GLYCOPROTEIN H GENE (gH– HSV)

Herpes simplex virus (HSV) is a large DNA virus which causes a wide range of pathogenic symptoms in man, including recurrent facial and genital lesions, and a rare though often fatal encephalitis. Infection with this virus can be controlled to some extent by chemotherapy using the drug Acyclovir, but as yet there is no vaccine available to prevent primary infection. A difficulty with vaccination against HSV is that the virus generally spreads within the body by direct transfer from cell to cell. Thus humoral immunity is unlikely to be effective, since circulating antibody can only neutralise extracelluar virus. Of more importance for the control of virus infection, is cellular immunity, and so a vaccine which is capable of generating both humoral and cellular immunity, but which is also safe, would be a considerable advantage.

A suitable target gene for inactivation within the HSV genome is the glycoprotein H gene (gH). The gH protein is a glycoprotein which is present on the surface of the virus envelope. This protein is thought to be involved in the process of membrane fusion during entry of the virus into the infected cell. This is because temperature sensitive virus mutants with a lesion in this gene are not excreted from virus infected cells at the non-permissive temperature (P J Desai et al, J Gen Virol 69 (1988), 1147-1156). The protein is expressed late in infection, and so in its absence, a considerable amount of virus protein synthesis may still occur.

All procedures are carried out using standard procedures in the art, in particular genetic manipulation procedures are carried out according to methods described in "Molecular Cloning, A Laboratory Manual", eds. Sambrook, Fritsch and Maniatis, Cold Spring Harbor Laboratory Press, 1989.

Figure 5:
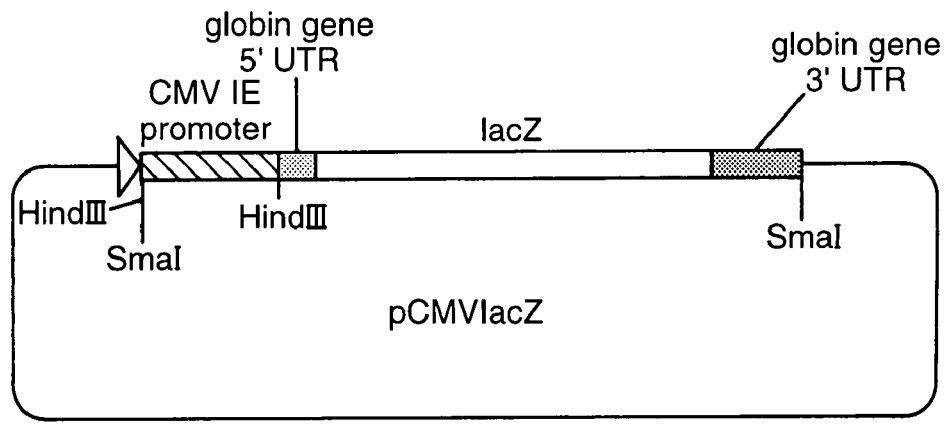
Figure 6:
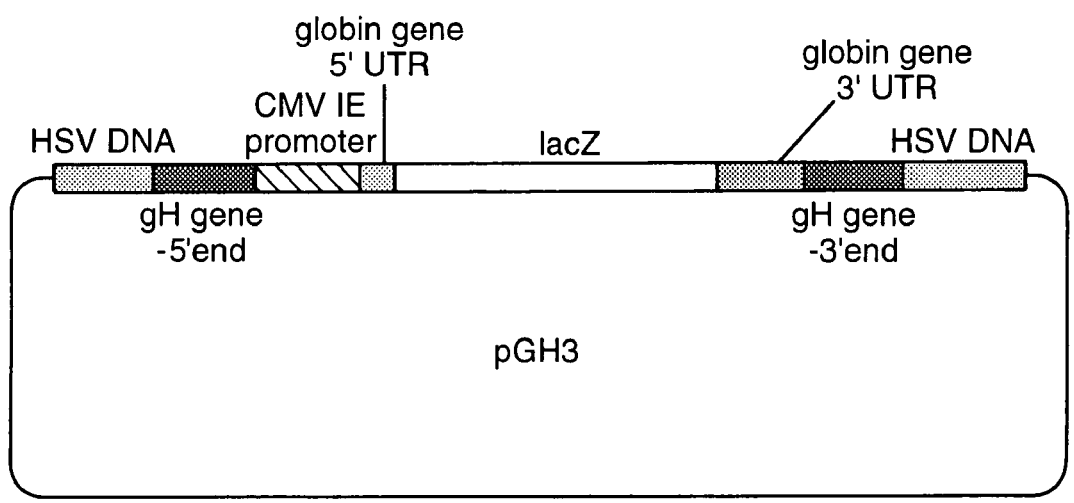

The present description refers to certain strains of HSV-1 and HSV-2. It is not necessary that the description contained herein is put into effect with precisely the mentioned strains. Strains of HSV-1 and HSV-2 having high sequence homology to one another by which the invention may be put into effect are readily available. For example, one source of HSV is the American Type Culture Collection (ATCC), 12301 Parklawn Drive, Rockville, Md. 20852 USA. The following are available from ATCC under the indicated accession numbers.

| | |
|---|---|
| HSV-1 strain F | ATCC accession no. VR-733 |
| HSV-1 strain MacIntyre | ATCC accession no. VR-539 |
| HSV-1 strain MP | ATCC accession no. VR-735 |
| HSV-2 strain G | ATCC accession no. VR-734 |
| HSV-2 strain MS | ATCC accession no. VR-540 |

Section A. Generation of a Cell Line Expressing the HSV Type 1 gH Gene

The gH gene is present in the Unique Long region ($U_L$) of the HSV type 1 genome, between nucleotides 46382 and 43868 (DJ McGeoch et al, J Gen Virol 69 (1988), 1531-1574). A cloned copy of this gene is available within the plasmid pAF2. This plasmid was produced by excising a BglII-XhoI fragment, encompassing the complete gH coding sequence, from the plasmid pTZgH, and cloning it into the BglII site of plasmid pSP64T as described (U A Gompels and A C Minson. J Virol, 63 (1989), 4744-4755). A HindIII fragment containing the promoter sequence for the glycoprotein D (gD) gene (extending from nucleotides −392 to +11, with respect to the start of the gD gene) is then excised from the plasmid pSVD4 (R D Everett, Nucl Acids Res, 11 (1983), 6647-6666), and cloned into the unique HindIII site of pAF2 to generate pGH1 (FIG. 1) such that the promoter sequence is in the correct orientation to drive expression of the gH gene. Thus this plasmid contains the complete gH coding sequence under the control of the HSV type 1 gD gene promoter. This plasmid is then purified and then co-transfected into Vero cells with the plasmid pNE0 (from Pharmacia LKB Biotechnology Inc.) using the standard calcium phosphate co-precipitation technique (F L Graham and A J Van der Eb, Virology 52 (1973), 456-467).

Vero cells which have acquired resistance to neomycin are then selected by passage of the cells in the drug G418, and colonies of these cells cloned by limiting dilution. These neomycin resistant cells are then amplified in tissue culture, and samples are then infected with HSV type 2 virus. Infection with the HSV type 2 virus has the effect of inducing transcription from the type 1 gD promoter present in the complementing cell genome, and so of stimulating production of the type 1 gH protein in the complementing cell. Lysates of the infected cells are then screened for expression of the gH protein by western blotting, using a polyclonal antiserum known to recognise specifically the type 1 gH protein (P J Desai et al, J gen Virol 69 (1988) 1147-1156, op. cit.). Cells which express the required protein are then retained and frozen stocks prepared. This material represents the gH+ complementing cell line.

Section B. Production of HSV Type 1 Virus with an Interrupted gH Gene

A 6432 base pair BglII fragment containing the coding sequence of gH together with HSV flanking sequences is excised from the plasmid pUG102 (U A Gompels and A C Minson, Virology 153 (1986), 230-247) and cloned into the plasmid pAT153 (A J Twigg and D Sherrat, Nature, 283 (1980), 216-218) to generate pGH2 (FIG. 2). This plasmid is digested with PvuII which cuts only within the gH coding sequence at two positions (nucleotides 44955 and 46065 according to the numbering scheme of D J McGeoch et al, 1988, op cit.), and the larger of the two fragments purified. A fragment of DNA consisting of the complete B-galactosidase gene from *E coli* downstream of the Immediate Early gene promoter from Cytomegalovirus (CMV) is then prepared by the following procedure. First of all a pair of complementary oligonucleotides (SEQ ID NO:1, SEQ ID NO:2) (shown in FIG. 3*a*) are annealed and ligated with BglII-digested, phosphatase-treated pSP64T (P A Krieg and D A Melton, Nucl Acids Res 12 (1984), 7057-7070) to generate the plasmid pSP64Ta as shown in FIG. 3*b*. The added linker also includes the initiation codon and first three codons of the B-galactosidase gene (lacZ) of *E. coli*. Next the "core region" of the Immediate Early gene promoter of CMV is amplified from plasmid pUG-H1 (U A Gompels and A C Minson, 1989, op. cit.) by the Polymerase Chain Reaction technique (PCR—Molecular Cloning, ed. Sambrook et al., op cit.) using the two oligonucleotides (SEQ ID NO:3, SEQ ID NO:4) shown in FIG. 4*a*, which correspond to sequences from −302 to −288 (SEQ ID NO:3) from −13 to −36 (SEQ ID NO:4) respectively (numbered in relation to the start of the CMV Immediate Early gene as described by A Akrigg et al, Virus Research, 2 (1985), 107-121). These oligonucleotides (SEQ ID NO:3, SEQ ID NO:4) also contain, at their 5' ends, sites for the restriction enzyme HindIII, and in the case of the oligonucleotide annealing upstream of the promoter (SEQ ID NO:3), an additional SmaI site. The PCR-amplified product DNA is then digested with HindIII, and cloned into HindIII-digested pSP64Ta, to generate the plasmid pCMVIEP (FIG. 4b). Finally, a DNA fragment containing a complete copy of the E. coli B-galactosidase gene, lacking only the extreme 5' end of the coding sequence, is isolated by digestion of the plasmid pSC8 (S Chakrabarti et al, Mol Cell Biol, 5 (1985), 3403-3409) with BamHI, and cloned into the unique BglII site of pCMVIEP to generate pCMVlacZ (FIG. 5). A fragment of DNA containing the B-galactosidase gene under the control of the CMV IE promoter is then isolated by digestion of pCMV-lacZ with SmaI, and ligated with the purified PvuII fragment of pGH2 described above, to generate pGH3, which consists of a copy of the gH gene interrupted by a functional B-galactosidase gene (FIG. 6).

The next step is to replace the wild type gH gene in the HSV genome with this interrupted version, and this is done by allowing recombination between HSV DNA and plasmid pGH3, followed by selection of those viruses which have acquired a functional B-galactosidase gene. Plasmid pGH3 DNA is therefore cotransfected into cells expressing the gH gene (the gH+ complementing cell line described in section A) along with purified HSV DNA isolated from purified HSV virions (R A Killington and K L Powell, in "Growth, Assay and Purification of Heprpesviruses", ch. 10 in "Techniques in Virology: A practical Approach" (ed. B W J Mahy) pp 207-236, IRL Press, Oxford, 1985) by the standard calcium phosphate precipitation technique (F L Graham and A J Van der Eb, 1973, op. cit.).

The progeny HSV virus produced from this transfection experiment is then plated on monolayers of gH+ complementing cells by standard plaque assay, using an agar overlay, in the presence of 5-bromo-chloro-3-indolyl-β-D-galactoside (X-gal), a chromogenic substrate which is converted to a blue substance by the enzyme β-galactosidase. Thus plaques resulting from infection by virus genomes containing and expressing the β-galactosidase gene will appear blue. These virus genomes should therefore carry an interrupted version of the gH gene. Virus is recovered from these plaques by picking plugs of agar from the appropriate part of the plate, and virus stocks prepared through growth of virus in the gH+ complementing cell line. These viruses, since they bear non-functional versions of the gH gene, should be unable to form plaques on cells which do not contain and express an endogenous functional copy of the gH gene, and so to confirm this, a sample of the virus is assayed for its ability to form plaques on wild type Vero cell monolayers in comparison with the gH-complementing cells.

Finally, virus DNA is prepared from these stocks, and checked for the expected DNA structure around the gH gene by Southern blotting. After confirmation of the correct genetic structure, a large stock of the gH gene-deficient virus is then prepared by inoculation of a sample of the virus into a large-scale culture of the gH+ complementing cell line (multiplicity of infection=0.01), and three days later, the infected cells are harvested. The infected cells are disrupted by sonication in order to release the cell-associated virus, and the total sonicated mixture stored at −70° as the virus master stock. The titre of the virus as the stock is then established by plaque assay on the gH+ complementing cell line. Samples of this virus stock are then used to prepare working stocks as before, and these working stocks are then used to infect laboratory animals as described below.

Publications relevant to these mutant viruses are A Forrester et al, J Virol, 66 (1992), pp 341-348, and H E Farrell et al, J Virol 68 (1994), pp 927-932.

Section C. Studies on the Protective Effect of gH-Negative HSV Compared to Heat Killed Virus In order to assess the host immunological response to this virus, challenge experiments were conducted in mice according to the experimental plan described below.

The protective effect of a live gH virus preparation was compared with an inactivated preparation of wild type (WT) virus (strain SC16) as follows.

Preparation of Inactivated Wild Type Virus for Vaccination:

HSV type 1 (strain SC16) was grown by low multiplicity infection (0.01 pfu/cell) of Vero cells. After three days, the virus was harvested, and cytoplasmic virus recovered by Dounce homogenisation. Nuclei were removed by centrifugation at 500×g for 15 min, and the virus was recovered from the supernatant by centrifugation on to a 40% sucrose cushion at 12K for 60 min Beckman Sw27 rotor. The banded virus was diluted, pelleted and purified by sucrose gradient centrifugation (Killington and Powell, 1985, op. cit.). The virus band was harvested from the gradient, and the virus recovered by centrifugation. Virus was resuspended in phosphate-buffered saline (PBS), assayed for infectivity by plaque titration on baby hamster kidney (BHK) cells, and the particle count determined by electron microscopy. The particle:infectivity ratio of the preparation was 110 particles/pfu. The virus was diluted to $2.5\times10^{10}$ pfu/ml in PBS, and inactivated by treatment with β-propiolactone for 60 min at 20° C. Aliquots were then stored at −70° C.

Preparation of Live $gH^-$ Virus for Vaccination:

This material was prepared as described for the wild type virus, except that the virus was grown in the gH+ complementing cell line containing and expressing the HSV type 1 gH gene, and it was not inactivated by treatment with β-propiolactone. The particle:infectivity ratio of this preparation was 150:1. The concentration of this preparation was adjusted to $2.5\times10^{10}$ pfu/ml and aliquots were stored in PBS at −70° C.

Vaccination Protocol:

4 week-old female balb/C mice (purchased from Tucks U.K. Ltd) were vaccinated with various doses of inactivated WT virus or live gH− virus in 2 μl volumes of phosphate-buffered saline by droplet application and needle scarification of the right ear as follows:

| | |
|---|---|
| Group A | Control - no virus |
| Group B | $5\times10^4$ pfu virus vaccine |
| Group C | $5\times10^5$ pfu virus vaccine |
| Group D | $5\times10^6$ pfu virus vaccine |
| Group E | $5\times10^7$ pfu virus vaccine |

After 14 days, all mice were challenged by similar inoculation of the left ear with $2\times10^6$ pfu HSV-1 strain SC16 (wild type virus). Mice were killed after 5 days and assayed for virus infectivity in the left ear and left cervical ganglia cII, cIII and cIV (combined). For latency studies, other vaccinated and challenged animals were killed after 1 month, and tested for latent infection by dissecting out the cII, cIII and cIV ganglia. These were incubated in medium for five days then homogenised and assayed for the presence of infectious virus by standard plaque assay. All the following results are expressed as pfu/organ.

TABLE C-1

Titre of challenge virus present during the acute phase of infection after vaccination with live gH- virus
Virus titre - $\log_{10}$pfu (WT SC16)

| | Mouse no. | Ears | mean | cervical ganglia* | mean |
|---|---|---|---|---|---|
| Group A | 1 | 4.2 | 4.3 | 3.3 | 3.4 |
| | 2 | 4.2 | | 3.4 | |
| | 3 | 4.6 | | 3.4 | |
| | 4 | 4.3 | | 3.4 | |
| Group B | 1 | 3.4 | 0.85 | 1.5 | 1.8 |
| | 2 | none | | 2.4 | |
| | 3 | none | | 2.0 | |
| | 4 | none | | 1.5 | |
| Group C | 1 | none | — | none | — |
| | 2 | none | | none | |
| | 3 | none | | none | |
| | 4 | none | | none | |
| Group D | 1 | none | — | none | — |
| | 2 | none | | none | |
| | 3 | none | | none | |
| | 4 | none | | none | |
| Group E | 1 | none | — | none | — |
| | 2 | none | | none | |
| | 3 | none | | none | |
| | 4 | none | | none | |

*Pooled cervical ganglia cII, cIII and cIV

TABLE C-2

Titre of challenge virus present during the acute phase of infection after vaccination with inactivated WT HSV-1
Virus titre - $\log_{10}$pfu (WT SC16)

| | Mouse no. | Ears | mean | cervical ganglia* | mean |
|---|---|---|---|---|---|
| Group A | 1 | 5.7 | 5.2 | 2.6 | 2.3 |
| | 2 | 4.4 | | 2.3 | |
| | 3 | 5.7 | | 2.1 | |
| Group B | 1 | 4.2 | 3.8 | 1.9 | 1.2 |
| | 2 | 3.6 | | 3.1 | |
| | 3 | 3.5 | | none | |
| | 4 | 3.8 | | none | |
| Group C | 1 | none | 2.0 | none | — |
| | 2 | 2.5 | | none | |
| | 3 | 2.9 | | none | |
| | 4 | 2.7 | | none | |
| Group D | 1 | 3.9 | 2.6 | none | — |
| | 2 | 2.0 | | none | |
| | 3 | 2.0 | | none | |
| | 4 | 2.3 | | none | |
| Group E | 1 | none | — | none | — |
| | 2 | none | | none | |
| | 3 | none | | none | |
| | 4 | none | | none | |

*Pooled cervical ganglia cII, cIII and cIV

TABLE C-3

Titre of challenge virus present as latent virus in the cervical ganglia after vaccination with live gH-HSV-1

| | Mouse No. | Virus titre in cervical ganglia* ($\log_{10}$pfu WT) | Reactivation frequency |
|---|---|---|---|
| Group A | 1 | 5.4 | 5/5 |
| | 2 | 4.6 | |
| | 3 | 5.0 | |
| | 4 | 4.8 | |
| | 5 | 5.3 | |

TABLE C-3-continued

Titre of challenge virus present as latent virus in the cervical ganglia after vaccination with live gH-HSV-1

| | Mouse No. | Virus titre in cervical ganglia* ($\log_{10}$pfu WT) | Reactivation frequency |
|---|---|---|---|
| Group B | 1 | none | 3/4 |
| | 2 | 1.5 | |
| | 3 | 5.1 | |
| | 4 | 5.3 | |
| Group C | 1 | none | 1/3 |
| | 2 | none | |
| | 3 | 3.2 | |
| Group D | 1 | none | 0/4 |
| | 2 | none | |
| | 3 | none | |
| | 4 | none | |
| Group E | 1 | none | 0/4 |
| | 2 | none | |
| | 3 | none | |
| | 4 | none | |

*Pooled cervical ganglia cII, cIII and cIV

TABLE C-4

Titre of latent challenge virus in the cervical ganglia after vaccination with inactivated WT HSV-1

| | Mouse No. | Virus titre in cervical ganglia* ($\log_{10}$pfu WT) | Reactivation frequency |
|---|---|---|---|
| Group A | 1 | none | 3/4 |
| | 2 | 5.0 | |
| | 3 | 5.0 | |
| | 4 | 5.2 | |
| Group B | 1 | 3.5 | 3/4 |
| | 2 | 4.0 | |
| | 3 | 5.5 | |
| | 4 | none | |
| Group C | 1 | 3.6 | 2/4 |
| | 2 | 5.1 | |
| | 3 | none | |
| | 4 | none | |
| Group D | 1 | none | 1/4 |
| | 2 | 4.8 | |
| | 3 | none | |
| | 4 | none | |
| Group E | 1 | none | 0/4 |
| | 2 | none | |
| | 3 | none | |
| | 4 | none | |

*Pooled cervical ganglia cII, cIII and cIV
(p.f.u. = plaque forming units; gH- is a virus with a defective gH gene).

These results show the titre of the challenge virus wt SC16 present in the ears and cervical ganglia during the acute phase of infection. Thus, a low titre indicates good effectiveness of the vaccination regimen with gH- virus whereas a higher titre, indicates poorer effectiveness. It is clear from the results that vaccination with live gH- HSV virus is very much more effective than an equivalent amount of inactivated WT virus. With the inactivated preparation, a dose of $5\times10^7$ pfu was required to prevent challenge virus replication in the ear, whereas with the live gH- virus; 100-1000 fold less virus was required. Live gH- virus vaccination with $5\times10^5$ pfu and over, was also able to block replication of the challenge virus in the cervical ganglia during the acute phase of infection, and furthermore showed a clear protective effect against the establishment of latent infection in the cervical ganglia.

Section D. HSV Lacking the gH Gene as a Vector for Immunisation Against a Foreign Antigen: Introduction of the gp120 Gene of SIVmac Strain 142 into the Genome of gH− HSV Virus Viruses with deletions in essential genes may, as described above, be used as safe vectors for the delivery of foreign antigens to the immune system, and the gH− HSV virus described above provides a suitable example of a such a vector. This virus could be used to express any desired foreign antigen, but a particularly attractive possibility would be the major antigenic proteins of the AIDS virus human immunodeficiency virus (HIV). Thus these sequences would be inserted into the gH− HSV genome in a way that would ensure their expression during infection of normal cells (i.e. non-complementing cells) by the recombinant virus. Infection of an individual with such a virus could lead to a latent infection which, from time to time upon reactivation, would lead to a burst of production of the foreign antigen, resulting in stimulation of the immune response to that protein.

Since studies to test this approach directly in humans are not feasible at present, as an initial stage, the approach may be tested in monkeys using the Simian AIDS virus $SIV_{mac}$ (Simian immunodeficiency virus isolated from macaques). A suitable SIV gene for this purpose is that encoding the gp120 protein, one of the major antigenic targets for this virus. This gene is therefore introduced into the gH− HSV genome, and the efficacy of this virus as a vaccine to protect monkeys against challenge with SIV assessed.

Figure 1:
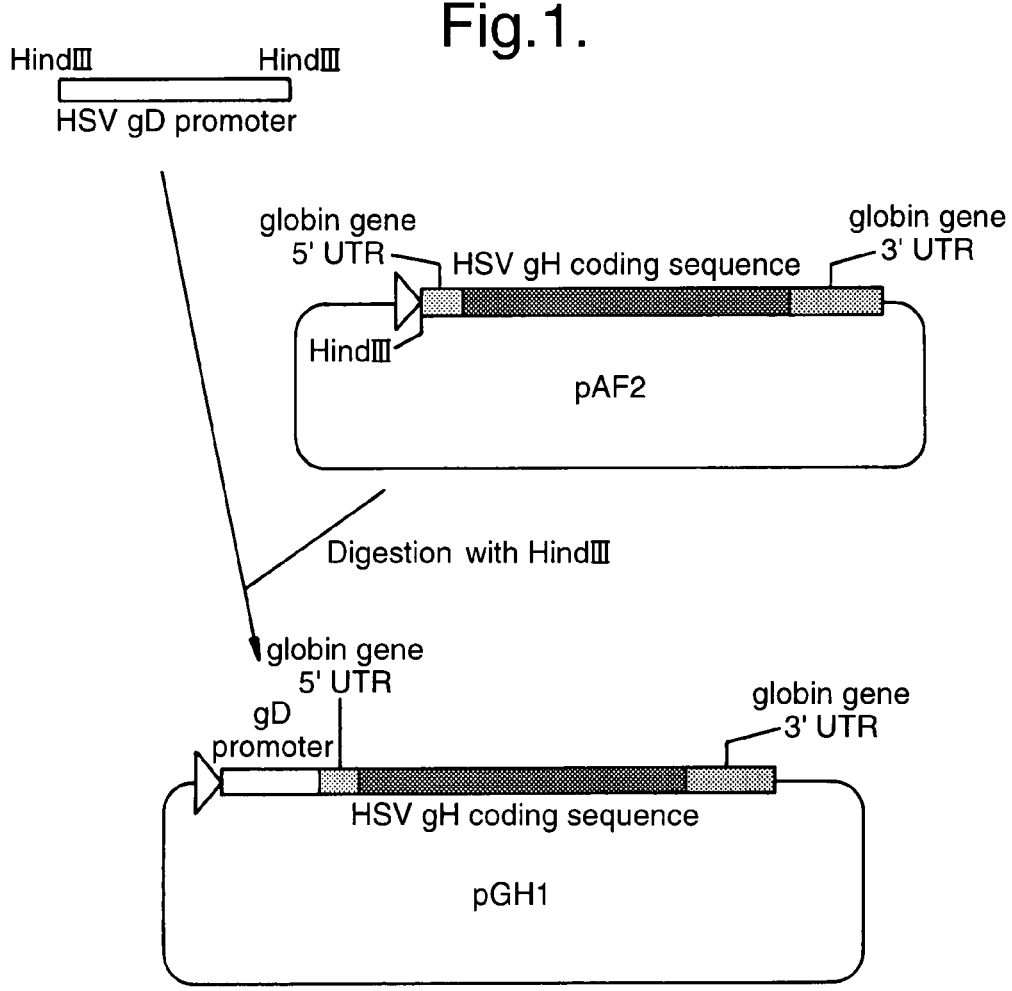
Figure 2:
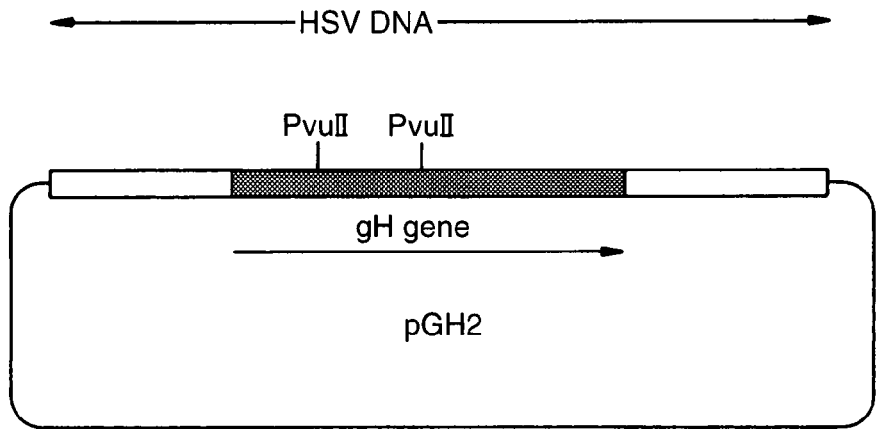

The SIV gp120 gene is first of all cloned next to the cytomegalovirus IE core promoter (U A Gompels and A C Minson, 1989, op. cit.), and subsequently a DNA cassette consisting of the gp120 gene and the upstream CMV promoter is cloned into plasmid pGH2 (FIG. 2). The resulting plasmid is then co-transfected into the gH+ complementing cell line along with DNA purified from the gH− HSV, and recombinant virus which has acquired the gp120 gene in place of the β-galactosidase gene present in the gH− HSV virus is isolated by screening for interruption of the β-galactosidase gene.

Figure 7:
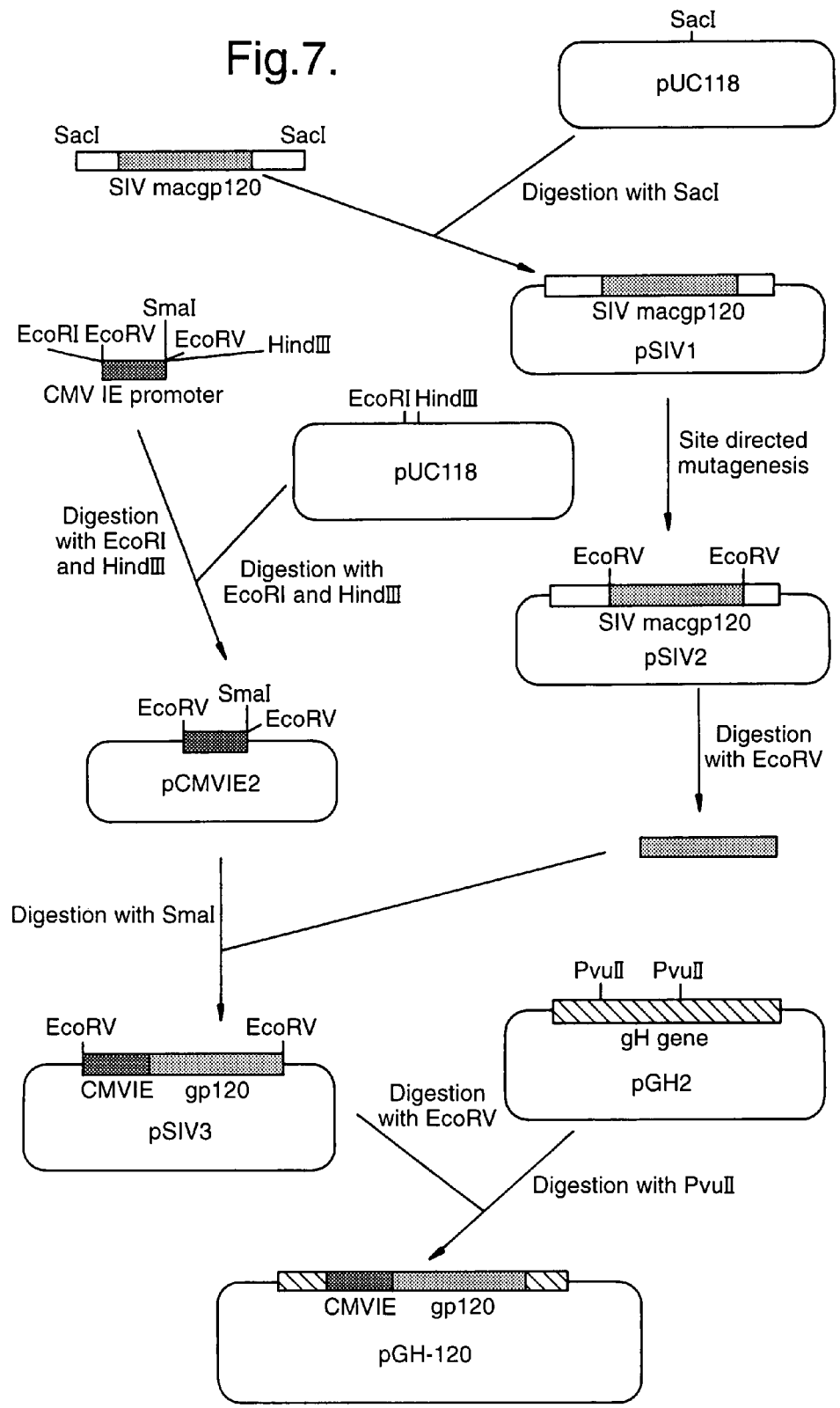
Figure 8:
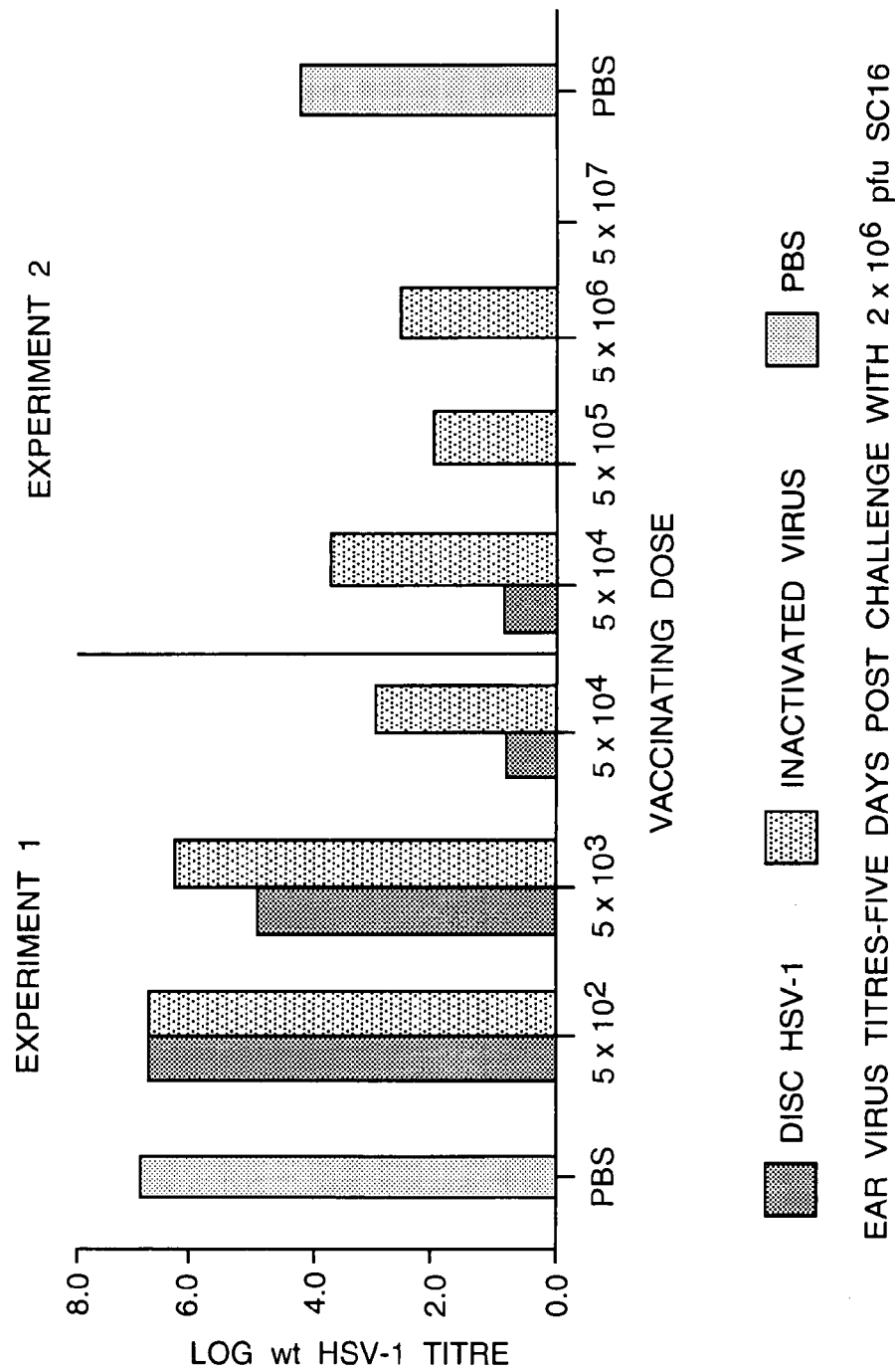
Figure 9:
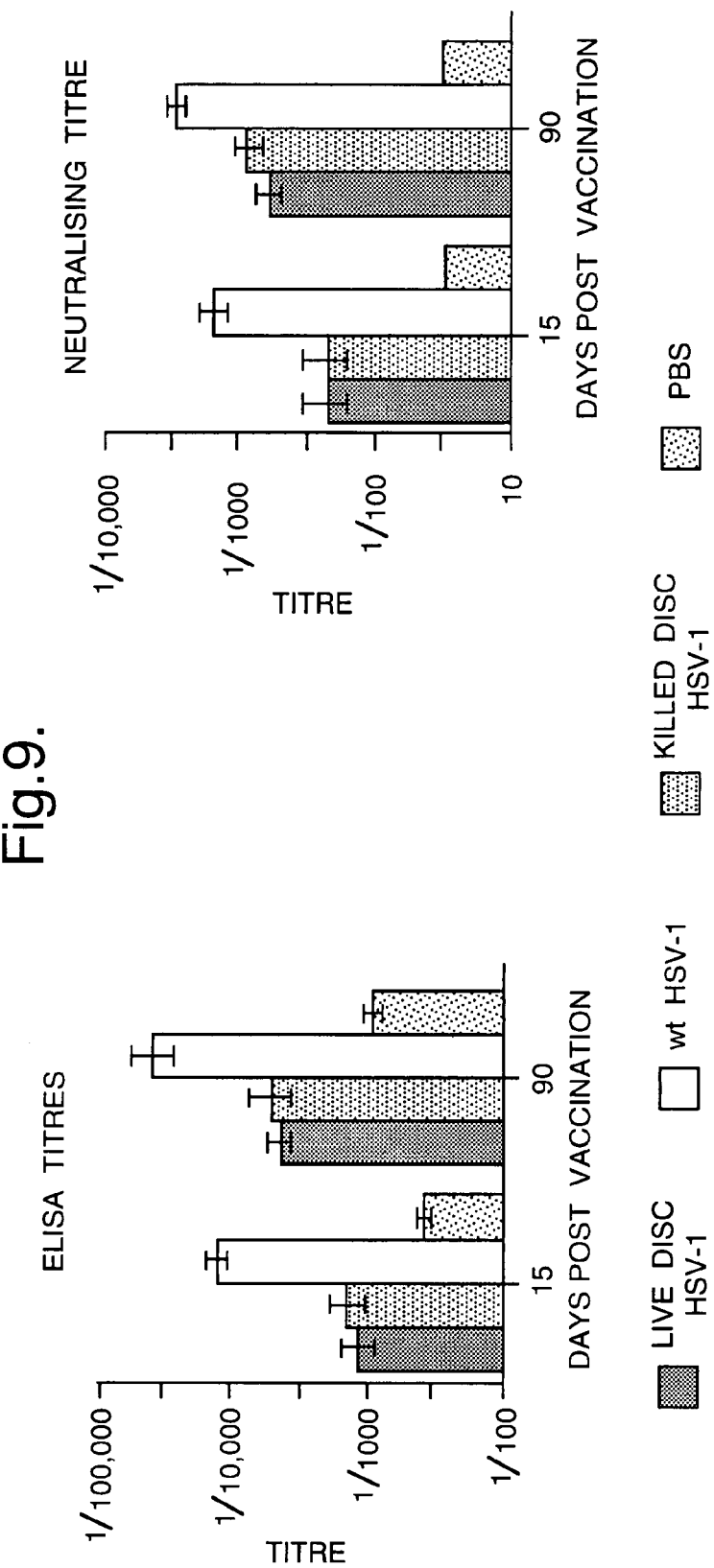
Figure 10:
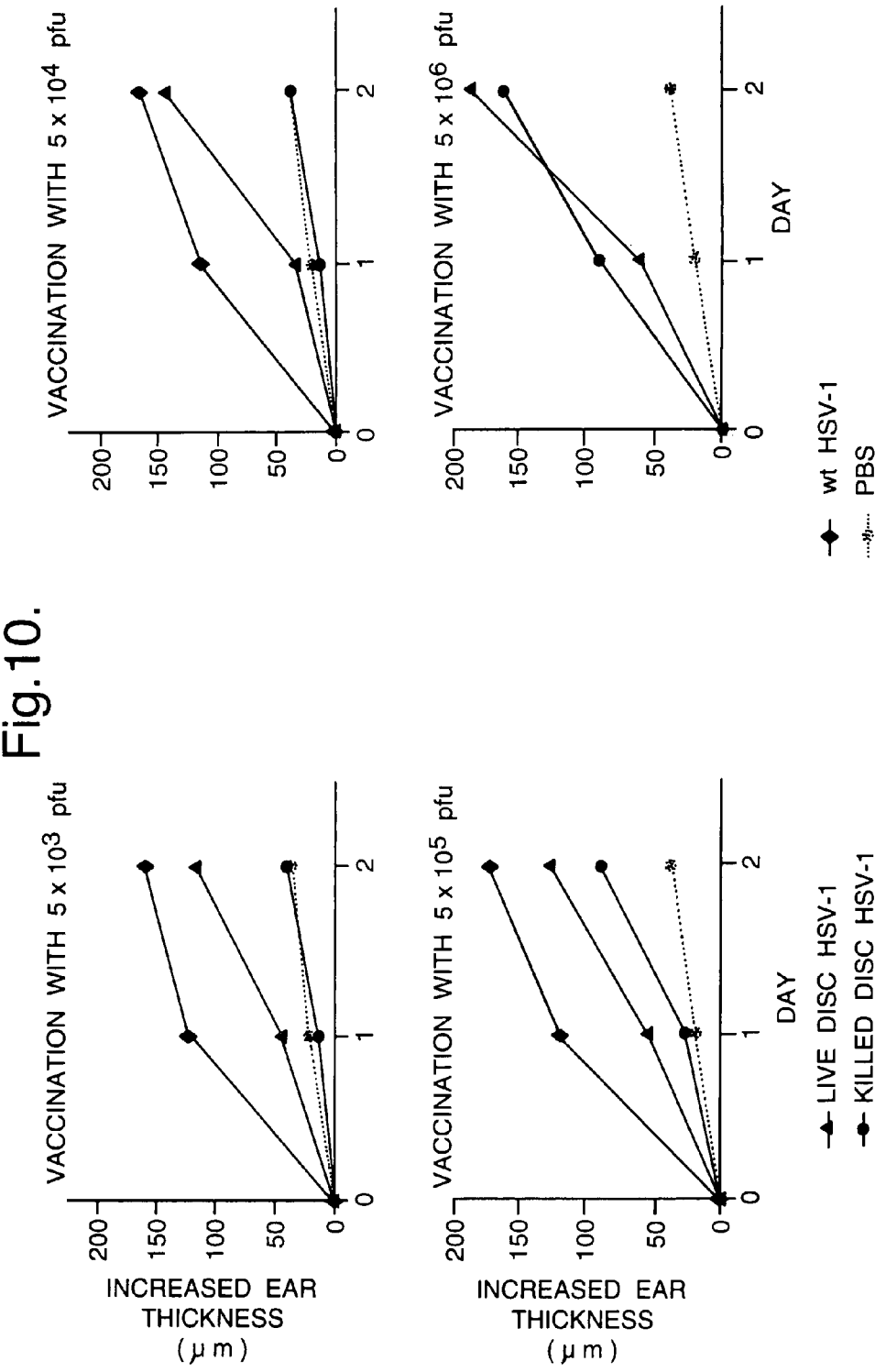

D-A. Construction of Plasmid for Recombinant of the SIV gp120 Coding Sequence into the HSV Genome The overall scheme for this procedure is shown in FIG. 7. A SacI restriction enzyme fragment (corresponding to bases 5240-8721) is excised from a cloned DNA copy of the SIV genome (L Chakrabarti et al, Nature 328 (1987), 543-547), and cloned into the SacI site of plasmid pUC118 (J Vieira and J Messing, in Methods in Enzymology, 153 (1987), 3-11) in order to generate plasmid pSIV1 which may be converted to single stranded DNA for manipulation by site directed metagenesis. This DNA region, which includes the SIV env gene (lying between 6090-8298) is then altered by site directed mutagenesis (I Brierley et al, Cell, 57 (1989), 537-547) to introduce a restriction enzyme site for the enzyme EcoRV at positions 6053-6058 using the synthetic oligonucleotide (SEQ ID NO:13)

5'GAAGAAGGCTATAGCTAATACAT.

A second EcoRV site is then introduced at position 7671-7676 within the SIV env gene corresponding to the cleavage site between the gp120 and gp40 domains of the env gene sequence, using the synthetic oligonucleotide (SEQ ID NO:14)

5'CAAGAAATAAACTATAGGTCTTTGTGC to generate the plasmid pSIV2. A DNA fragment (1617 base pairs) corresponding to the gp120 portion of the SIV env gene is then prepared by digestion of SIV2 with EcoRV.

The core region of the CMV immediate early gene promoter is obtained from the plasmid pUG-H1 (U A Gompels and A C Minson, 1989, op. cit.) by the PCR technique using the following two synthetic oligonucleotides (SEQ ID NO:15, SEQ ID NO:16).

upstream primer
5' ATC GAATTC CTATAG CCTGGCATTATGCCCAG-TACATG
EcoRI EcoRV downstream primer
5'TCA AAGCTTCTATAGCCCGGGGAGCTCTGATTATATAGACCTCCC
HindIII EcoRV SmaI The product of this reaction is then cleaved with the enzymes EcoRi and HindIII to generate a DNA fragment which is then cloned into EcoRI- and HindIII-digested plasmid pUC118 to generate the plasmid pCMVIE2 which has a unique SmaI site located just downstream of the CMV promoter sequence. The EcoRV fragment containing the $SIV_{mac}$ gp120 coding sequence prepared as described above, is then cloned into this SmaI site, and plasmid pSIV3, with the SIV coding region oriented correctly to allow expression of the coding sequence from the promoter, is then selected. This plasmid is then digested with EcoRV to yield a blunt-ended DNA fragment consisting of the SIV sequence together with the CMV promoter, which is then cloned into PvuII-digested pGH2 (FIG. 2) to produce pGH-120).

D-B. Construction of the SIV gp120 Carrying Recombinant gH− HSV

DNA is purified from the gH− HSV virus constructed as detailed in the previous section, and co-transfected into gH+ complementing cells along with purified pGH-120 DNA. Progeny virus isolated from this transfection procedure is then plated on monolayers of the gH+ complementing cell line by standard plaque assay as before using an agar overlay in the presence of X-gal. The parental gH− virus carries a functional β-galactosidase gene, located within the residual gH coding sequences, and in the presence of X-gal, will form blue plaques. Recombinant viruses however, which have acquired the SIV gp120 coding sequence in place of the β-galactosidase gene, will produce white plaques. Virus is recovered from these white plaques by picking plugs of agar, and virus stocks prepared through growth of the virus in the gH+ complementing cell line. Virus DNA is prepared from these stocks, and checked for the presence of the correct DNA structure around the gH gene by Southern Blotting using appropriate probes derived from the SIV coding sequence. Finally stocks of the virus are prepared as before for vaccination studies in animals.

Vaccines comprising the attenuated virus can be prepared and used according to standard techniques known in the art. For example, the vaccine may also comprise one or more excipients and/or adjuvants. The effective dose of the attenuated virus to be provided by the vaccine may be determined according to techniques well known in the art.

Section E. Construction of a gH Defective Recombinant Type 2 Herpes Simplex Virus (DISC HSV-2)

E-A. The HSV2 gH Gene (a) The Herpes Simplex type 2 (HSV2) gH gene is contained within two BamH1 restriction fragments of the 25766 strain of HSV2. pTW49 is the BamH1 R fragment of HSV2 strain 25766 cloned into pBR322. pTW54 is the BamH1 S Fragment of HSV2 strain 25766 cloned into pBR322. The construction of a single plasmid containing the complete gH gene is shown in FIG. 23. pTW49 was digested with BamH1 and Sall, and an 870 base pair (bp) fragment isolated from an agarose gel. Similarly pTW54 was digested with BamH1 and Kpn1 and a 2620 bp fragment isolated from an agarose gel. The two fragments were ligated together with the plasmid pUC119 cut with Sall and Kpn1, resulting in the plasmid pIMMB24.

(b) pIMMB24 was digested with Sall and Kpn1. In addition the plasmid was digested with Dra1 (which cuts in the vector sequences), to aid in isolation of the 3490 bp insert. The 3490 bp insert containing the HSV2 sequences was purified from an agarose gel. It was then sonicated, the ends repaired using T4 DNA polymerase and Klenow, and size fractionated on an agarose gel. A fraction containing DNA molecules of approximately 300-600 bp in length was ligated into M13mp11 cut with Smal (Amersham International UK). The ligated mixture was transformed into *E. coli* strain TG1, and individual plaques were picked. Single-stranded DNA was made from each plaque picked, and was sequenced using the dideoxy method of sequencing, either with Klenow enzyme or with Sequenase, and using $^{35}$S dATP.

In addition to sequencing in M13 using an oligonucleotide priming from within the M13 sequences, sequence data was also obtained by sequencing directly from the pIMMB24 plasmid using oligonucleotide primers designed from sequence already obtained. In order to obtain sequence from regions flanking the gH gene, some sequence information was also obtained from the plasmid pTW49.

Because of the high G+C ratio of HSV2 DNA, there were several sequence interpretation problems due to 'compressions' on the gels. These have yet to be resolved. In a small number of places therefore, the present sequence represents the best guess as to what the correct sequence is, based on comparisons with the previously published HSV1 sequence.

(c) The sequence of HSV2 strain 25766 (SEQ ID NO:5) in the region of the gH gene is shown in FIG. 24, along with a translation of the gH in single letter amino acid code (SEQ ID NO:6). FIG. 25 shows a comparison of the DNA sequence of HSV1 (SEQ ID NO:7) and HSV2 (SEQ ID NO:5) in this region. FIG. 26 shows a comparison of the deduced amino acid sequences of the HSV1 (SEQ ID NO:8) and HSV2 (SEQ ID NO:6) gH proteins. At the DNA level the overall identity is 77%. At the protein level the overall identity is also 77%, with a further 9.7% of amino acids being similar in properties. The degree of sequence similarity varies to some extent along the length of the gene, as can be seen from FIG. 27, which shows graphically the level of similarity. Even more marked than the variation along the gH gene is the difference in levels of identity between HSV1 and HSV2 at the DNA level between the coding and non-coding regions. As can be seen from FIG. 25, the nucleotide sequence identity is higher within the coding sequence of the gH gene than it is in the intergenic regions. FIG. 27 shows this in a graphical form, with the positions of the TK, gH and UL21 genes marked.

(d) The availability of nucleotide sequence data from around the HSV-2 gH gene enables further constructs to be made eg it allows the design of recombination vectors which enables precise deletion of the gene from the viral genome. Because of the differences between HSV1 and HSV2, particularly between the genes, may not have been possible from knowledge of the HSV1 sequence alone.

Oligonucleotides MB57 (SEQ ID NO:9), MB58 (SEQ ID NO:10), MB59 (SEQ ID NO:11), and MB75 (SEQ ID NO:17) were designed to isolate and clone the regions of sequence flanking the HSV2 gH gene. As shown in FIG. 29, the oligonucleotides were used in a polymerase chain reaction (PCR) to amplify fragments of DNA from either side of the gene. Restriction sites were included in the oligonucleotides so that the resultant fragments contained these sites at their ends, enabled cloning of the fragments into a suitably cut plasmid. The following oligonucleotides, based on the HSV2 sequence, were used for this purpose:

Hpal

Inside right MB57 (SEQ ID NO:9) TCA GTTAACGCCTCTGTTCCTTTCCCTTC

EcoR1

Outside right MB58 (SEQ ID NO:10) TCA GAATTCGAGCAGCTCCTCATGTTCGAC

Hpal

Inside left MB75 (SEQ ID NO:17) TCA GTTAACCGTCGTCCCGGCTGCCAGTC

Hind111

Outside left MB59 (SEQ ID NO:11) TCA AAGCTTCTGCAGCGCGGCGGGAGGTGG

The position of these oligonucleotides is also shown on FIG. 25.

On the basis of the description given above in relation to HSV-1 and common general knowledge, such a plasmid allows the skilled person to produce a defective HSV-2 virus lacking precisely the sequences for the gH gene (see below). If these same sequences are cloned into a suitable cell carrying a copy of the gH gene deleted from the HSV-2 genome, this 'complementing cell' can then support the growth of the defective HSV-2 virus by providing the gH protein. Because the sequences have been chosen so that there is no overlap between the sequences in the cell and the sequences in the virus, the possibility of the virus acquiring the gene from the cell by recombination is virtually eliminated.

E-B. Complementing Cell Lines

It was found that cells expressing the HSV-1 gH gene (F6 cells, see also A Forrester et al, Journal of Virology, 66 (1992), pp 341-348) can support the growth of an HSV-2 virus lacking the gH gene. However two new cell lines were made. CR1 cells use the same promoter and gH gene as F6 cells, but the sequences downstream of the gene are truncated so that there is no overlap of sequences between the final DISC virus and the cell line. This is very useful since it means that homologous recombination cannot occur between the DISC virus and the cell line DNA. In the case of F6 cells and the gH-deleted virus in the Forrester paper, where there is overlap, wild-type gH-plus viruses occur by recombination at about 1 in $10^6$ viruses. Another cell line, CR2, was also made, which expresses the gH gene from the HSV-2 strain 25766. This also supports the growth of a DISC HSV-2 and also has no overlapping sequences between the virus and the cell.

Polymerase Chain Reaction (PCR) of Flanking Sequences

Viral DNA is purified from virus by standard methods. Flanking sequences to either side of the gH gene are amplified by PCR using Vent DNA polymerase (from New England Biolabs) which has a lower error rate than Taq DNA polymerase (see FIG. 30). The oligonucleotides used for PCR include restriction site recognition sequences, as well as the specific viral sequences (see below). Two vectors are made, one for the first stage and one for the second stage of recombination. For both vectors the right hand flanking sequences start at the same position to the right of the gH gene. The first stage vector has left hand flanking sequences that, in addition to deleting the HSV-2 gH gene, also delete the 3' portion of the viral TK gene. The second stage vector has left hand flanking sequences which restore the complete TK gene, and extend right up to the 5' end of the gH gene, as desired in the final virus.

The oligonucleotides used are as follows:
HindIII

MB97 (SEQ ID NO:18) TCG AAGCTTCAGGGAGTGGCGCAGC

Hpal

MB96 (SEQ ID NO:19) TCA GTTAACGGACAGCATGGCCAGGTCAAG

Hpal

MB57 (SEQ ID NO:9) TCA GTTAACGCCTCTGTTCCTTTCCCTTC

EcoRI

MB58 (SEQ ID NO:10) TCA GAATTCGAGCAGCTCCTCATGTTCGAC

Construction of Vectors

The first stage recombination vector, pIMMB47+:

The two PCR fragments made by oligos MB97 (SEQ ID NO:18)-MB96 (SEQ ID NO:19) and by oligos MB57 (SEQ ID NO:9)-MB58 (SEQ ID NO:10) are digested with the restriction enzymes appropriate to the sites that have been included in the PCR oligonucleotides. The MB97-MB96 fragment is digested with HindIII and Hpal. The MB57-MB58 fragment is digested with Hpal and EcoRI. These fragments are then ligated into the vector pUC119 which has been digested with HindIII and EcoRI. The resultant plasmid is called pIMMB45 (see FIG. 30).

To allow for easy detection of the first stage recombinants, the *E. coli* beta-galactosidase gene, under the control of the Cytomegalovirus (CMV) immediate early promoter is inserted into pIMMB45. The CMV promoter plus beta-galactosidase gene is excised from a suitable plasmid carrying the promoter and gene using one or more appropriate restriction enzymes. If necessary, the ends are filled in using the Klenow fragment of DNA polymerase. This is the approach taken by the present applicants. However alternative methodologies will be apparent to those skilled in the art. For example, the beta-galactosidase gene may be under the control of the SV40 promoter, in which case, the gene and promoter can be excised from the plasmid pCH110 (Pharmacia PL Biochemicals) using BamHI and TthlllI, and the ends are filled in using the Klenow fragment of DNA polymerase (MS Ecob-Prince et al, J Gen Virol, 74 (1993), pp 985-994). The fragment is gel-purified. The plasmid pIMMB45 is digested with Hpal, phosphatased with Calf Intestinal Alkaline Phosphatase (CIAP) to abolish self ligation, and gel-purified. The gel-purified fragments are then ligated together to produce the plasmid pIMMB47+ (see FIG. 31).

The second stage recombination vector, pIMMB46:

The two PCR fragments made by oligos MB94-109 (SEQ ID NO:20) and by oligos MB57 (SEQ ID NO:9)-MB108 (SEQ ID NO:21) are digested with the restriction enzymes appropriate to the sites that have been included in the PCR oligonucleotides. The MB94-MB109 fragment is digested with HindIII and Hpal. The MB57-MB108 fragment is digested with Hpal and EcoRI. These fragments are then ligated into the vector pUC119 which has been digested with HindIII and EcoRI. The resultant plasmid is called pIIMB46 (see FIG. 32).

The oligonucleotides used are as follows:

EcoRI

MB108 (SEQ ID NO:21) TCA GAATTCGTTCCGGGAGCAGGCGTGGA

Hpal

MB109 (SEQ ID NO:20) TCA GTTAACTGCACTAGTTTTAATTAATACGTATGCCGT CCGTCCCGGCTGCCAGTC

E-C. Construction of Recombinant Viruses a) First Stage.

Virus DNA was made from strain HG52-D, which is a plaque-purified isolate of the HSV-2 strain HG52. Virus DNA (2.5 μg) and pIMMB47+ plasmid DNA (0.25 μg) was transfected into CR1 cells using the $CaPO_4$ precipitation method (Chen & Okayama, Molecular and Cellular Biology, 7, p. 2745). Recombination takes place within the cells, and a mixture of recombinant and wild type virus is produced. The mixture was plaque-purified three times on CR1 cells in the presence of acyclovir (10 μg/ml), to select for TK-minus virus. A single plaque was then grown up and analysed. The virus was titrated on normal Vero cells and on CR1 cells. If the virus is a gH-deleted virus, it should only grow on CR1 cells and not on Vero cells. Table E-1 shows that this is the case. It can be seen that the virus does not grow at all on the non-complementing Vero cells even at the highest virus concentrations, but does grow well on the CR1 complementing cell line, which expresses the HSV-1 gH gene. The virus also grows well on CR2 cells which express the HSV-2 gH gene (data not shown).

TABLE E-1

Growth of first stage recombinant virus on complementing (CR1) and non-complementing (Vero) cells.

| | CR1 (gH+) | | | Vero | | | |
|---|---|---|---|---|---|---|---|
| Virus dilutions | $10^{-4}$ | $10^{-5}$ | $10^{-6}$ | $10^{-1}$ | $10^{-2}$ | $10^{-3}$ | $10^{-4}$ |
| Numbers of | >350 | 174 | 22 | 0 | 0 | 0 | 0 |
| plaques | >350 | 169 | 19 | 0 | 0 | 0 | 0 | b) Second Stage.

DNA was made from this TK-minus DISC virus and a recombination was carried out as above with the plasmid pIMMB46. In this case TK-plus recombinants were selected, on a gH-expressing TK-minus BHK cell line, by growth in medium containing methotrexate, thymidine, glycine, adenosine and guanosine. Virus was harvested and grown again under selective conditions twice more before a final plaque purification was carried out on CR1. Virus was grown up and analysed by Southern blotting. Virus DNA from the original HG52-D, the TK-minus DISC virus, and the TK-plus DISC virus were digested with BamHI and separated on an agarose gel. The DNA bands were then transferred to nylon membrane by the Southern blotting method, and probed with radiolabelled fragments from the right hand flanking sequences. FIG. 33 shows the structures of these viruses, with the expected band sizes after BamHI digestion. The probe used is marked as 'R' beneath a dashed line. The probe should hybridise to a different size band in each of these viruses, as follows:

| Virus | Band size hybridising (base pairs) |
|---|---|
| HG52-D | 3481 |
| TK-minus "first stage" DISC virus | 3140 |
| TK-plus "second stage" DISC virus | 4225 |

FIG. 34 shows that this is the case. Lane 5 shows the HG52-D virus, Lane 2 contains the TK-minus "first stage" DISC virus, and lanes 3, 4, 6, 7 and 8 contain TK-plus "second stage" DISC viruses. This confirms that the DNA structure in each of these viruses is as expected.

The defective HSV-2 can be used as a vaccine. After growth in the complementing cell line, the HSV-2 virus is phenotypically identical to a wild type HSV-2 virus, and can infect cells in a normal manner. In normal cells the defective HSV-2 virus undergoes a single cycle of replication. Viral particles are produced, but because normal cells do not express the gH gene, these HSV-2 viral particles lack the gH protein, and are subsequently unable to infect further cells.

Furthermore the sequence of the HSV-2 gH gene as hereby provided can be very useful for several purposes. In the context of the DISC virus system, it can be useful in that the detailed knowledge of the sequence allows the making of precise deletions around the gH gene. In addition, should it prove desirable to use the HSV-2 gH gene in the complementing cell line, either to provide better complementation of the gH-deleted virus, or to produce a type 2 DISC virus with improved immunogenicity, then again the sequences will prove invaluable. Uses in different areas can also be envisaged, such as subunit vaccines using the HSV-2 gH protein as an immunogen, or recombinant viruses (either HSV or other viruses) expressing the HSV-2 gH gene. For diagnostic purposes PCR primers can be designed using the HSV-2 gH sequence, in order, if desired, to distinguish between HSV-1 and HSV-2.

Section F. In Vivo Mouse Studies

Protection Studies

The in vivo mouse ear model was used to study prophylactic effects. Equivalent doses of inactivated wild-type ('w.t.') HSV-1 (strain SC16, see T J Hill et al, J Gen Virol. 28 (1975), pp 341-353) and DISC HSV-1 were compared for their effect on the replication of w.t. HSV-1, their ability to provide protection against w.t. HSV-1 challenge and to induce HSV-specific neutralising antibodies.

4-5 week old BALB/c mice were vaccinated with varying doses of DISC HSV-1 or inactivated virus by scarification in the left ear pinna. Virus was inactivated using β-propiolactone (see description above in relation to HSV-1). The mice were challenged with $2\times10^6$ pfu w.t. HSV-1 (strain SC16) in the opposite ear two weeks after vaccination. The amount of virus present in that ear 5 days post challenge was assayed by plaquing on BHK cells. (See FIG. 8.)

It can be seen from FIG. 8 that vaccination with $5\times10^5$ and $5\times10^6$ pfu DISC HSV-1 (pfu measured on complementing cell line for DISC viruses) led to complete protection against replication of the challenge virus, whilst mice vaccinated with inactivated virus still had live challenge virus present.

A similar result was obtained when virus titres were assayed from the ganglia of vaccinated animals 5 days after challenge (data not shown).

Serological Response to Disc HSV-1 Vaccination

The role of antibody in protection conferred by the DISC HSV-1 vaccination was investigated. Both neutralising antibody titres and total antibody titres, as determined by ELISA, were measured.

Groups of 6 mice were vaccinated with $5\times10^5$ pfu of DISC HSV-1, killed DISC HSV-1, w.t. HSV-1 (strain SC16) or with PBS and serum samples taken at 2 and 14 weeks post vaccination. Neutralising antibodies were measured in the presence of complement and expressed as the inverse of the serum dilution which reduced the number of plaques by 50%. ELISA antibody titres were measured on plates coated with HSV-1 infected BHK cell lysates and titrated to end-point. (See FIG. 9.)

It can be seen from FIG. 9 that no significant differences in antibody titres were observed between animals vaccinated with DISC HSV-1 and an equivalent amount of killed DISC HSV-1.

Delayed-Type Hypersensitivity (DTH) Response to Disc HSV-1 Vaccination

The importance of a DTH response in protection against herpes virus infection has been well documented. The ability of, the DISC HSV-1 to raise a DTH response was investigated by vaccinating groups of mice with DISC HSV-1, killed DISC HSV-1, and live w.t. HSV-1, by scarification of the left ear pinna. Four doses ($5\times10^3$, $5\times10^4$, $5\times10^5$ and $5\times10^6$ pfu) of vaccine were used, and two weeks later the vaccinated animals were challenged in the opposite ear with $10^6$ pfu w.t. HSV-1 (strain SC16). The DTH response at the site of challenge was assessed by measurement of ear thickness at 24 and 48 hours post challenge and expressed as the difference between the challenged and unchallenged ears. (See FIG. 10.)

It can be seen from FIG. 10 that at low vaccine doses ($5\times10^3$, $5\times10^4$ pfu), no DTH response was observed with killed DISC HSV-1, whilst a clear DTH response was demonstrated after DISC HSV-1 vaccination. At high doses (eg $5\times10^6$ pfu), both the DISC HSV-1 vaccine and killed DISC HSV-1 preparations induced similar DTH responses.

The DTH responses induced by different doses of the various vaccine preparations thus correlate with their protective effect against challenge virus replication. The efficacy of vaccination with low doses of the DISC HSV-1 vaccine may therefore be due to the induction of T cell-mediated immunity.

Demonstration that Disc HSV Type 1 Virus is Capable of Generating Cytotoxic T Cells Cytotoxic T cells have been shown to be involved in the protection against, and recovery from, primary HSV infection. DISC HSV-1 vaccinated mice were therefore studied for the presence of HSV-1 specific cytotoxic T cell activity.

Cytotoxic T cell activity following immunisation was generated and assayed according to standard procedures eg as exemplified in S Martin et al, J Virol, 62 (1988), 2265-2273, and W S Gallichan et al, J Infect Dis, 168 (1993), 622-629. More specifically, groups of female BALB/c mice were immunised intra-peritoneally with $2\times10^7$ pfu of virus (DISC HSV-1; killed DISC HSV-1; MDK a thymidine kinase negative HSV-1 strain) on day 0 and the immunisations repeated (same dose and route) after 3 weeks. A group of control mice received 0.1 ml of PBS intraperitoneally at the same time points. Ten days after the second immunisation the spleens of the mice were removed and pooled for each group.

Spleens were also removed from unimmunised BALB/c mice for the preparation of feeder cells (16 feeder spleens being sufficient for 4 groups of six effector spleens). All subsequent steps were performed in a laminar flow hood using aseptic technique. The spleens were passed through a sterile tea-strainer to produce a single cell suspension in RPMI 1640 medium supplemented with 10% heat inactivated foetal calf serum (effector medium). Debris was allowed to settle and the single cell suspension was transferred to a fresh container. The cell suspensions were washed twice in effector medium (1100 rpm, 10 minutes) and then passed through sterile gauze to remove all clumps. The effector spleen cell suspensions were then stored on ice until required.

Feeder spleen cells were resuspended to $1 \times 10^7$ cells/ml in effector medium and mitomycin C was added to a final concentration of 20 μg/ml. The feeder cells were incubated at 37° C. for 1 hour. Feeder cells were washed four-times in PBS supplemented with 1% FCS and once in PBS with no protein. Live virus (MDK) was added to the mitomycin C treated feeder cell pellet at a concentration of 3 pfu of virus per spleen cell. Following a one hour incubation at 37° C. the feeder cells were washed once with effector cell medium.

Effector cells were resuspended to $5 \times 10^6$ cells/ml, whilst feeder cells were resuspended to $2.5 \times 10^6$ cells/ml. 500 μl of effector cell suspension and 500 μl feeder cell suspension were added to the wells of a 24 well plate. The plates were incubated in a humid atmosphere at 37° C. (5% $CO_2$) for 4 days.

The effector and feeder cells were harvested from the 24 well plate. The cells were spun down once and the pellet resuspended in effector medium (5 ml of medium per 2 plates). The cell suspension was layered onto lymphocyte separation medium and spun at 2500 rpm for 20 minutes. The live effector cells were harvested from the interface and washed twice, once at 1500 rpm for 15 minutes and once at 1100 rpm for 10 minutes. The effector cells were finally resuspended at the required concentration in effector medium and stored on ice until required.

Labelled target cells were prepared for the cytotoxicity assay. Uninfected syngeneic A202J target cells A20/2J cells were harvested from tissue culture flasks: $2 \times 10^7$ cells were added to each of 2 containers (to become infected and uninfected targets). The cells were washed with DMEM (with no additions). To the infected cells live MDK virus was added at 10 pfu per cell and an equivalent volume of EMEM was added to the uninfected cells. One mCi of 51Cr was added to each of the universals and the cells were incubated at 37° C. (in a waterbath) for 1 hour. The target cells were then washed three times (10 minutes, 1100 rpm) in target medium (DMEM supplemented with 10% FCS) and finally resuspended to the required cell concentration in target cell medium. Both uninfected and infected target cells were resuspended to $1 \times 10^6$ cells/ml and $1 \times 10^5$ cells/ml and 100 μl (ie to give $1 \times 10^5$ targets/well and $1 \times 10^4$ targets/well respectively) was plated out into the appropriate wells of a round bottomed 96 well plate. All experimental points were set up in quadruplicate. Each effector cell type was resuspended to $8 \times 10^6$ cells/ml in effector medium and two-fold dilutions were prepared. 100 μl of the effector cell suspensions were added to the wells containing the labelled target cells to give $8 \times 10^5$ effector cells/well, $4 \times 10^5$ effector cells/well, $2 \times 10^5$ effector cells/well and $1 \times 10^5$ effector cells/well. Thus with $10^5$ target cells per well, effector to target ratios were: 8:1, 4:1, 2:1 and 1:1. With $10^4$ target cells per well the effector to target ratios were 80:1, 40:1, 20:1 and 10:1. Maximum chromium release for each target cell type was obtained by adding 100 μl of 20% Triton X-100 to wells containing target cells only (ie no effectors). The spontaneous release for each target cell type was obtained by the addition of 100 μl effector cell medium to wells containing target cells only.

The plates were incubated at 37° C. for four hours in a humid atmosphere. After this time the plates were spun for four minutes at 1500 rpm and 100 μl of supernatant was removed from each of the wells. The supernatant was transferred to LP2 tubes and radioactivity contained in the tubes was then counted for 1 minute on a gamma counter. The % specific chromium release was determined using the formula $$\% \text{ specific release} = \frac{\text{Exp. mean cpm} - \text{spon. mean cpm}}{\text{Max. mean cpm} - \text{spon. mean cpm}} \times 100$$

Exp. = Experimental

Spon. = Spontaneous

Max. = Maximum

Figure 11:
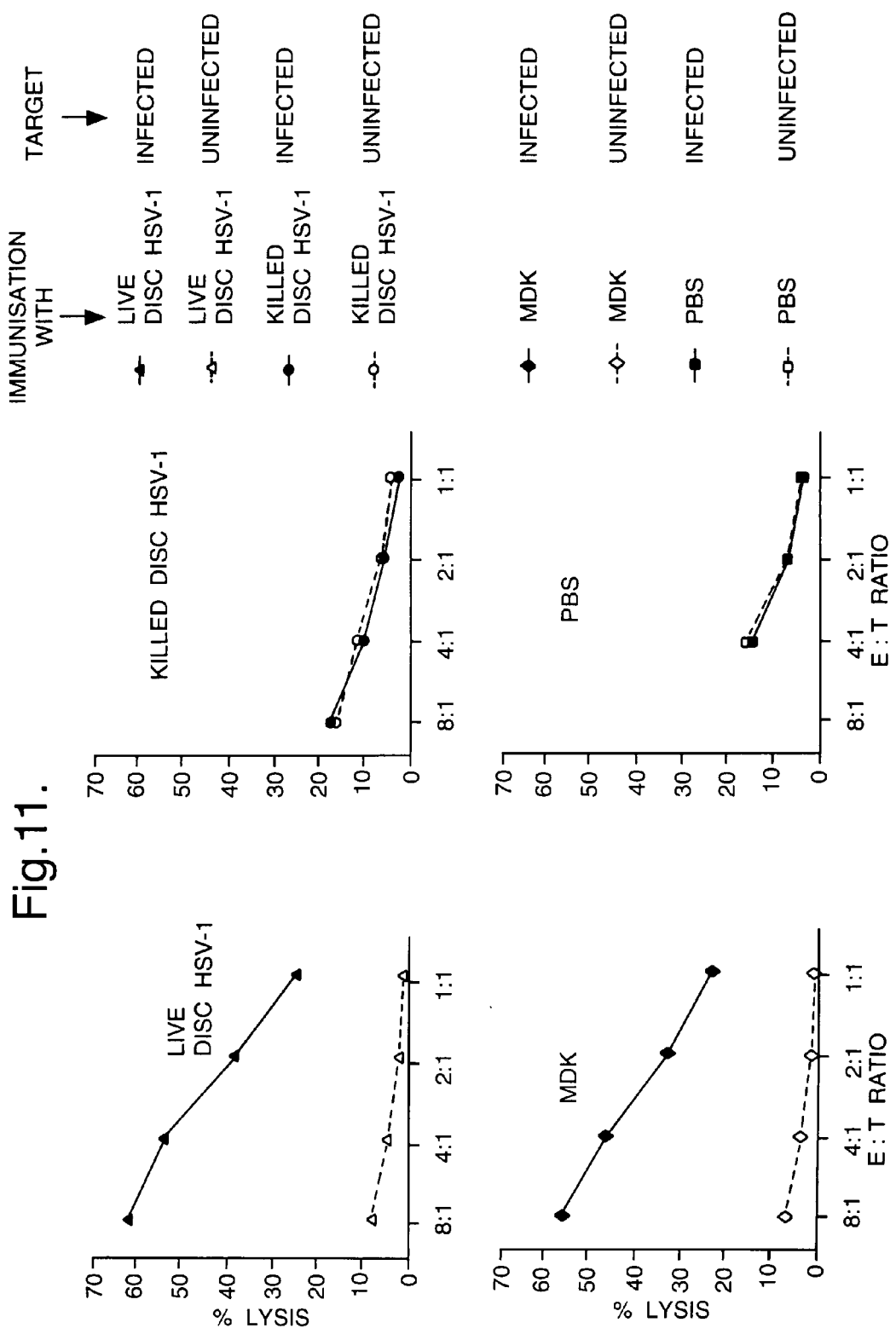

The results are shown in FIG. 11 and Table F-1

TABLE F-1

| E:T ratio | DISC HSV-1 | Inactivated Virus | MDK | Unvaccinated |
|---|---|---|---|---|
| 8:1 | 53.9 | 1.5 | 48.3 | ND |
| 4:1 | 49.6 | 0.0 | 42.2 | 0.0 |
| 2:1 | 36.9 | 0.0 | 31.0 | 0.0 |
| 1:1 | 23.9 | 0.0 | 21.9 | 0.0 |

% HSV-1 Specific Lysis (% lysis of HSV-infected cells minus % lysis of uninfected cells).

DISC HSV-1 vaccination induced HSV-1 specific CTL activity comparable to that produced by infection with the fully replicative MDK virus. In contrast no HSV-1 specific CTL activity was observed in mice immunised with killed DISC HSV-1 or in PBS treated animals, although some non-specific killing was observed in these animals. The reason for this is not clear, but it could represent a high level of NK cell activity.

Vaccination of mice with the DISC HSV-1 has thus been shown to induce antibody, CTL and DTH activity against HSV-1 virus antigens. The ability to activate both humoral and cell-mediated immune responses against a broad spectrum of virus proteins may explain the effectiveness of the DISC virus vaccination.

Long-Term Protection

The in vivo mouse ear model was used to study long term prophylactic effect of DISC HSV-1

4-5 week old BALB/c mice were divided into groups containing 6 animals each.

The groups were vaccinated as follows:

| Group | Vaccination |
|---|---|
| PBS | Mock immunisation with PBS |
| 1K | 1 immunisation with inactivated DISC HSV-1 |
| 2K | 2 immunisations with inactivated DISC HSV-1 |
| 1L | 1 immunisation with (live) DISC HSV-1 |
| 2L | 2 immunisations with (live) DISC HSV-1 |
| 1S | 1 immunisation with w.t. HSV-1 (strain SC16) |
| 2S | 2 immunisations with w.t. HSV-1 (strain SC16) |

All groups were immunised by scarification of the left ear pinna with $5\times10^5$ pfu on day 0 and blood samples taken on days 15, 27, 90, 152 and 218. Groups PBS, 2K, 2L and 2S received additional immunisations of PBS or $5\times10^5$ pfu on day 20. All groups were challenged with $5\times10^5$ w.t. HSV-1 (strain SC16) on day 223. The amount of virus present in the challenged ear (right) 5 days post challenge was assayed by plaquing on BHK cells. The results as depicted by FIG. 20 show that two vaccinations with DISC HSV-1 (group 2L) provides goods protection compared to inactivated DISC HSV-1 (group 2K), but that better protection was obtained with w.t. HSV-1 (strain SC16). The efficacy of vaccination with w.t. HSV-1 is of course, to be expected. However the use of normal live viruses as vaccines is generally undesirable. FIG. 21 shows the neutralising antibody titres induced by the various vaccinations. This shows that since 2 doses of DISC HSV-1 produce the same titre as two doses of the inactivated DISC HSV-1, the protective effect of DISC HSV-1 cannot be simply explained by antibody induction.

Prophylactic Effect of Disc HSV-2

The in vivo mouse ear model was used to study the prophylactic effect of DISC HSV-2.

Six week old BALB/c mice were divided into groups. They were immunised by scarification of the left ear pinna as follows.

| Group | Vaccination Material and Dose |
| --- | --- |
| 1 | $5\times10^2$ pfu live DISC HSV-2 |
| 2 | $5\times10^3$ pfu live DISC HSV-2 |
| 3 | $5\times10^4$ pfu live DISC HSV-2 |
| 4 | $5\times10^5$ pfu live DISC HSV-2 |
| 5 | $5\times10^2$ pfu killed DISC HSV-2 |
| 6 | $5\times10^3$ pfu killed DISC HSV-2 |
| 7 | $5\times10^4$ pfu killed DISC HSV-2 |
| 8 | $5\times10^5$ pfu killed DISC HSV-2 |
| 9 | $5\times10^4$ pfu w.t. HSV-2 (strain HG52) |
| 10 | $5\times10^5$ pfu w.t. HSV-2 (strain HG52) |
| 11 | PBS |

(The DISC HSV-2 was a gH deletion mutant of strain HG52.)

Three weeks later, all groups were challenged by scarification of the right ear pinna with $5\times10^4$ of w.t. HSV-2 (strain HG52).

The amount of virus present in the challenged ear (right) 5 days post challenge was assayed by plaquing on BHK cells (see FIG. 22). The results as depicted by the figure show that vaccination with DISC HSV-2 at doses of $5\times10^3$, $5\times10^4$ and $5\times10^5$ pfu provides good protection against challenge with w.t. HSV-2 (strain HG52) compared to killed DISC HSV-2. However and as is to be expected, better protection was obtained with w.t. HSV-2 at doses of $5\times10^4$ and $5\times10^5$ pfu, but the use of normal live wild type viruses as vaccines is undesirable.

Section G. In Vivo Guinea Pig Studies

As mentioned earlier, HSV-2 appears to be closely associated with genital lesions. The guinea pig currently provides the best animal model for primary and recurrent genital disease in humans (L R Stanberry et al, J Infect Dis 146 (1982), pp 397-404).

Therefore the applicants have extended the above-described mouse studies to the guinea pig vaginal model of HSV-2 infection which provides a useful system to assess the immunogenicity of candidate vaccines against genital HSV-2 infection in humans. It permits a comprehensive assessment of primary clinical symptoms following intravaginal challenge with HSV-2, and also analysis of the frequency of subsequent recurrences.

(1) Groups of 14 animals were immunised with two doses of the DISC HSV-1 vaccine ($2\times10^7$ pfu, 3 weeks apart) either by non-traumatic introduction into the vagina (intravaginal route), or by scarification of the ear pinna (intraepithelial route). A control group of 21 animals was vaccinated intra-vaginally with a mock virus preparation and a further group of 14 animals was vaccinated intra-epithelially with two equivalent doses of β-propiolactone-inactivated w.t. HSV-1.

Vaccinated animals were challenged 3 weeks later with $10^{5.2}$ pfu w.t. HSV-2 virus (strain MS) and monitored for the symptoms of primary and recurrent disease.

(a) Following w.t. HSV-2 challenge, animals were assessed daily over a two week period for symptoms of primary infection. Clinical lesions were scored as a direct numerical value, and erythema was scored on a scale of 1-5. The vaginal area was also measured as an index of oedema (data not shown). The results are shown in FIGS. 12 and 13. Points on the graphs represent mean erythema score per animal per day (FIG. 12) and mean total lesion score per day per animal (FIG. 13).

The results show that intra-epithelial and intra-vaginal vaccination with the DISC HSV-1 both provided a high degree of protection against the primary symptoms of HSV-2 infection. Surprisingly, inactivated HSV-1 administered by the intra-epithelial route also provided substantial protection, though apparently less than that afforded by the DISC virus vaccine.

(b) Daily vaginal swabs were taken from all animals over a 12 day period post-challenge and virus titres determined by plaquing on Vero cells in order to monitor growth of the challenge virus in the vagina. The results as depicted in FIG. 14 shows that infection virus titres in mock-vaccinated animals rose to a maximum of $3\times10^4$ at day 2 post challenge, and could be detected until day 10. By contrast, virus titres in the vaccinated animals declined steadily from day 1, and were undetectable by day 7. No significant different was observed between the groups immunised with the DISC HSV-1 or the inactivated virus preparation.

(c) Following HSV-2 challenge, animals which had fully recovered from the acute phase of disease by 28 days were monitored daily for a further 100 days for the recurrence of disease. Numbers of animals in each group were: DISC/Intra-vaginal—14; DISC/Intra-epithelial—12; Inactivated/Intra-epithelial—14; Mock/Intra-vaginal—12. Clinical lesions were scored as a direct numerical value, and erythema was scored on a scale of 1-5. The results are shown in FIGS. 15*a* and 15*b*. Points on the graphs represent the cumulative totals of mean values per day per animal.

The results show that animals vaccinated with the DISC HSV-1 by the intra-vaginal route showed approximately a 50% reduction in the number of recurrent HSV-2 lesions occurring over the 100 day follow-up period. Intra-epithelial vaccination with DISC HSV-1 and inactivated virus also resulted in a reduction of recurrent lesions, but to a lesser extent.

(2) The following experiment was also designed to assess the immunogenicity of candidate DISC vaccines based on HSV-1 against genital HSV-2 infection. The experiment was designed to compare different vaccination routes (per vaginum, oral and nasal ie different mucosal surfaces) and different doses of either DISC HSV-1 or inactivated HSV-1 in the guinea pig.

Materials and Methods

Virus:

(i) DISC HSV-1 was propagated on Vero cells (F6) which had been transfected with the HSV-1 gH gene as described above. Briefly, confluent monolayers of F6 cells were infected with DISC HSV-1 at a multiplicity of 0.1 pfu per cell and harvested when 90-100% cpe was observed. Cells were harvested with a cell scraper, pelleted by centrifugation and the pellet resuspended in a small volume of Eagles Minimum Essential Medium (EMEM). The suspension was sonicated for 1 minute and stored in aliquots at −70° C. Virus titres were determined on F6 cells.

(ii) DISC HSV-1 was inactivated by the addition of β-propiolactone at a concentration of 0.05% for one hour at room temperature. Inactivation was checked by adding the virus to F6 cells.

(iii) HSV-2 strain MS was propagated and titred on Vero cells in the same manner as DISC HSV-1 as described above.

Animals: Female Dunkin-Hartley guinea-pigs (300-350 g) were obtained from Davis Hall, Darley Oaks Farms, Newchurch, Nr. Burton-on-Trent.

Experimental design: Groups of 12 animals were immunised with two doses of $8 \times 10^6$ pfu DISC HSV-1 or with equivalent doses of inactivated DISC HSV-1, on days 1 and 17 of the experiment. Immunisation was performed with either 0.05 ml of virus intravaginally, with 0.2 ml of virus intranasally or with 0.2 ml virus orally. A control group of 12 animals was vaccinated intravaginally with a mock preparation of virus consisting of sonicated Vero cells. All groups were challenged intravaginally on day 34 with $10^{5.2}$ pfu HSV-2 (strain MS) and the experiment blinded by randomisation of the cages by an independent worker. For a period of 11 days following challenge, animals were monitored for the symptoms of primary disease. Clinical observations were scored as the number of lesions present in the vaginal area and the presence of erythema (scored on a scale of 1-5). In addition, daily vaginal swabs were taken from all animals over a 12 day period post challenge and virus titres were determined by plaquing on Vero cells in order to monitor growth of the challenge virus in the vagina.

Statistical methods: Differences in group clinical scores were tested for significance using the Mann-Whitney U test. Values of $p<0.1$ were considered significant.

Results:

Clinical disease profile. The mean lesion score per animal, the mean erythema score and the effect of vaccination on post challenge virus replication for each of the immunisation groups are shown in FIGS. 16, 17 and 18 respectively. As compared to mock vaccinated animals, vaccination with DISC HSV-1 by the intravaginal route provided a high degree of protection from primary symptoms of infection. In contrast, vaccination with inactivated DISC HSV-1 at an equivalent dose did not lead to any significant protection.

Intranasal immunisation with DISC HSV-1 resulted in an even higher degree of protection than intravaginal vaccination. This was particularly apparent when looking at the number of days with severe disease, as defined by a lesion score of 6 or more (see table G-1). Inactivated DISC HSV-1 gave some protection via the intranasal route, but it was not as effective as vaccination with DISC HSV-1.

Vaccination via the oral route also led to protection, but to a lesser degree than intranasal or intravaginal vaccination. Again vaccination with DISC HSV-1 virus protected more efficiently than vaccination with inactivated DISC HSV-1.

TABLE G-1

INCIDENCE OF PRIMARY DISEASE SYMPTOMS

| Immunisation with | Any disease symptoms (% of animals) | Lesion score >5 (% of animals) | Duration of disease (mean no. days) | Disease ongoing on day 11 (% of animals) |
|---|---|---|---|---|
| mock | 92 | 75 | 6.8 | 75 |
| DISC HSV-1 i.vag | 33 | 17 | 4.5 | 8 |
| HSV-1 inactivated i.vag | 92 | 67 | 6.2 | 83 |
| DISC HSV-1 i.nas | 33 | 0 | 2.3 | 0 |
| HSV-1 inactivated i.nas | 67 | 17 | 6.3 | 42 |
| DISC HSV-1 oral | 90 | 20 | 4.1 | 20 |
| HSV-1 inactivated oral | 91 | 36 | 5.8 | 64 |

Thus the following conclusions can be drawn from this experiment with the in vivo guinea pig model.

A. Vaccination with DISC HSV-1 via the intravaginal and intranasal routes led to a high degree of protection from acute disease symptoms following a challenge with HSV-2.

B. Intranasal administration of DISC HSV-1 gave the highest degree of protection when considering the number of days of severe disease (as defined by the presence of 6 or more lesions).

C. Intravaginal vaccination with inactivated virus resulted in clinical disease symptoms similar to those observed in mock-infected guinea-pigs. Intranasal vaccination with inactivated DISC HSV-1 gave a significant degree of protection, but not as high as DISC HSV-1 vaccination via this route.

D. A significant difference was observed between disease symptoms in animals vaccinated orally with DISC HSV-1 and mock-infected animals. However, this degree of protection was less than that observed in animals vaccinated with DISC HSV-1 via the intranasal or intravaginal route.

E. Symptoms in animals vaccinated orally with inactivated DISC HSV-1 were not significantly different from those in the mock-infected group.

F. The data on shed virus is interesting. Surprisingly the per vaginum vaccination route resulted in significantly lower levels of recovered virus following the challenge dose. This may be due to local antibody production.

(3) The following experiment was designed to investigate HSV-2 induced recurrent disease following therapeutic vaccination.

This was of interest as it has previously been shown that therapeutic administration of certain recombinant HSV-2 antigens, together with adjuvant, can decrease the frequency of subsequent recurrences (see L R Stanberry et al, J Infect Dis 157 (1988), pp 156-163; L R Stanberry et al, J Gen Virol, 70 (1989) pp 3177-3185; and R J Y Ho et al, J Virol, 63 (1989), pp 2951-2958).

Accordingly 21 animals which had recovered fully from primary HSV-2 disease four weeks after challenge were randomised into three groups, and treated with live DISC HSV-1 intravaginally (10 animals), or intra-epithelially (11 animals). A group of 12 animals, which had previously acted as controls for prophylactic vaccination (see (2) above) and which had also recovered fully from primary disease were treated with an equivalent mock preparation (12 animals). The animals were given further identical treatments 24 and 48 days later. The frequency of recurrent disease was monitored from the day of first treatment for a further 100 days, and the cumulative results are shown in FIG. 19 and summarised in Table G-2 below.

TABLE G-2

Effect of therapeutic vaccination on recurrent disease

|  | Mock | | DISC HSV-1 Intra-epithelial | | DISC HSV-1 Intra-vaginal | |
| --- | --- | --- | --- | --- | --- | --- |
|  | Total | % of Mock | Total | % of Mock | Total | % of Mock |
| 1 Mean total disease/days per animal | 9.41 | 100 | 6.90 | 73 | 7.32 | 78 |
| 2 Mean total episodes per animal | 6.27 | 100 | 4.67 | 74 | 5.10 | 81 |
| 3 Disease incidence | 12/12 | 100 | 9/11 | 82 | 10/10 | 100 |
| 4 Severity per episode | 3.21 | 100 | 3.00 | 93 | 2.86 | 89 |
| Mean duration of episode (days) | 1.49 | | 1.27 | | 1.38 | |

1 Total number of days where disease was observed (either lesions or erythema) over the whole observation period (100 days from 1 month after challenge with HSV-2)
2 Total of days disease episodes over the whole observation period (episode length defined as period between two consecutive disease-free days
3 Proportion of animals showing any lesion or erythema score during whole observation period
4 Total sum of erythema scores and lesion numbers over the whole observation period divided by number of episodes observed It can be seen that each of the groups treated with DISC HSV-1 appeared to experience a modest reduction (about 25%) in the overall number of disease/days and episodes especially over the 50 day period following second vaccination.

Sera were collected from these animals at the end of the 100 day observation period. The ELISA and NT antibody titres in the sera were not significantly higher than those recorded post-challenge but before therapeutic treatment and there were no significant differences in titres between the mock-treatment group and the DISC HSV-1 treated groups. Thus therapeutic administration of DISC HSV-1 virus either intra-vaginally or intra-epithelially resulted in an apparent reduction (20-25%) in the frequency of recurrence compared with mock-treated animals.

(4) The following experiment was designed to investigate the therapeutic value of a DISC virus based on HSV-2. A DISC HSV-2 (strain HG 52) having a deletion of the gH gene was made as described earlier and in accordance with the general teaching hereof, also using standard procedures in the art. The DISC version of the strain was grown in Vero cells transfected with the HSV-2 gH gene also in accordance with the teaching hereof.

The experiment was a head to head comparison of DISC HSV-1 with DISC HSV-2 in female 350-400 gms guinea-pigs. Guinea-pigs were divided into three groups. All guinea-pigs were infected with $10^{5.8}$ pfu HSV-2 strain MS. Four weeks were then allowed for the primary disease to have both developed and resolved and for recurrences to have started. The animals were then treated. A first group of 15 animals was treated intravaginally with a mock preparation of virus consisting of sonicated Vero cells. A second group of 13 animals was treated intravaginally with $10^7$ pfu DISC HSV-1. A third group of 14 animals was treated intravaginally with $10^7$ pfu DISC HSV-2. Treatment was repeated in 14 days. The results are shown in Table G-3. Days 1-13 covers the period between the two treatments. Days 14-27 covers the two week period subsequent to the second treatment. Days 1-27 covers the complete period.

As shown by the results, it appears that treatment with DISC HSV-2 was effective in alleviating symptoms caused by infection with HSV-2 strain MS. Treatment with DISC HSV-2 was more effective than treatment with DISC HSV-1.

The invention described and the disclosure made herein are susceptible of many modifications and variations as will be apparent to, and readily performable by, the skilled reader: and the disclosure extends to combinations and subcombinations of the features mentioned and/or described herein. Documents cited herein are hereby incorporated by reference.

TABLE G-3

| Group | Erythema scores | | | Lesions scores | | | Disease Days | | |
| --- | --- | --- | --- | --- | --- | --- | --- | --- | --- |
|  | Total | Per animal | % of Mock | Total | Per animal | % of Mock | Total | Per animal | % of Mock |
| Days 1-13 | | | | | | | | | |
| Mock | 38 | 2.53 | 100 | 66 | 4.40 | 100 | 42 | 2.80 | 100 |
| DISC HSV-1 | 34 | 2.62 | 103 | 48 | 3.69 | 84 | 34 | 2.62 | 93 |
| DISC HSV-2 | 22 | 1.57 | 62 | 40 | 2.86 | 65 | 26 | 1.86 | 66 |
| Days 14-27 | | | | | | | | | |
| Mock | 13 | 0.87 | 100 | 23 | 1.53 | 100 | 17 | 1.13 | 100 |
| DISC HSV-1 | 9 | 0.69 | 80 | 14 | 1.08 | 70 | 11 | 0.85 | 75 |
| DISC HSV-2 | 2 | 0.14 | 16 | 3 | 0.21 | 14 | 3 | 0.21 | 19 |

TABLE G-3-continued

| Group | Erythema scores | | | Lesions scores | | | Disease Days | | |
|---|---|---|---|---|---|---|---|---|---|
| | Total | Per animal | % of Mock | Total | Per animal | % of Mock | Total | Per animal | % of Mock |
| Days 1-27 | | | | | | | | | |
| Mock | 51 | 3.40 | 100 | 89 | 5.93 | 100 | 59 | 3.93 | 100 |
| DISC HSV-1 | 43 | 3.31 | 97 | 62 | 4.77 | 80 | 45 | 3.46 | 88 |
| DISC HSV-2 | 24 | 1.71 | 50 | 43 | 3.07 | 52 | 29 | 2.07 | 53 |

The invention claimed is:

1. A vaccine comprising a pharmaceutically acceptable excipient and an effective immunizing amount of a mutant virus, wherein said mutant virus is a mutant poxvirus and has a genome which has an inactivating mutation in a viral gene, said viral gene being essential for the production of infectious new virus particles, wherein said mutant virus is able to cause production of infectious new virus particles in a complementing host cell expressing a gene which complements said essential viral gene, but is unable to cause production of infectious new virus particles when said mutant virus infects a host cell other than a complementing host cell; for prophylactic or therapeutic use in generating an immune response in a subject.

2. The vaccine of claim 1 wherein the poxvirus is an orthopoxvirus.

3. The vaccine of claim 2 wherein the poxvirus is a vaccinia virus.

* * * * *

SEQUENCE LISTING

<160> NUMBER OF SEQ ID NOS: 21

<210> SEQ ID NO 1
<211> LENGTH: 21
<212> TYPE: DNA
<213> ORGANISM: Artificial sequence
<220> FEATURE:
<223> OTHER INFORMATION: Description of Artificial Sequence: primer

<400> SEQUENCE: 1
gatccaccat gaccatgatt a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
gatctaatca tggtcatggt g                                              21

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 3
atcaagcttc ccgggcctgg cattatgccc agtacatg                            38

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 4
tcaaagcttg agctctgatt atatagacct ccc                                 33

<210> SEQ ID NO 5
<211> LENGTH: 3836
<212> TYPE: DNA
<213> ORGANISM: Herpes Simplex Virus-2
<220> FEATURE:
<221> NAME/KEY: CDS
<222> LOCATION: (720)..(3230)
<220> FEATURE:
<221> NAME/KEY: misc_feature
<222> LOCATION: (760)..(760)
<223> OTHER INFORMATION: n is a, c, g, or t

```
<220> FEATURE:
<221> NAME/KEY: misc_feature
<222> LOCATION: (1241)..(1241)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1375)..(1375)
<223> OTHER INFORMATION: n is a, c, g, or t
<220> FEATURE:
<221> NAME/KEY: misc_feature
<222> LOCATION: (1713)..(1713)
<223> OTHER INFORMATION: n is a, c, g, or t
<220> FEATURE:
<221> NAME/KEY: misc_feature
<222> LOCATION: (2611)..(2611)
<223> OTHER INFORMATION: n is a, c, g, or t
<220> FEATURE:
<221> NAME/KEY: misc_feature
<222> LOCATION: (2689)..(2689)
<223> OTHER INFORMATION: n is a, c, g, or t
<220> FEATURE:
<221> NAME/KEY: misc_feature
<222> LOCATION: (3620)..(3620)
<223> OTHER INFORMATION: n is a, c, g, or t

<400> SEQUENCE: 5
ctgcagcgcg gcgggaggtg gcgggaggac tggggccggc tgacgggggt cgccgcggcg      60
accccgcgcc ccgaccccga ggacggcgcg gggtctctgc cccgcatcga ggacacgctg     120
tttgccctgt tccgcgttcc cgagctgctg gcccccaacg gggacttgta ccacattttt     180
gcctgggtct tggacgtctt ggccgaccgc ctccttccga tgcatctatt tgtcctggat     240
tacgatcagt cgcccgtcgg ggtgtcgagac gccctgttgc gcctcaccgc cgggatgatc     300
ccaacccgcg tcacaaccgc cgggtccatc gccgagatac gcgacctggc gcgcacgttt     360
gcccgcgagg tgggggggagt ttagttcaaa cacggaagcc cgaacggaag gcctcccggc     420
gatgacggca ataaaagaac agaataaaag gcattgttgt cgtgtggtgt gtccataagc     480 gcggggggttc ggggccaggg ctggcaccgt atcagcaccc caccgaaaaa cggagcgggc     540
cgatccgtcc ttgttttcgg tctggtactc cctttgtgct tttaccctca ccccacccca     600
tcctttggcc cgcgcttacg gcaacaaagg gcctccgata gcctccgagg tgcggacgct     660
ctttgggccg tgggtacgga caccccccca tctgcggact ggcagccggg acgacgacc     719 atg ggc ccc ggt ctg tgg gtg gtg atg ggg gtc ctg gtg gnc gtt gcc      767
Met Gly Pro Gly Leu Trp Val Val Met Gly Val Leu Val Xaa Val Ala
 1               5                  10                  15 ggg ggc cat gac acg tac tgg acg gag caa atc gac ccg tgg ttt ttg      815
Gly Gly His Asp Thr Tyr Trp Thr Glu Gln Ile Asp Pro Trp Phe Leu
                 20                  25                  30 cac ggt ctg ggg ttg gcc cgc acg tac tgg cgc gac aca aac acc ggg      863
His Gly Leu Gly Leu Ala Arg Thr Tyr Trp Arg Asp Thr Asn Thr Gly
         35                  40                  45 cgt ctg tgg ttg ccc aac acc ccc gac gac cag cga ccc cca gcg cgg      911
Arg Leu Trp Leu Pro Asn Thr Pro Asp Asp Gln Arg Pro Pro Ala Arg
 50                  55                  60 acg ctt ggc gcc ccc ggg caa ctc aac ctg act acg gca tcc gtg ccc      959
Thr Leu Gly Ala Pro Gly Gln Leu Asn Leu Thr Thr Ala Ser Val Pro
 65                  70                  75                  80 atg ctt cgg tgg tac gcc gag cgc ttt tgt ttc gtg ttg gtc acc acg     1007
Met Leu Arg Trp Tyr Ala Glu Arg Phe Cys Phe Val Leu Val Thr Thr
                 85                  90                  95
```

```
                                                   -continued gcc gag ttt cct cgg gac ccc ggg cag ctg ctt tac atc cca aag acc        1055
Ala Glu Phe Pro Arg Asp Pro Gly Gln Leu Leu Tyr Ile Pro Lys Thr
            100                 105                 110 tat ctg ctc ggc cgg cct cgg aac gcg agc ctg ccc gag ctc ccc gag        1103
Tyr Leu Leu Gly Arg Pro Arg Asn Ala Ser Leu Pro Glu Leu Pro Glu
        115                 120                 125 gcg ggg ccc acg tcc cgt ccc ccc gcc gag gtg acc cag ctc aag gga        1151
Ala Gly Pro Thr Ser Arg Pro Pro Ala Glu Val Thr Gln Leu Lys Gly
    130                 135                 140 ctg ctg cac aac ccc ggc gcc tcc gcg atg ttg cgg tcc cgg gcc tgg        1199
Leu Leu His Asn Pro Gly Ala Ser Ala Met Leu Arg Ser Arg Ala Trp
145                 150                 155                 160 gta aca ttc gcg gcc gcg ccg gac cgc gag ggg ctt acg ttn ccg cgg        1247
Val Thr Phe Ala Ala Ala Pro Asp Arg Glu Gly Leu Thr Xaa Pro Arg
                165                 170                 175 gga gac gac ggg gcg acc gag agg cac ccg gac ggc cga cgc aac gcg        1295
Gly Asp Asp Gly Ala Thr Glu Arg His Pro Asp Gly Arg Arg Asn Ala
            180                 185                 190 ncc ccg ggg ccg ccc gcg ggg gcg ccg agg cat ccg acg acg aac ctg        1343
Xaa Pro Gly Pro Pro Ala Gly Ala Pro Arg His Pro Thr Thr Asn Leu
        195                 200                 205 agc atc gcg cat ctg cac aac gcg tcc gtg anc ctg ctg gcc gcc agg        1391
Ser Ile Ala His Leu His Asn Ala Ser Val Xaa Leu Leu Ala Ala Arg
    210                 215                 220 ggc ctg cta cgg act ccg ggt cgg tac gtg tac ctc tcc ccg tcg gcc        1439
Gly Leu Leu Arg Thr Pro Gly Arg Tyr Val Tyr Leu Ser Pro Ser Ala
225                 230                 235                 240 tcg acg tgg ccc gtg ggc gtc tgg acg acg ggc ggg ctg gcg ttc ggg        1487
Ser Thr Trp Pro Val Gly Val Trp Thr Thr Gly Gly Leu Ala Phe Gly
                245                 250                 255 tgc gac gcc gcg ctc gtg cgc gcg cga tac ggg aag ggc ttc atg ggg        1535
Cys Asp Ala Ala Leu Val Arg Ala Arg Tyr Gly Lys Gly Phe Met Gly
            260                 265                 270 ctc gtg ata tcg atg cgg gac agc cct ccg gcc gag atc ata gtg gtg        1583
Leu Val Ile Ser Met Arg Asp Ser Pro Pro Ala Glu Ile Ile Val Val
        275                 280                 285 cct gcg gac aag acc ctc gct cgg gtc gga aat ccg acc gac gaa aac        1631
Pro Ala Asp Lys Thr Leu Ala Arg Val Gly Asn Pro Thr Asp Glu Asn
    290                 295                 300 gcc ccg cgt gct ccc cgc gct ccg gcc ggc ccc agg tat cgc gtc ttt        1679
Ala Pro Arg Ala Pro Arg Ala Pro Ala Gly Pro Arg Tyr Arg Val Phe
305                 310                 315                 320 gtc ctg ggg gcc ccg acg ccc gcc gac aac ggc ntc ggc gct gga ccc        1727
Val Leu Gly Ala Pro Thr Pro Ala Asp Asn Gly Xaa Gly Ala Gly Pro
                325                 330                 335 cct cgg cgg gtg gcc ggc tac ccc gag gag agc acg aac tac gcc cag        1775
Pro Arg Arg Val Ala Gly Tyr Pro Glu Glu Ser Thr Asn Tyr Ala Gln
            340                 345                 350 tat atg tcg cgg gcc tat gcg gag ttt ttg ggg gag gac ccg ggc tcc        1823
Tyr Met Ser Arg Ala Tyr Ala Glu Phe Leu Gly Glu Asp Pro Gly Ser
        355                 360                 365 ggc acg gac gac gcg cgt ccg tcc ctg ttc tgg cgc ctc gcg ggg ctg        1871
Gly Thr Asp Asp Ala Arg Pro Ser Leu Phe Trp Arg Leu Ala Gly Leu
    370                 375                 380 ctc gcc tcg tcg ggg ttt gcg ttc gtc aac gcg gcc cac gcc cac gac        1919
Leu Ala Ser Ser Gly Phe Ala Phe Val Asn Ala Ala His Ala His Asp
385                 390                 395                 400 gcg att cgc ctc tcc gac ctg ctg ggt ttt ttg gcc cac tcg cgc gtg        1967
Ala Ile Arg Leu Ser Asp Leu Leu Gly Phe Leu Ala His Ser Arg Val
                405                 410                 415
```

```
ctg gcc ggc ctg gcc gcc cgg gga gca gcg ggc tgc gcg gcc gac tcg         2015
Leu Ala Gly Leu Ala Ala Arg Gly Ala Ala Gly Cys Ala Ala Asp Ser
            420                 425                 430 gtg ttc ctg aac gtg tcc gtg ttg gac ccg gcg gcc cgt ctg cgg ctg         2063
Val Phe Leu Asn Val Ser Val Leu Asp Pro Ala Ala Arg Leu Arg Leu
            435                 440                 445 gag gcg cgc ctc ggg cat ctg gtg gcc gcg atc ctc gag cga gag cag         2111
Glu Ala Arg Leu Gly His Leu Val Ala Ala Ile Leu Glu Arg Glu Gln
450                 455                 460 agc ctg gcg gcg cac gcg ctg ggc tat cag ctg gcg ttc gtg ttg gac         2159
Ser Leu Ala Ala His Ala Leu Gly Tyr Gln Leu Ala Phe Val Leu Asp
465                 470                 475                 480 agc ccc gcg gcc tat ggc ggg ttg gcc ccg agc gcg gcc cgc ctg atc         2207
Ser Pro Ala Ala Tyr Gly Gly Leu Ala Pro Ser Ala Ala Arg Leu Ile
                485                 490                 495 gac gcc ctt gtt acc gcg cag ttt ctc ggc ggc cgc gta acc gcc ccg         2255
Asp Ala Leu Val Thr Ala Gln Phe Leu Gly Gly Arg Val Thr Ala Pro
            500                 505                 510 atg gtc cgc cga gcg ctg ttt tac gcc acg gcc gtc ctc cgg gcg ccg         2303
Met Val Arg Arg Ala Leu Phe Tyr Ala Thr Ala Val Leu Arg Ala Pro
            515                 520                 525 ttc ctg gcg ggc gtg ccc tcg gcc ggg cag cgg gaa cgc ccg cgg ggc         2351
Phe Leu Ala Gly Val Pro Ser Ala Gly Gln Arg Glu Arg Pro Arg Gly
530                 535                 540 ctc ctc ata acc acg gcc ctg tgt acg tcc gac gtc gcc gcg gcg acc         2399
Leu Leu Ile Thr Thr Ala Leu Cys Thr Ser Asp Val Ala Ala Ala Thr
545                 550                 555                 560 cac gcc gat ctc cgg gcc gcg cta cgc agg acc gac cac cag aaa aac         2447
His Ala Asp Leu Arg Ala Ala Leu Arg Arg Thr Asp His Gln Lys Asn
                565                 570                 575 ctc ttc tgg ctc ccg gac cac ttt tcc cca tgc gca cgt tcc ctg ccg         2495
Leu Phe Trp Leu Pro Asp His Phe Ser Pro Cys Ala Arg Ser Leu Pro
            580                 585                 590 ttc gat ctc gcc gag ggc ggg ttc atc ctg gac gcg ctg gcc atg gcc         2543
Phe Asp Leu Ala Glu Gly Gly Phe Ile Leu Asp Ala Leu Ala Met Ala
            595                 600                 605 acc cga tcc gac atc ccg gcg gac gtc atg gca caa cag acc cgc ggc         2591
Thr Arg Ser Asp Ile Pro Ala Asp Val Met Ala Gln Gln Thr Arg Gly
610                 615                 620 gtg gcc tcc gct ctc acg cnc tgg gcg act cac aac gcc ctg atc cgc         2639
Val Ala Ser Ala Leu Thr Xaa Trp Ala Thr His Asn Ala Leu Ile Arg
625                 630                 635                 640 gcc ttc gtc ccg gag gcc acc cac cag tgt agc ggc ccg tcg cac aac         2687
Ala Phe Val Pro Glu Ala Thr His Gln Cys Ser Gly Pro Ser His Asn
                645                 650                 655 gng gag ccc cgg atc ctc gtg ccc atc acc cac aac gcc agc tac gtc         2735
Xaa Glu Pro Arg Ile Leu Val Pro Ile Thr His Asn Ala Ser Tyr Val
            660                 665                 670 gtc acc cac tac ccc cct tgc ccc cgc ggg atc gga tac aag ctt acg         2783
Val Thr His Tyr Pro Pro Cys Pro Arg Gly Ile Gly Tyr Lys Leu Thr
            675                 680                 685 ggc gtt gac gtc cgc cgc ccg ctg ttt atc acc tat ctc acc gcc acc         2831
Gly Val Asp Val Arg Arg Pro Leu Phe Ile Thr Tyr Leu Thr Ala Thr
            690                 695                 700 tgc gaa ggg cac gcg cgg gag att gag ccg ccg cgg ctg gtg cgc acc         2879
Cys Glu Gly His Ala Arg Glu Ile Glu Pro Pro Arg Leu Val Arg Thr
705                 710                 715                 720 gaa aac cgg cgc gac ctc ggc ctc gtg ggg gcc gtg ttt ctg cgc tac         2927
Glu Asn Arg Arg Asp Leu Gly Leu Val Gly Ala Val Phe Leu Arg Tyr
```

-continued

```
                      725                 730                 735
acc ccg gcc ggg gag gtc atg tcg gtg ctg ctg gtg gac acg gat gcc      2975
Thr Pro Ala Gly Glu Val Met Ser Val Leu Leu Val Asp Thr Asp Ala
            740                 745                 750 acc caa cag cag ctg gcc cag ggg ccg gtg gcg ggc acc ccg aac gtg      3023
Thr Gln Gln Gln Leu Ala Gln Gly Pro Val Ala Gly Thr Pro Asn Val
        755                 760                 765 ttt tcc agc gac gtg ccg tcc gtg gcc ctg ttg ttc ccc aac gga          3071
Phe Ser Ser Asp Val Pro Ser Val Ala Leu Leu Phe Pro Asn Gly
    770                 775                 780 act gtg att cat ctg ctg gcc ttt gac acg ctg ccc atc gcc acc atc      3119
Thr Val Ile His Leu Leu Ala Phe Asp Thr Leu Pro Ile Ala Thr Ile
785                 790                 795                 800 gcc ccc ggg ttt ctg gcc gcg tcc gcg ctg ggg gtc gtt atg att acc      3167
Ala Pro Gly Phe Leu Ala Ala Ser Ala Leu Gly Val Val Met Ile Thr
                805                 810                 815 gcg gcc ctg gcg ggc atc ctc agg gtg gtc cga acg tgc gtc cca ttt      3215
Ala Ala Leu Ala Gly Ile Leu Arg Val Val Arg Thr Cys Val Pro Phe
            820                 825                 830 ttg tgg aga cgc gaa taaacgggtg tgtggacgca gcggcgtcca gcccaaccca      3270
Leu Trp Arg Arg Glu
        835 accgactccc tccgtgtccg cggtctgttt gttattgtgt ccgccgtggc tccgctaccg    3330 cctctgttcc tttcccttct ccattcctgt ttccttttcct tccccccccc ccatagtccc   3390 ccgtataggc atacaacggc atccgtgggt tagaaaacga ctgcacttta ttgggatatc    3450 tcacacagac tggccgtgct gggcgcgagc caggcaaacg gtaagcagcg cgtccaggta    3510 cccggcggtt cgcgtgcggc cagccgcccc cgccggcccg cggtcaaacg cggacatccg    3570 gtcgacgtcc cccacggtca ggaccaggga cgtcacgccc gtcaggcgcn cggtatgcgt    3630 ggccgcggcc aggcgtccgt ggccggcgta caacacgccc aggaacgcgc cgaggtacat    3690 gacgtgctcg ggcgagacgg accccccgg ggtcaggcgt tgcgagtcca caaagcgcag     3750 cagggcggcg ctgtcggccc gcgacgtcgc tccccaccgg cacgtccttg ggcgggagga    3810 ggtcgaacat gaggagctgc tcgcga                                         3836
```

<210> SEQ ID NO 6
<211> LENGTH: 837
<212> TYPE: PRT
<213> ORGANISM: Herpes Simplex Virus-2
<220> FEATURE:
<221> NAME/KEY: misc_feature
<222> LOCATION: (14)..(14)
<223> OTHER INFORMATION: The 'Xaa' at location 14 stands for Asp, Gly,
      Ala, or Val.
<220> FEATURE:
<221> NAME/KEY: misc_feature
<222> LOCATION: (174)..(174)
<223> OTHER INFORMATION: The 'Xaa' at location 174 stands for Leu, or
      Phe.
<220> FEATURE:
<221> NAME/KEY: misc_feature
<222> LOCATION: (193)..(193)
<223> OTHER INFORMATION: The 'Xaa' at location 193 stands for Thr, Ala,
      Pro, or Ser.
<220> FEATURE:
<221> NAME/KEY: misc_feature
<222> LOCATION: (219)..(219)
<223> OTHER INFORMATION: The 'Xaa' at location 219 stands for Asn, Ser,
      Thr, or Ile.
<220> FEATURE:
<221> NAME/KEY: misc_feature
<222> LOCATION: (332)..(332)
<223> OTHER INFORMATION: The 'Xaa' at location 332 stands for Ile, Val, Leu, or Phe.
<220> FEATURE:
<221> NAME/KEY: misc_feature
<222> LOCATION: (631)..(631)
<223> OTHER INFORMATION: The 'Xaa' at location 631 stands for His, Arg, Pro, or Leu.
<220> FEATURE:
<221> NAME/KEY: misc_feature
<222> LOCATION: (657)..(657)
<223> OTHER INFORMATION: The 'Xaa' at location 657 stands for Glu, Gly, Ala, or Val.

<400> SEQUENCE: 6

```
Met Gly Pro Gly Leu Trp Val Val Met Gly Val Leu Val Xaa Val Ala
1               5                   10                  15

Gly Gly His Asp Thr Tyr Trp Thr Glu Gln Ile Asp Pro Trp Phe Leu
            20                  25                  30

His Gly Leu Gly Leu Ala Arg Thr Tyr Trp Arg Asp Thr Asn Thr Gly
        35                  40                  45

Arg Leu Trp Leu Pro Asn Thr Pro Asp Asp Gln Arg Pro Pro Ala Arg
50                  55                  60

Thr Leu Gly Ala Pro Gly Gln Leu Asn Leu Thr Thr Ala Ser Val Pro
65                  70                  75                  80

Met Leu Arg Trp Tyr Ala Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Arg Asn Ala Ser Leu Pro Glu Leu Pro Glu
        115                 120                 125

Ala Gly Pro Thr Ser Arg Pro Pro Ala Glu Val Thr Gln Leu Lys Gly
130                 135                 140

Leu Leu His Asn Pro Gly Ala Ser Ala Met Leu Arg Ser Arg Ala Trp
145                 150                 155                 160

Val Thr Phe Ala Ala Pro Asp Arg Glu Gly Leu Thr Xaa Pro Arg
                165                 170                 175

Gly Asp Asp Gly Ala Thr Glu Arg His Pro Asp Gly Arg Arg Asn Ala
            180                 185                 190

Xaa Pro Gly Pro Pro Ala Gly Ala Pro Arg His Pro Thr Thr Asn Leu
        195                 200                 205

Ser Ile Ala His Leu His Asn Ala Ser Val Xaa Leu Leu Ala Ala Arg
210                 215                 220

Gly Leu Leu Arg Thr Pro Gly Arg Tyr Val Tyr Leu Ser Pro Ser Ala
225                 230                 235                 240

Ser Thr Trp Pro Val Gly Val Trp Thr Thr Gly Gly Leu Ala Phe Gly
                245                 250                 255

Cys Asp Ala Ala Leu Val Arg Ala Arg Tyr Gly Lys Gly Phe Met Gly
            260                 265                 270

Leu Val Ile Ser Met Arg Asp Ser Pro Ala Glu Ile Ile Val Val
        275                 280                 285

Pro Ala Asp Lys Thr Leu Ala Arg Val Gly Asn Pro Thr Asp Glu Asn
290                 295                 300

Ala Pro Arg Ala Pro Arg Ala Pro Ala Gly Pro Arg Tyr Arg Val Phe
305                 310                 315                 320

Val Leu Gly Ala Pro Thr Pro Ala Asp Asn Gly Xaa Gly Ala Gly Pro
                325                 330                 335

Pro Arg Arg Val Ala Gly Tyr Pro Glu Glu Ser Thr Asn Tyr Ala Gln
            340                 345                 350
```

```
Tyr Met Ser Arg Ala Tyr Ala Glu Phe Leu Gly Glu Asp Pro Gly Ser
        355                 360                 365

Gly Thr Asp Asp Ala Arg Pro Ser Leu Phe Trp Arg Leu Ala Gly Leu
        370                 375                 380

Leu Ala Ser Ser Gly Phe Ala Phe Val Asn Ala Ala His Ala His Asp
385                 390                 395                 400

Ala Ile Arg Leu Ser Asp Leu Leu Gly Phe Leu Ala His Ser Arg Val
                405                 410                 415

Leu Ala Gly Leu Ala Ala Arg Gly Ala Ala Gly Cys Ala Ala Asp Ser
            420                 425                 430

Val Phe Leu Asn Val Ser Val Leu Asp Pro Ala Ala Arg Leu Arg Leu
        435                 440                 445

Glu Ala Arg Leu Gly His Leu Val Ala Ala Ile Leu Glu Arg Glu Gln
        450                 455                 460

Ser Leu Ala Ala His Ala Leu Gly Tyr Gln Leu Ala Phe Val Leu Asp
465                 470                 475                 480

Ser Pro Ala Ala Tyr Gly Gly Leu Ala Pro Ser Ala Ala Arg Leu Ile
                485                 490                 495

Asp Ala Leu Val Thr Ala Gln Phe Leu Gly Gly Arg Val Thr Ala Pro
            500                 505                 510

Met Val Arg Arg Ala Leu Phe Tyr Ala Thr Ala Val Leu Arg Ala Pro
        515                 520                 525

Phe Leu Ala Gly Val Pro Ser Ala Gly Gln Arg Glu Arg Pro Arg Gly
        530                 535                 540

Leu Leu Ile Thr Thr Ala Leu Cys Thr Ser Asp Val Ala Ala Ala Thr
545                 550                 555                 560

His Ala Asp Leu Arg Ala Ala Leu Arg Arg Thr Asp His Gln Lys Asn
                565                 570                 575

Leu Phe Trp Leu Pro Asp His Phe Ser Pro Cys Ala Arg Ser Leu Pro
            580                 585                 590

Phe Asp Leu Ala Glu Gly Gly Phe Ile Leu Asp Ala Leu Ala Met Ala
        595                 600                 605

Thr Arg Ser Asp Ile Pro Ala Asp Val Met Ala Gln Gln Thr Arg Gly
        610                 615                 620

Val Ala Ser Ala Leu Thr Xaa Trp Ala Thr His Asn Ala Leu Ile Arg
625                 630                 635                 640

Ala Phe Val Pro Glu Ala Thr His Gln Cys Ser Gly Pro Ser His Asn
                645                 650                 655

Xaa Glu Pro Arg Ile Leu Val Pro Ile Thr His Asn Ala Ser Tyr Val
            660                 665                 670

Val Thr His Tyr Pro Pro Cys Pro Arg Gly Ile Gly Tyr Lys Leu Thr
        675                 680                 685

Gly Val Asp Val Arg Arg Pro Leu Phe Ile Thr Tyr Leu Thr Ala Thr
        690                 695                 700

Cys Glu Gly His Ala Arg Glu Ile Glu Pro Pro Arg Leu Val Arg Thr
705                 710                 715                 720

Glu Asn Arg Arg Asp Leu Gly Leu Val Gly Ala Val Phe Leu Arg Tyr
                725                 730                 735

Thr Pro Ala Gly Glu Val Met Ser Val Leu Leu Val Asp Thr Asp Ala
            740                 745                 750

Thr Gln Gln Gln Leu Ala Gln Gly Pro Val Ala Gly Thr Pro Asn Val
        755                 760                 765
```

```
Phe Ser Ser Asp Val Pro Ser Val Ala Leu Leu Phe Pro Asn Gly
    770                 775                 780

Thr Val Ile His Leu Leu Ala Phe Asp Thr Leu Pro Ile Ala Thr Ile
785                 790                 795                 800

Ala Pro Gly Phe Leu Ala Ala Ser Ala Leu Gly Val Val Met Ile Thr
                805                 810                 815

Ala Ala Leu Ala Gly Ile Leu Arg Val Val Arg Thr Cys Val Pro Phe
            820                 825                 830

Leu Trp Arg Arg Glu
        835

<210> SEQ ID NO 7
<211> LENGTH: 3762
<212> TYPE: DNA
<213> ORGANISM: Herpes Simplex Virus-1

<400> SEQUENCE: 7
ctgcagggcg gcgggtcgtg gcgggaggat tggggacagc tttcgggggc ggccgtgccg      60
ccccagggtg ccgagcccca gagcaacgcg ggcccacgac cccatatcgg ggacacgtta     120
tttaccctgt ttcgggcccc cgagttgctg gcccccaacg gcgacctgta taacgtgttt     180
gcctgggctt tggacgtctt ggccaaacgc ctccgtccca tgcatgtctt tatcctggat     240
tacgaccaat cgcccgccgg ctgccgggac gccctgctgc aacttacctc cgggatggtc     300
cagacccacg tcaccacccc aggctccata ccgacgatct gcgacctggc gcgcacgttt     360
gcccgggaga tccgggagcc taactgaaac acggaaggag acaataccgg aaggaacccg     420
cgctatgacg gcaataaaaa gacagaataa aacgcacggg tgttgggtcg tttgttcata     480
aacgcggggt tcggtcccag ggctggcact ctgtcgatac cccaccgaga ccccattggg     540
accaatacgc ccgcgtttct tcctttccc cacccccaacc cccaagttcg ggtgaaggcc     600
cagggctcgc agccaacgtc ggggcggcaa gccctgccat agccacgggc cccgtgggtt     660
agggacgggg tcccccatgg ggaatggttt atggttcgtg ggggttatta ttttgggcgt     720
tgcgtggggt caggtccacg actggactga gcagacagac ccatggtttt tggatggcct     780
gggcatggac cgcatgtact ggcgcgacac gaacaccggg cgtctgtggc tgccaaacac     840
ccccgacccc caaaaaccac cgcgcggatt tctggcgccg ccggacgaac taaacctgac     900
tacggcatct ctgccccttc ttcgctggta cgaggagcgc ttttgttttg tattggtcac     960
cacggccgag tttccgcggg accccggcca gctgctttac atcccgaaga cctacctgct    1020
cggccggccc ccgaacgcga gcctgcccgc ccccaccacg gtcgagccga ccgcccagcc    1080 tccccctcg gtcgcccccc ttaagggtct cttgcacaat ccagccgcct ccgtgttgct    1140
gcgttcccgg gcctgggtaa cgttttcggc cgtccctgac cccgaggccc tgacgttccc    1200
gcggggagac aacgtggcga cggcgagcca cccgagcggg ccgcgtgata cccgcccccc    1260
cgaccgccgg ttggggcccg gcggcacccg acgacggagc tggacatcac gcacctgcac    1320
aacgcgtcca cgacctggtt ggccaccccgg ggctgttga gatcccccagg taggtacgtg    1380 tatttctccc cgtcggcctc gacgtggccc gtgggcatct ggacgacggg ggagctggtg    1440
ctcgggtgcg atgccggggt ggtgcgcgcg cgctacgggc gggaattcat ggggctcgtg    1500
atatccatgc acgacagccc tccggtggaa gtgatggtgg tccccgcggg ccagacgcta    1560
gatcgggtcg ggaccccgc ggacgaaaac ccccgggggg ctcttcccgg gccccgggc    1620 ggccccggt atcgggtctt tgtcctaggg tccctgacgc ggggccgacaa cggctccgcg    1680
```

-continued

```
ctggacgccc tccgccgcgt gggcggctac ccggaggagg gcacgaacta cgcccagttc      1740
ctgtcgcggg catacgcgga gttttctcg ggggacgcgg gcgccgagca gggcccgcgc       1800
ccccctctct tctggcgcct aacggggctg ctcgcgacgt cgggttttgc tttcgtgaac      1860
gccgcccacg caaacggcgc ggtctgcctc tccgacctgc taggcttttt ggcccactcg      1920
cgcgcgcttg ccgggttggc cgcccgcgcg ccgcgggct gtgccgcgga ttctgtgttt       1980
tttaatgtgt cagtcttgga tcccacggcc cgcctgcagc tagaggctcg gctccagcac      2040
ctggtggccg agattctgga gcgcgaacag agcttggcat acacgcgct gggctatcag       2100 ctggccttcg tgctggatag ccccctcgcg tacgacgcag tggcgcccag cgcagcccat      2160
ctcatcgacg ccctgctatg cccgagtttc tagggggccg cgtgctgacc accccggtcg     2220
tccaccgggc gctatttac gcctcggctg tcctccggca gccgttcttg gctggcgtcc     2280
cctcggcggt gcagcgggaa cgcgcccgcc ggacccttct gatagcctcg gccctgtgta    2340
cgtccgacgt cgccgcagcg accaacgccg acctccggac cgcgctggcc cgggccgacc   2400
accagaaaac cctcttttgg cttccggacc acttttcgcc atgcgcggcc tcctgcgct    2460 ttgatctaga cgagagcgtg tttatcctgg acgcgctggc tcaagccacc cgatccgaga   2520
ccccggtcga agtcctggcc cagcagaccc acggcctcgc ctcgaccctg acgcgttggg   2580
cacactacaa cgccctgatc cgcgccttcg tccctgaggc ctcacatcgg tgcgggggc    2640 agtctgccaa cgtcgagcca cggatcctgg tacccatcac ccacaacgcc agctacgtcg   2700
tcacccactc ccctctgccc cggggggatcg gctacaagct caccggcgtc gacgtccgac   2760
gcccactgtt cctaacctac ctcaccgcga catgcgaagg ctccacccgg gatatcgagt   2820
ccaagcggct ggtgcgcacc caaaaccagc gcgacctggg gctcgtgggg gccgtgttta   2880
tgcgctacac cccggccggg gaggtcatgt ctgtgttgct ggtggatacg gacaacacac    2940
agcagcaaat cgccgccggg ccgacggagg gcgcccaag cgtgttttcg agcgacgtgc    3000
cgtccacggc cttgttgcta tttccaaacg gaaccgtcat tcatttgcta gccttttgaca  3060 cgcagcccgt ggccgcaatt gcgcccgggt ttctggccgc ctctgcgctg gcgtggtta    3120 tgattaccgc cgccctggct ggcatcctaa aggttctccg gacaagtgtc ccgttttttt   3180
ggagacgcga ataaagtggg cgtggcttcg gccgtttctc cgcccgaccg aataaactgt   3240
aaccgtgtct gtggtttgtt tgttcaggcc ccggtggtgc cgctccccca gcccctcttt   3300
gctttccctc ccccccccc ggagaggcgt ccattgacac acaagggtgt agtagcgata    3360
tacgtttatt ggggtctttt acacagactg tccgtgttgg gagcgagcga gacgaacggt   3420
aagaagcaca tccaggtacc cggcggcccc cgtgcggctg gccgcgcccg ccgctccgcg   3480
gtcaaacgcg gaaagacggt ccacgtcacc caccgctagc accagggagg tcaccctgt    3540 cagccgcgcg gtgtgcgtgg ctgcggacat gcgcccgcgg ccagcgtaca gcacgctcag   3600 gaacgccacca aggtacgcga cgtgctcggg ggagatcacc cccccgggga cggcgagacg  3660
ttgcgattct ataaagcgca gcagagcggt gctgtcggcc tgcacgtcgc ttcccaccgg   3720
cacgtccttt gggggagaa ggtcgaacat gagagctgct cg                         3762
```

<210> SEQ ID NO 8
<211> LENGTH: 838
<212> TYPE: PRT
<213> ORGANISM: Herpes Simplex Virus-1

<400> SEQUENCE: 8

Met Gly Asn Gly Leu Trp Phe Val Gly Val Ile Ile Leu Gly Val Ala

-continued

```
1               5                    10                   15
Trp Gly Gln Val His Asp Trp Thr Glu Gln Thr Asp Pro Trp Phe Leu
            20                  25                  30
Asp Gly Leu Gly Met Asp Arg Met Tyr Trp Arg Asp Thr Asn Thr Gly
            35                  40                  45
Arg Leu Trp Leu Pro Asn Thr Pro Asp Pro Gln Lys Pro Pro Arg Gly
    50                  55                  60
Phe Leu Ala Pro Pro Asp Glu Leu Asn Leu Thr Thr Ala Ser Leu Pro
65                  70                  75                  80
Leu Leu Arg Trp Tyr Glu Glu Arg Phe Cys Phe Val Leu Val Thr Thr
                85                  90                  95
Ala Glu Phe Pro Arg Asp Pro Gly Gln Leu Leu Tyr Ile Pro Lys Thr
                100                 105                 110
Tyr Leu Leu Gly Arg Pro Pro Asn Ala Ser Leu Pro Ala Pro Thr Thr
            115                 120                 125
Val Glu Pro Thr Ala Gln Pro Pro Ser Val Ala Pro Leu Lys Gly
            130                 135                 140
Leu Leu His Asn Pro Ala Ala Ser Val Leu Leu Arg Ser Arg Ala Trp
145                 150                 155                 160
Val Thr Phe Ser Ala Val Pro Asp Pro Glu Ala Leu Thr Phe Pro Arg
                165                 170                 175
Gly Asp Asn Val Ala Thr Ala Ser His Pro Ser Gly Pro Arg Asp Thr
                180                 185                 190
Pro Pro Pro Arg Pro Val Gly Ala Arg Arg His Pro Thr Thr Glu
            195                 200                 205
Leu Asp Ile Thr His Leu His Asn Ala Ser Thr Thr Trp Leu Ala Thr
210                 215                 220
Arg Gly Leu Leu Arg Ser Pro Gly Arg Tyr Val Tyr Phe Ser Pro Ser
225                 230                 235                 240
Ala Ser Thr Trp Pro Val Gly Ile Trp Thr Thr Gly Glu Leu Val Leu
                245                 250                 255
Gly Cys Asp Ala Ala Leu Val Arg Ala Arg Tyr Gly Arg Glu Phe Met
                260                 265                 270
Gly Leu Val Ile Ser Met His Asp Ser Pro Val Glu Val Met Val
            275                 280                 285
Val Pro Ala Gly Gln Thr Leu Asp Arg Val Gly Asp Pro Ala Asp Glu
    290                 295                 300
Asn Pro Pro Gly Ala Leu Pro Gly Pro Gly Gly Pro Arg Tyr Arg
305                 310                 315                 320
Val Phe Val Leu Gly Ser Leu Thr Arg Ala Asp Asn Gly Ser Ala Leu
                325                 330                 335
Asp Ala Leu Arg Arg Val Gly Gly Tyr Pro Glu Glu Gly Thr Asn Tyr
            340                 345                 350
Ala Gln Phe Leu Ser Arg Ala Tyr Ala Glu Phe Ser Gly Asp Ala
    355                 360                 365
Gly Ala Glu Gln Gly Pro Arg Pro Leu Phe Trp Arg Leu Thr Gly
    370                 375                 380
Leu Leu Ala Thr Ser Gly Phe Ala Phe Val Asn Ala Ala His Ala Asn
385                 390                 395                 400
Gly Ala Val Cys Leu Ser Asp Leu Leu Gly Phe Leu Ala His Ser Arg
                405                 410                 415
Ala Leu Ala Gly Leu Ala Ala Arg Gly Ala Ala Gly Cys Ala Ala Asp
            420                 425                 430
```

-continued

```
Ser Val Phe Phe Asn Val Ser Val Leu Asp Pro Thr Ala Arg Leu Gln
            435                 440                 445

Leu Glu Ala Arg Leu Gln His Leu Val Ala Glu Ile Leu Glu Arg Glu
        450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Leu Thr Thr
            500                 505                 510

Pro Val Val His Arg Ala Leu Phe Tyr Ala Ser Ala Val Leu Arg Gln
        515                 520                 525

Pro Phe Leu Ala Gly Val Pro Ser Ala Val Gln Arg Glu Arg Ala Arg
    530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
            580                 585                 590

Leu Arg Phe Asp Leu Asp Glu Ser Val Phe Ile Leu Asp Ala Leu Ala
        595                 600                 605

Gln Ala Thr Arg Ser Glu Thr Pro Val Glu Val Leu Ala Gln Gln Thr
    610                 615                 620

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
                645                 650                 655

Ala Asn Val Glu Pro Arg Ile Leu Val Pro Ile Thr His Asn Ala Ser
            660                 665                 670

Tyr Val Val Thr His Ser Pro Leu Pro Arg Gly Ile Gly Tyr Lys Leu
        675                 680                 685

Thr Gly Val Asp Val Arg Arg Pro Leu Phe Leu Thr Tyr Leu Thr Ala
    690                 695                 700

Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735

Tyr Thr Pro Ala Gly Glu Val Met Ser Val Leu Leu Val Asp Thr Asp
            740                 745                 750

Asn Thr Gln Gln Gln Ile Ala Ala Gly Pro Thr Glu Gly Ala Pro Ser
        755                 760                 765

Val Phe Ser Ser Asp Val Pro Ser Thr Ala Leu Leu Phe Pro Asn
    770                 775                 780

Gly Thr Val Ile His Leu Leu Ala Phe Asp Thr Gln Pro Val Ala Ala
785                 790                 795                 800

Ile Ala Pro Gly Phe Leu Ala Ala Ser Ala Leu Gly Val Val Met Ile
                805                 810                 815

Thr Ala Ala Leu Ala Gly Ile Leu Lys Val Leu Arg Thr Ser Val Pro
            820                 825                 830

Phe Phe Trp Arg Arg Glu
        835
```

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 9
tcagttaacg cctctgttcc tttcccttc                               29

<210> SEQ ID NO 10
<211> LENGTH: 57
<212> TYPE: DNA
<213> ORGANISM: Artificial sequence
<220> FEATURE:
<223> OTHER INFORMATION: Description of Artificial Sequence: primer

<400> SEQUENCE: 10
tcagttaact gcactagttt taattaatac gtatgccgtc cgtcccggct gccagtc      57

<210> SEQ ID NO 11
<211> LENGTH: 30
<212> TYPE: DNA
<213> ORGANISM: Artificial sequence
<220> FEATURE:
<223> OTHER INFORMATION: Description of Artificial Sequence: primer

<400> SEQUENCE: 11
tcaaagcttc tgcagcgcgg cgggaggtgg                              30

<210> SEQ ID NO 12
<211> LENGTH: 26
<212> TYPE: DNA
<213> ORGANISM: Artificial sequence
<220> FEATURE:
<223> OTHER INFORMATION: Description of Artificial Sequence: primer

<400> SEQUENCE: 12
gatccaccat gaccatgatt agatct                                  26

<210> SEQ ID NO 13
<211> LENGTH: 23
<212> TYPE: DNA
<213> ORGANISM: Artificial sequence
<220> FEATURE:
<223> OTHER INFORMATION: Description of Artificial Sequence: primer

<400> SEQUENCE: 13
gaagaaggct atagctaata cat                                     23

<210> SEQ ID NO 14
<211> LENGTH: 27
<212> TYPE: DNA
<213> ORGANISM: Artificial sequence
<220> FEATURE:
<223> OTHER INFORMATION: Description of Artificial Sequence: primer

<400> SEQUENCE: 14
caagaaataa actataggtc tttgtgc                                 27

<210> SEQ ID NO 15
<211> LENGTH: 38
<212> TYPE: DNA
<213> ORGANISM: Artificial sequence
<220> FEATURE:
<223> OTHER INFORMATION: Description of Artificial Sequence: primer

<400> SEQUENCE: 15
atcgaattcc tatagcctgg cattatgccc agtacatg                      38

<210> SEQ ID NO 16
<211> LENGTH: 45
<212> TYPE: DNA
<213> ORGANISM: Artificial sequence
<220> FEATURE:
<223> OTHER INFORMATION: Description of Artificial Sequence: primer

<400> SEQUENCE: 16
tcaaagcttc tatagcccgg ggagctctga ttatatagac ctccc              45

<210> SEQ ID NO 17
<211> LENGTH: 29
<212> TYPE: DNA
<213> ORGANISM: Artificial sequence
<220> FEATURE:
<223> OTHER INFORMATION: Description of Artificial Sequence: primer

<400> SEQUENCE: 17
tcagttaacc gtcgtcccgg ctgccagtc                                29

<210> SEQ ID NO 18
<211> LENGTH: 25
<212> TYPE: DNA
<213> ORGANISM: Artificial sequence
<220> FEATURE:
<223> OTHER INFORMATION: Description of Artificial Sequence: primer

<400> SEQUENCE: 18
tcgaagcttc agggagtggc gcagc                                    25

<210> SEQ ID NO 19
<211> LENGTH: 30
<212> TYPE: DNA
<213> ORGANISM: Artificial sequence
<220> FEATURE:
<223> OTHER INFORMATION: Description of Artificial Sequence: primer

<400> SEQUENCE: 19
tcagttaacg gacagcatgg ccaggtcaag                               30

<210> SEQ ID NO 20
<211> LENGTH: 57
<212> TYPE: DNA
<213> ORGANISM: Artificial sequence
<220> FEATURE:
<223> OTHER INFORMATION: Description of Artificial Sequence: primer

<400> SEQUENCE: 20
tcagttaact gcactagttt taattaatac gtatgccgtc cgtcccggct gccagtc  57

<210> SEQ ID NO 21
<211> LENGTH: 29
<212> TYPE: DNA
<213> ORGANISM: Artificial sequence
<220> FEATURE:
<223> OTHER INFORMATION: Description of Artificial Sequence: primer

<400> SEQUENCE: 21
tcagaattcg ttccgggagc aggcgtgga                                29